(12) United States Patent
Goodchild et al.

(10) Patent No.: US 10,881,746 B2
(45) Date of Patent: Jan. 5, 2021

(54) MEANS AND METHODS TO TREAT DYSTONIA

(71) Applicants: VIB VZW, Ghent (BE); KATHOLIEKE UNIVERSITEIT LEUVEN, K.U.LEUVEN R&D, Leuven (BE)

(72) Inventors: Rose Goodchild, Leuven (BE); Micheline Grillet, Ath (BE)

(73) Assignees: VIB VZW, Ghent (BE); Katholieke Universiteit Leuven, K.U. Leuven R & D, Leuven (BE)

( * ) Notice: Subject to any disclaimer, the term of this patent is extended or adjusted under 35 U.S.C. 154(b) by 0 days.

(21) Appl. No.: 16/307,609

(22) PCT Filed: Jun. 2, 2017

(86) PCT No.: PCT/EP2017/063431
§ 371 (c)(1),
(2) Date: Dec. 6, 2018

(87) PCT Pub. No.: WO2017/211707
PCT Pub. Date: Dec. 14, 2017

(65) Prior Publication Data
US 2019/0160184 A1 May 30, 2019

(30) Foreign Application Priority Data

Jun. 6, 2016 (EP) ..................................... 16173092
Aug. 8, 2016 (EP) ..................................... 16183216

(51) Int. Cl.
| | |
|---|---|
| *A61K 48/00* | (2006.01) |
| *C12N 15/113* | (2010.01) |
| *A61P 25/28* | (2006.01) |
| *C12Q 1/02* | (2006.01) |
| *A61K 31/7105* | (2006.01) |
| *A61K 31/713* | (2006.01) |
| *A61K 38/46* | (2006.01) |

(52) U.S. Cl.
CPC ...... *A61K 48/0058* (2013.01); *A61K 48/0008* (2013.01); *A61K 48/0091* (2013.01); *A61P 25/28* (2018.01); *C12N 15/1137* (2013.01); *C12Q 1/025* (2013.01); *C12Y 301/03004* (2013.01); *C12Y 301/03018* (2013.01); *A61K 31/713* (2013.01); *A61K 31/7105* (2013.01); *A61K 38/465* (2013.01); *C12N 2310/14* (2013.01)

(58) Field of Classification Search
CPC ........................ A01K 2207/05; C12N 15/113
See application file for complete search history.

(56) References Cited

U.S. PATENT DOCUMENTS

2007/0212333 A1  9/2007  Li et al.

OTHER PUBLICATIONS

Michot et al. Biochim Biophys Acta 1832: 2103-14, pp. 1-28 (Year: 2013).*
Chen et al. Ann Nutr Metab 66:10-18 (Year: 2015).*
Wang et al. Febs Letters 585, 1979-1984 (Year: 2011).*
Dwyer et al. PNAS E2486-2495 (Year: 2012).*
Csaki et al. Molecular Metabolism 3, 145-154 (Year: 2014).*
Rare disease database rarediseases.org/rare-diseases/dystonia, https://www.printfriendly.com/p/g/EdPpYq retrieved on Nov. 6, 2019, pp. 1-16 (Year: 2019).*
Gonzalez-Alegre Pedro et al., Toward Therapy for DYT1 Dystonia: Allele-Specific Silencing of Mutant Torsina, Annals of Neurol, John Wiley and Sons, Boston, US, vol. 53, No. 6, (Jun. 1, 2003), pp. 781-787, XP008073069, ISSN: 0364-5134. DOI: 10.1002/ANA.10548.
Grillet, Micheline et al., Torsins Are Essential Regulators of Cellular Lipid Metabolism, Developmental Cell, Cell Press, US, vol. 38, No. 3 (Jul. 21, 2016), pp. 235-247, XP029678726, ISSN: 1534-5807, DOI: 10.1016/J.DEVCEL.2016.06.017.
Hewett, J.W. et al., siRNA knock-down of mutant torsinA restores processing through secretory pathway in DYT1 dystonia cells, Human Molecular Genetics, vol. 17, No. 10, (Jan. 25, 2008), pp. 1436-1445, XP055401330, gb ISSN: 0964-6906, DOI: 10.1093/hmg/ddn032.
PCT International Search Report and Written Opinion, International Application No. PCT/EP20171063431, dated Sep. 1, 2017, 11 pages.
Cascalho, Ana et al., "Inhibition of Lipin Lipid Phosphatase Hyperactivity Rescues TorsinA Neurological Disease." bioRxiv, https://doi.org/10.1101/606947, Posted Apr. 16, 2019, 43 pgs.

* cited by examiner

*Primary Examiner* — Brian Whiteman
(74) *Attorney, Agent, or Firm* — Patent Law Works, LLP

(57) ABSTRACT

The present application relates to the field of neurological diseases, particularly to dystonia, even more particularly to primary dystonia, most particularly DYT1 primary dystonia. It is disclosed that the DYT1 dystonia causative mutation in TORSIN1A leads to hyperactivation of LIPIN. The invention provides substances modulating LIPIN function, in particular RNA molecules inhibiting LIPIN function and medical uses of these LIPIN inhibitors. Methods are disclosed to screen for medicaments that counteract the effects of TORSIN1A mutation.

3 Claims, 11 Drawing Sheets
(11 of 11 Drawing Sheet(s) Filed in Color)
Specification includes a Sequence Listing.

MEANS AND METHODS TO TREAT DYSTONIA

FIELD OF THE INVENTION

The present application relates to the field of neurological diseases, particularly to dystonia, even more particularly to primary dystonia, most particularly to DYT1 primary dystonia. It is disclosed that the DYT1 dystonia causative mutation in TORSIN1A leads to hyperactivation of LIPIN. The invention provides substances modulating LIPIN function, in particular RNA molecules inhibiting LIPIN function and medical uses of these LIPIN inhibitors. Methods are disclosed to screen for medicaments that counteract the effects of TORSIN1A mutation.

BACKGROUND

Primary dystonia is a non-degenerative neurological orphan disease with limited treatment options and characterized by disabling involuntary twisting movements and postures. It is the third most common neurological movement disorder. Primary dystonia lacks an identifiable structural or biochemical cause and occurs from a normally appearing central nervous system. There is no cure for primary dystonia and most patients are symptomatically treated by peripheral administration of Botulinum toxin to prevent muscle hyperactivation or deep brain stimulation that modifies basal ganglia rhythmicity via electrodes implanted into the globus pallidus. There is thus a very high need to develop causative and more effective treatment options. Primary dystonia, the most common form of dystonia, is typically categorized according to age at onset (Tanabe et al 2009). This feature is tightly correlated with the body part initially affected, as well as the underlying cause and likelihood of spread. Early-onset (childhood, <20 years) dystonia is typically dominantly inherited, often begins in the arm or leg, and can spread widely, resulting in severe motor disability. By contrast, late-onset (adult, >20 years) dystonia is usually idiopathic, begins in the face or neck, and is less likely to spread to surrounding body parts (Tanabe et al 2009).

The most studied genetic form of dystonia is DYT1 dystonia, a form of primary early-onset dystonia caused by a one amino acid deletion in the TORSIN1A gene. While the latter TORSIN1A mutation is the most common cause of childhood-onset dystonia, it can also predispose patients to—or alter the severity of —adult-onset primary dystonia (Tanabe et al 2009). Although there is a firm link between the disease and loss of TORSIN activity (Goodchild et al., 2005; Liang et al., 2014; WO1998057984; US20070212333), this information has not yet been translated to dystonia therapy because TORSIN1A function is insufficiently understood. It would thus be advantageous to understand the role of TORSIN1A in order to develop new and innovative therapies for DYT1 dystonia.

TORSINS are animal-specific proteins and members of the functionally diverse AAA+ ATPase family (Hanson and Whiteheart, 2005; Vander Heyden et al., 2011). Many studies show that they concentrate and appear to function in the nuclear envelope (NE) (Goodchild et al., 2015; Goodchild and Dauer, 2005; Kim et al., 2010; Sosa et al., 2014), a specialized endoplasmatic reticulum (ER) subdomain. Mammals have four TORSIN genes with different tissue expression patterns (Jungwirth et al., 2010). To examine which cell types depend on TORSIN activity for development, we took advantage of the well-known fly model, *Drosophila melanogaster* that has a single Torsin (dTorsin) gene (Jokhi et al., 2013; Wakabayashi-Ito et al., 2011). Surprisingly, this revealed a previously unrecognized role for Torsin in the regulation of cellular lipid metabolism. More precisely this application discloses that dTorsin controls the phosphatidic acid (PtdA) phosphatase (PAP) activity of Lipin. Lipin (homologues PAH1 or SMP2 in yeast) controls membrane abundance, membrane composition and storage lipid production by catalyzing the conversion of PtdA into diacylglycerol (DAG). Lipin is activated by an inner nuclear membrane (INM)-localized phosphatase complex, and shuttles between the nucleus and cytosol thanks to a nuclear localization sequence (NLS) (Han et al., 2012; Harris et al., 2007; Peterfy et al., 2001; Peterson et al., 2011). The stimulated production of the energy storing lipid triacylglycerol (TAG) by Lipin is counteracted by the phosphocholine cytidylyltransferase (Cct) enzyme that is rate limiting for phophatidylcholine (PtdCho) synthesis. Cct also contains a NLS and while Lipin drives energy storage, Cct steers membrane synthesis from the INM (Cornell and Ridgway, 2015; Lagace and Ridgway, 2005).

The data described in this application establishes for the first time that Torsins regulate cellular lipid metabolism. Although both TORSIN and LIPIN have been linked separately to inner nuclear membrane composition (Goodchild et al., 2015; Goodchild and Dauer, 2005; Kim et al., 2010; Sosa et al., 2014; Han et al., 2012; Harris et al., 2007; Peterfy et al., 2001; Peterson et al., 2011), to the best of our knowledge there is no direct link known or ever suggested between TORSIN and LIPIN. LIPIN has been disclosed as target for the prophylaxis and treatment of diabetes mellitus, arteriosclerosis, muscular dystrophy, heart attack and stroke (EP1571157) but no connection between LIPIN and dystonia has been disclosed.

SUMMARY

This invention describes that the developmentally essential, animal-specific TORSIN AAA+ proteins are previously unrecognized regulators of cellular lipid metabolism. Applicants demonstrate that TORSINS control lipid levels in vivo and, via live-cell imaging, find a relationship between human TORSIN1A localizing in the inner nuclear membrane, rapid expansion of the nuclear membranes, and increased membrane lipid levels. Applicants further establish that *Drosophila* Torsin (dTorsin) regulates the step of lipid metabolism controlled by the Lipin enzyme and that the DYT1 dystonia causative mutation of dTorsin leads to hyperactivation of Lipin. Surprisingly it could be demonstrated that genetic suppression of Lipin rescues the dTorsin loss-of-function defects both in fly and mice. Interestingly, also in the disease accurate Tor1a$^{+/\Delta gag}$ mice mutant hyperactivation of LIPIN could be demonstrated. Moreover, by reducing LIPIN activity both nuclear membrane defects in neuronal cells of the severe Tor1a$^{-/-}$ and Tor1a$^{\Delta gag/\Delta gag}$ mutant mice could be reduced as well as the lifespan of the Tor1a$^{+/\Delta gag}$ mutant mice could be increased.

It is an object of the invention to provide an inhibitor of functional expression of LIPIN for use in treatment of neurological diseases, wherein said inhibitor is selected from a gapmer, a shRNA, a siRNA, a CRISPR-Cas, a CRISPR-C2c2, a TALEN, a Zinc-finger nuclease, an antisense oligomer, a miRNA, a morpholino, a locked nucleic acid, a peptide nucleic acid, ribozyme or a meganuclease.

More particularly said inhibitor of functional expression of LIPIN is provided for use in treatment of dystonia, more particularly for use in treatment of primary dystonia, even more particularly for use in treatment of early-onset dystonia, most particularly for use in treatment of DYT1 primary dystonia. Even more particularly said LIPIN is LIPIN. The LIPIN gene as used herein is the nucleic acid sequence that encodes one of the four human LIPIN1 isoforms specified by SEQ ID No 1 to 4. The cDNA and protein reference sequences in NCBI from homologues of LIPIN1 in Mus musculus are NM_001130412.1 and NP_001123884.1, NM_015763.4 and NP_056578.2, NM_172950.3 and NP_766538.2.

Another aspect of the invention provides a pharmaceutical composition for use in treatment of neurological diseases, wherein said pharmaceutical composition comprises an inhibitor of functional expression of LIPIN and wherein said inhibitor of functional expression of LIPIN is selected from a gapmer, a shRNA, a siRNA, a CRISPR-Cas, a CRISPR-C2c2, a TALEN, a Zinc-finger nuclease, an antisense oligomer, a miRNA, a morpholino, a locked nucleic acid, a peptide nucleic acid, ribozyme or a meganuclease. According to particular aspects, said pharmaceutical composition is provided for use in treatment of dystonia, primary dystonia, early-onset dystonia or DYT1 primary dystonia. Even more particularly said LIPIN is LIPIN1.

Another aspect of the invention provides screening methods to produce an inhibitor of functional expression of LIPIN, comprising determining the storage lipid levels of Torsin knock-out cells in an in vitro cell culture set up; administering a test compound to said Torsin knock-out cells; wherein, a reduction in said storage lipid levels of at least 10% compared to a condition wherein no test compound was administered, identifies said test compound as an inhibitor of functional expression of LIPIN. In more particular aspects said Torsin is Torsin1A specified by SEQ ID No 5 that encodes the protein of SEQ ID No 6. The cDNA and protein reference sequences in NCBI from homologues of Torsin1A in Mus musculus and in Drosophila melanogaster are NM_144884 and NP_659133 (M. musculus) and NM_131950 and NP_572178 (D. melanogaster). In even more particular aspects said LIPIN is LIPIN. In a particular embodiment, the cells used in said screening methods are not human embryonic stem cells and/or are not human cells derived from human embryos. In an even more particular embodiment, the cells used in the screening methods described in this application are not human. In even more particular embodiment, said in vitro cell culture consists of mice or fly cells.

According to another aspect of the invention, screening methods are provided to produce a compound for use in the treatment of dystonia, comprising determining the storage lipid levels and/or cell size of Torsin knock-out cells in an in vitro cell culture set up; administering a test compound to said Torsin knock-out cells; wherein, a reduction in said storage lipid levels of at least 10% and/or an increase in cell size of at least 10% compared to a condition wherein no test compound was administered, identifies said test compound as a compound for use in the treatment of dystonia. In more particular aspects said Torsin is Torsin1A. In a particular embodiment, the cells used in said screening methods are not human embryonic stem cells and/or are not human cells derived from human embryos. In an even more particular embodiment, the cells used in the screening methods described in this application are not human. In even more particular embodiment, said in vitro cell culture consists of mice or fly cells.

According to another aspect, a screening method is provided to produce a compound for use in the treatment of dystonia, said method comprising expressing a human hyperactivated LIPIN in yeast; administering a test compound to said yeast; identifying said test compound as a compound for use in the treatment of dystonia if the growth of said yeast in the presence of said test compound is at least 10% higher than the growth of said yeast in the absence of said test compound. In a particular embodiment said LIPIN is LIPIN1.

According to yet another aspect of the invention, a method is disclosed to produce a pharmaceutical composition comprising a compound identified by the screening methods disclosed in this application.

BRIEF DESCRIPTION OF THE FIGURES

The patent or application file contains at least one drawing executed in color, Copies of this patent or patent application publication with color drawing(s) will be provided by the Office upon request and payment of the necessary fee.

A-B) Schematic representation of the domain organization of (A) human TORSIN and TORSIN activator proteins and (B) fly Torsins and Torsin activator proteins. We also show the site of the mGFP tag for fusion proteins used in this study. The position of catalytically required glutamate (E; torsins) and arginine (R; activators) are also highlighted. Numbering refers to the NM_000113 sequence for human TORSIN1A, NM_015602 for human LAP1 and NM_145034 for human LULL1. Fly Torsin refers to NM_131950 and fly CG14103 (dLAP1) is NM_140892. C) Internal nuclear membranes are absent from a cell with ER-localized TORSIN1A-mGFP at 9 hours after inducing LULL1 expression. 3D-SEM through the nucleus of a cell where light microscopy (C') detected ER-localized TORSIN1A that had not yet relocalized to the INM. The individual panels show a z-stack of images at 500 nm intervals. Scale bar shows 1 μm. D) Relative amounts of PtdCho (PC) species in control cells, and cells with TORSIN1A-driven membrane proliferation. Columns show the average % that each individual PtdCho molecule makes up of total cellular PtdCho in control U2OS cells (grey column), TORSIN1A-mGFP expressing cells without LULL1 expression (black column), and TORSIN1A-mGFP expressing cells after 11 hours of tetracycline treatment (red column).

Figure 6:
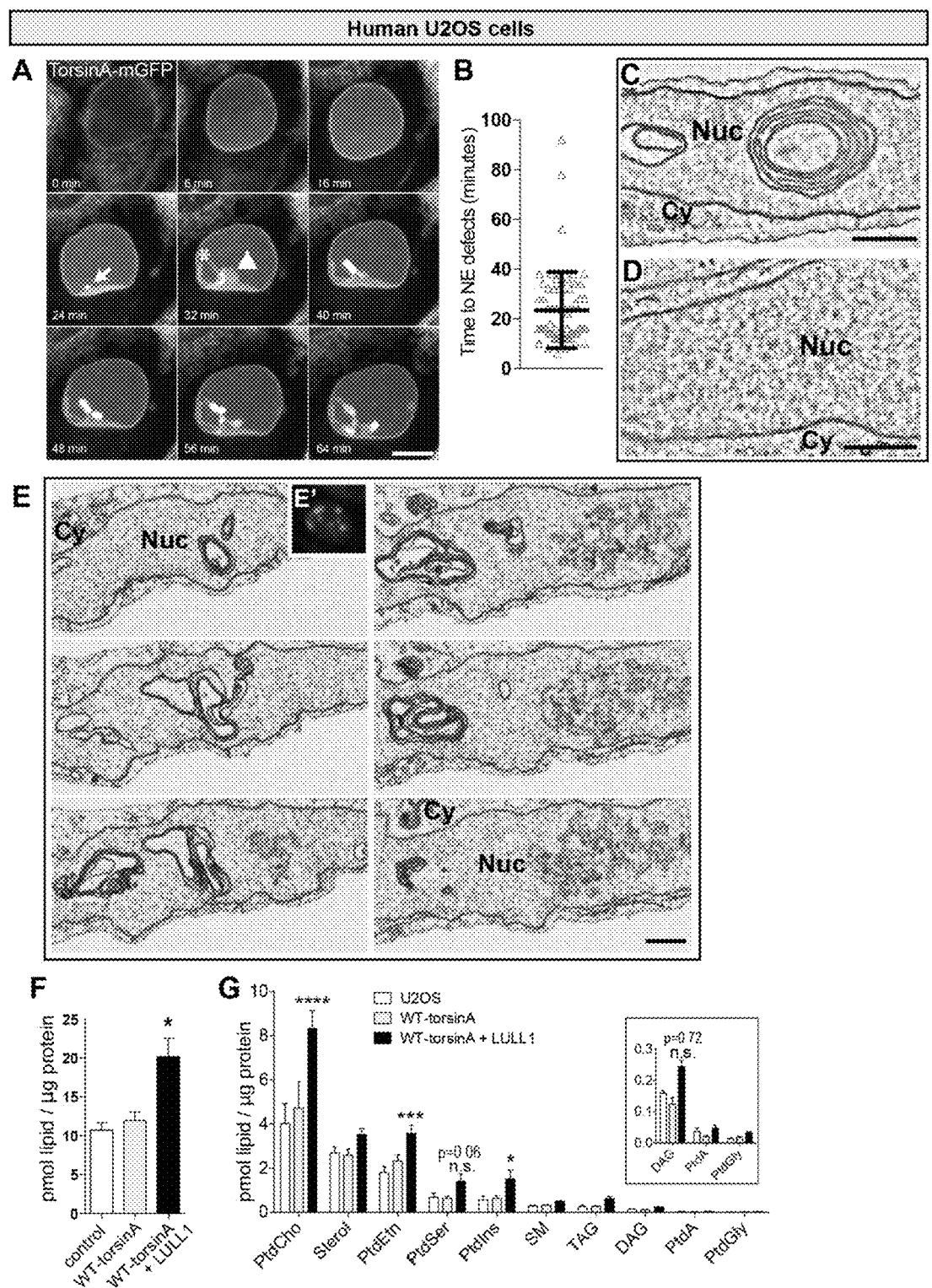

FIG. 6. TORSIN1A in the INM induces membrane proliferation and increases cellular lipid levels.

A) TORSIN1A-mGFP re-localization to the INM produces membrane tubules and sheet-like structures. Panels show TORSIN1A-GFP signal in U2OS cells induced to express LULL1 (not shown). T=0 min is the first time-point when TORSIN1A is in the INM, and images continue for 64 minutes in 8 minute intervals. White arrow highlights the first sign of membrane changes, the asterisk points to tubules, and the arrowhead indicates sheet-like structures. Scale bar shows 10 μm. B) Membrane defects appear rapidly after TORSIN1A-mGFP concentrates in the INM. Bars show the mean±SD of the time between TORSIN1A-mGFP re-localizing to the INM and the appearance of nuclear membrane distortions. Points show the time for individual cells. C & D) INM-localized TORSIN1A-mGFP produces intra-nuclear double membrane structures. TEM of the nucleus (Nuc) of TORSIN1A-mGFP expressing cells after C) 9 hours of tetracycline-induced LULL1 expression or D) no tetracycline. (Cy) cytosol. Scale bars show 1 μm. E) 3D-SEM reveals nuclear membrane stacks in a cell where light microscopy (E') shows distorted nuclear membranes. The individual panels show a z-stack of images at 500 nm intervals. Scale bar shows 1 μm. F-G) TORSIN1A increases cellular lipids, predominantly elevating PtdCho and PtdEtn. Columns show lipid/protein (mean±sem) extracted from a control U2OS cell line (white), TORSIN1A-mGFP expressing cells without LULL1 expression (grey), and TORSIN1A-mGFP expressing cells after 11 hours of tetracycline treatment (black column). Values come from 3 independent experiments. (F) One-Way ANOVA; *$p<0.05$. (G) Two-Way ANOVA; *$p<0.05$, *$p<0.001$, **$p<0.0001$; (PtdSer) phosphatidylserine; (SM) sphingomyelin.

Figure 7:
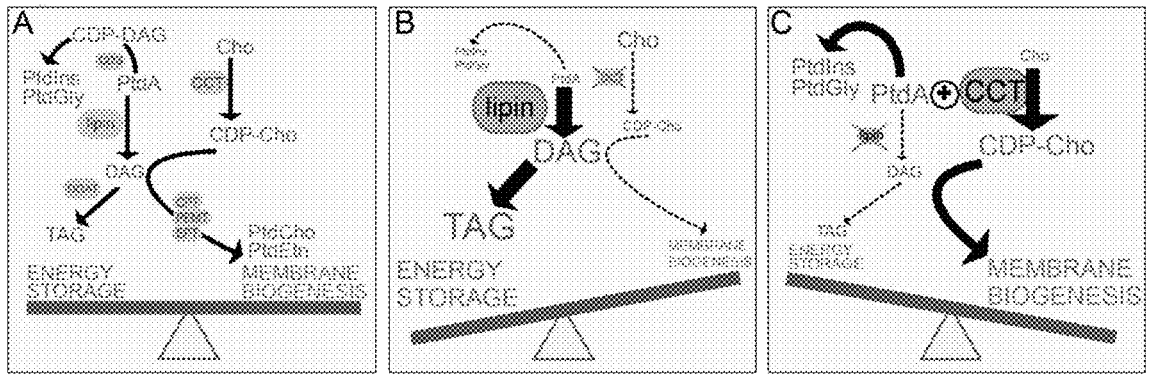

FIG. 7. Cellular lipid metabolism pathways.

A) Simplified diagram of cellular lipid metabolism. Only key enzymes (grey circles) and metabolites (purple) are highlighted. B-C) Lipin produces DAG from PtdA as the penultimate step in TAG synthesis. Lipin can be rate limiting for storage lipid production (Han et al., 2006; Ugrankar et al., 2011), and negatively regulates PtdA-derived lipids like PtdIns and PtdGly (Bahmanyar et al., 2014). CCT is rate limiting for PtdCho production and therefore bulk membrane lipid synthesis (Cornell and Ridgway, 2015; Hermansson et al., 2011). PtdA stimulates CCT, highlighted by +symbol, and through this lipin negatively regulates membrane lipid levels (Craddock et al., 2015). (CCT) CTP: Phosphocholine Cytidylyltransferase; (CDP) cytidine diphosphate; (Cho) choline; (CDS) PtdA Cytidylyltransferase; (CPT) CDP choline: 1,2-diacylglycerol cholinephosphotransferase; (DAG) diacylglycerol; (DGAT) Diglyceride acyltransferase; (EPT) CDP-Ethanolamine:DAG ethanolamine phosphotransferase; (PEMT) phosphatidylethanolamine N-Methyltransferase; (PtdA) phosphatidic acid; (PtdCho) phosphatidylcholine; (PtdEtn) phosphatidylethanolamine; (PtdGly) phosphatidyglycerol; (PtdIns) phosphatidylinositol; (TAG) triacylglycerol.

Figure 8:
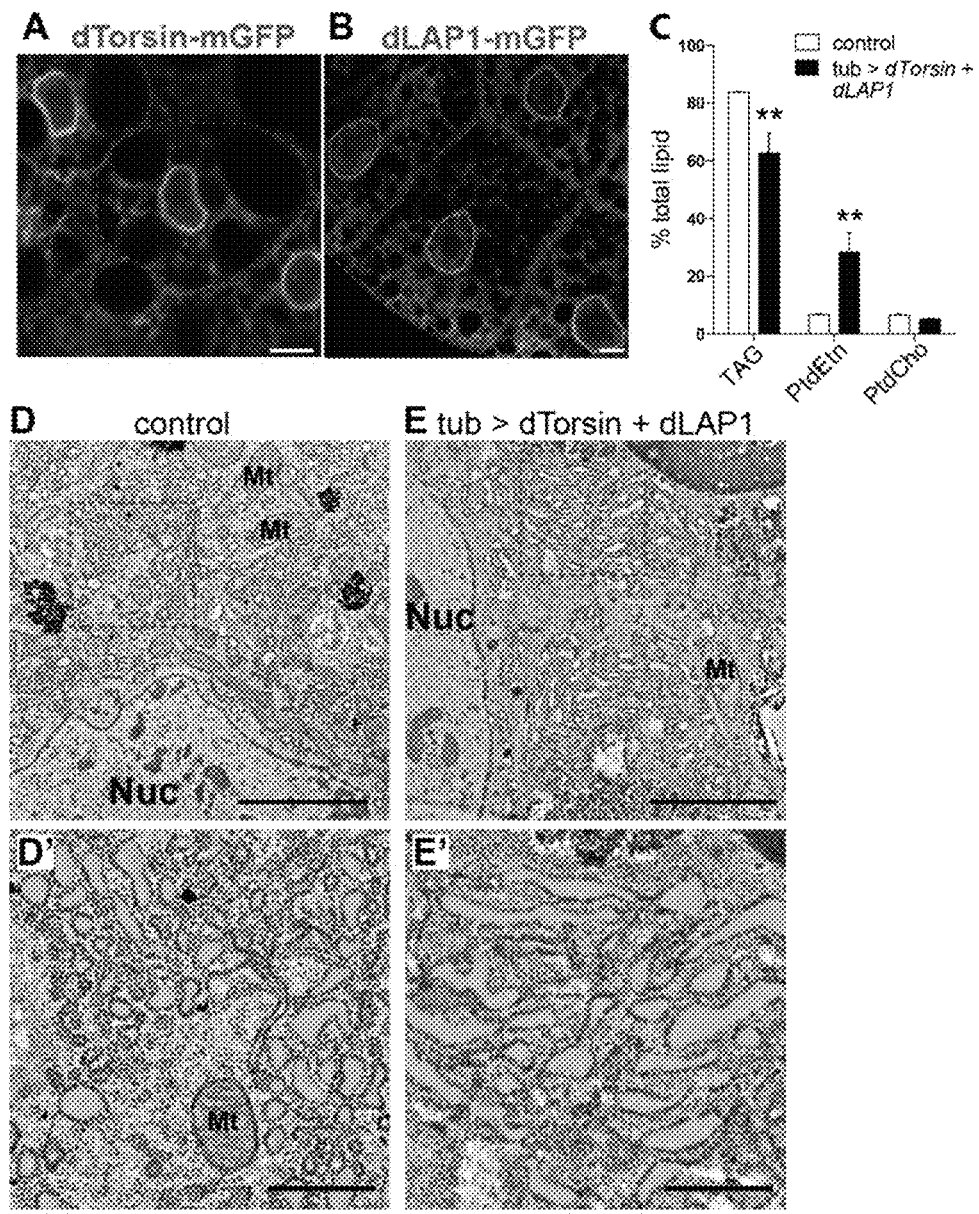

FIG. 8. dTorsin and dLAP1 co-overexpression suppress TAG and increase membrane lipids.

A-B) Confocal images of dTorsin-mGFP and dLAP1-mGFP in fat body cells expressed using the tub-GAL4 driver. Scale bars show 10 μm. C) Co-overexpression of dTorsin and dLAP1 reduces TAG and elevates PtdEtn. Columns show the mean±sem of the % of lipid classes within the 5-day-old fat body lipidome of controls (white), and upon co-expression of dTorsin-mGFP and dLAP1-mGFP (black). Measurements are made from 3 independent sets of 8 fat bodies (N=24) (Two-Way ANOVA; **p<0.01). D-E) Small tubular ER structures in (D) a control fat body cell while (E) the ER appears as distended sheets in cells co-expressing dTorsin-mGFP and dLAP1-mGFP. Representative TEM images showing ER morphology after assessing >10 cells in 3 wandering stage larvae. Dashed red lines show area enlarged in D' and E' and blue shading highlights ER structures. (Mt) mitochondrion. Scale bars show (D & E) 2 μm, (D' & E') 0.5 μm.

Figure 9:
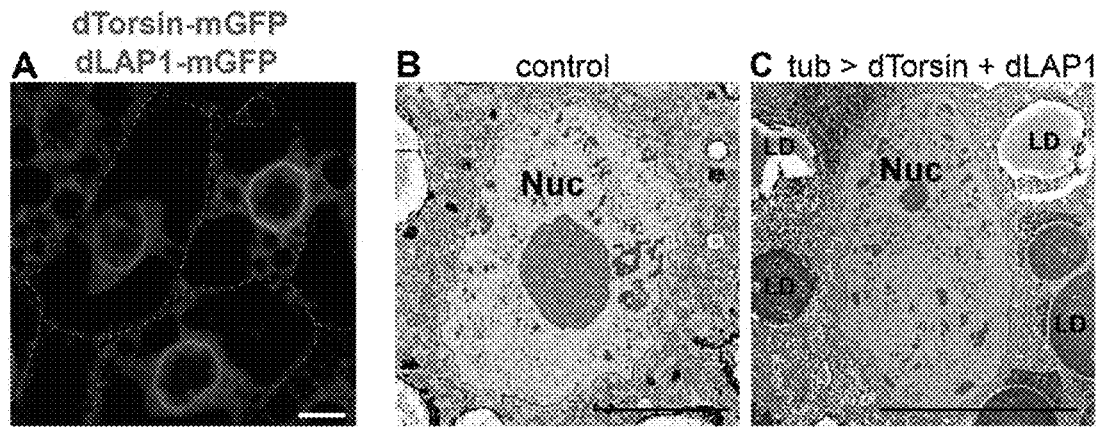

FIG. 9. Nuclear membrane ultrastructure appears unaltered in cells co-expressing dTorsin and dLAP1.

A) Confocal image of GFP signal in wandering stage fat body cells co-expressing dTorsin-mGFP and dLAP1-mGFP via UAS coupled cDNAs and the tub-GAL4 driver. Scale bar shows 10 μm. B-C) TEM of wandering stage fat body cell ultrastructure from (B) a control larvae and (C) a larvae with tub-GAL4 driven expression of UAS-dTorsin-mGFP and UAS-dLAP1-mGFP. (LD) lipid droplet; (Nuc) nucleus. Scale bars show 5 μm.

Figure 10:
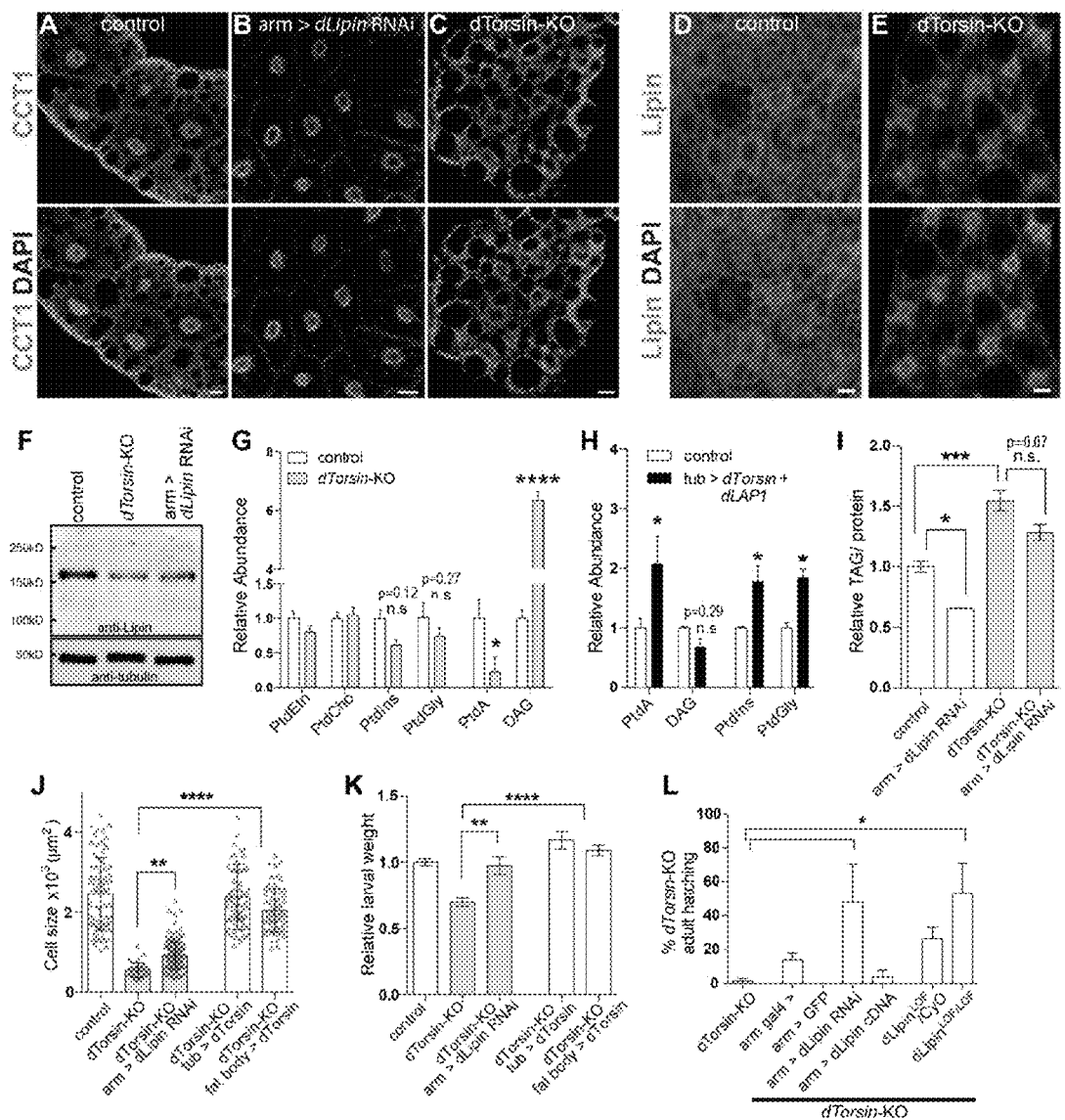

FIG. 10. dTorsin regulates Lipin activity

A-F) Lipid metabolizing enzymes in the late stage fat body. A-C) Confocal images of anti-CCT1 labeled fat body from (A) control larvae, (B) larvae expressing dLipin RNAi, and (C) dTorsin-KO larvae. D) anti-lipin labeling of control and (E) dTorsin-KO fat cells. Scale bars show 10 μm. F) Lipin protein levels in fat body lysates from control, dTorsin-KO, and dLipin RNAi expressing larvae. G-H) dTorsin regulates levels of the lipin substrate, PtdA, and product, DAG. G) Columns show the mean±sem of the relative abundance of lipid classes within the 5-day-old control and dTorsin-KO lipidome, measured from three independent sets of ten fat bodies (N=30). H) dTorsin and dLAP1 co-expression elevate the abundance of PtdA, PtdIns and PtdGly detected in three sets of eight fat bodies (N=24). (Two-Way ANOVA; *p<0.05, ****p<0.0001). I- L) dLipin loss rescues dTorsin-KO defects. 1) dLipin RNAi suppresses TAG levels in N>28 pooled 3-day-old larvae. Bars show mean±SEM. J) dLipin RNAi increases the size of dTorsin-KO fat body cells and (K) increases the weight of dTorsin-KO larvae. Bars show the mean±SD of measures from 5-day-old control, dTorsin-KO, and dTorsin-KO animals that express dLipin RNAi with the arm-GAL4, dTorsin cDNA with tub-GAL4 or fat-body (r4-GAL4) drivers. J) Points show individual cell sizes in (N≥4) 5-day-old larvae. K) Measurements were made from >4 sets of ten wandering stage larvae (N≥40 animals). L) dLipin suppression increases the survival of dTorsin-KO animals. Bars show the mean±sem of the percentage of dTorsin-KO that hatch as adults. dLipinLOF refers to the dLipinKG00562 allele (One-Way ANOVA; *p<0.05, p<0.01, *p<0.001, ****p<0.0001).

Figure 11:
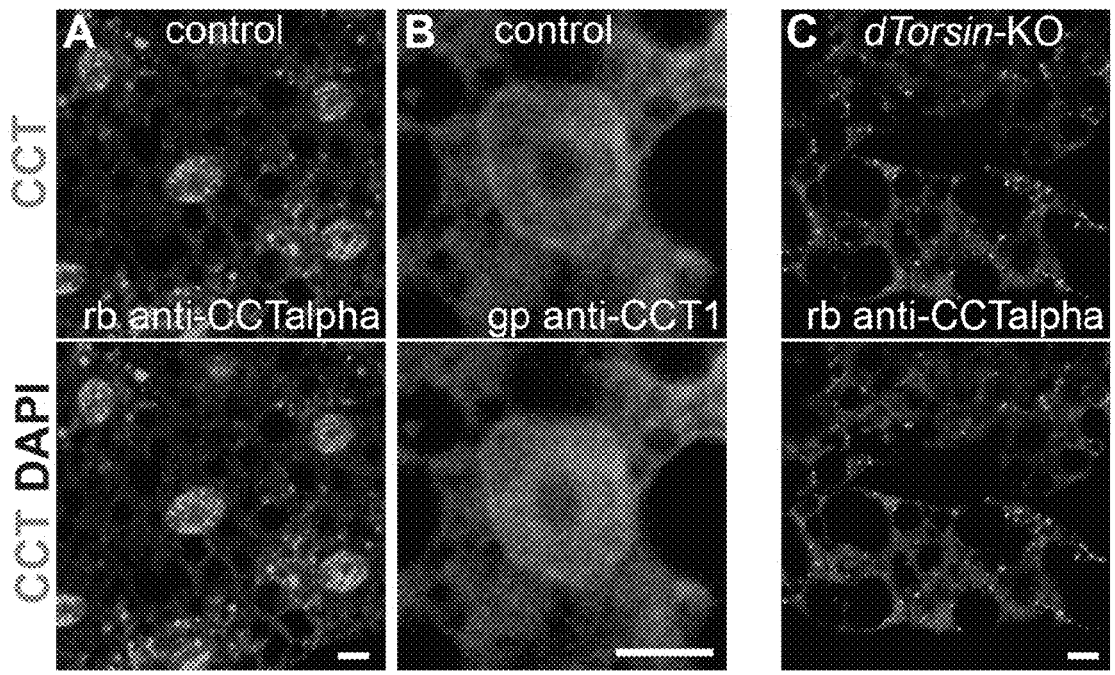

FIG. 11. Nuclear and NE localized anti-CCT immunoreactivity is lost from dTorsin-KO fat cells.

(A-B) Confocal images of control fat body cells labeled with (A) anti-CCTalpha and (B) anti-CCT1. Both antibodies detect nuclear localized antigen, and (B) the antibody against fly CCT1 also shows NE-localized signal in some cells. (C) nuclear anti-CCTalpha signal is absent from dTorsin-KO fat body cells. Scale bars show 10 μm.

Figure 12:
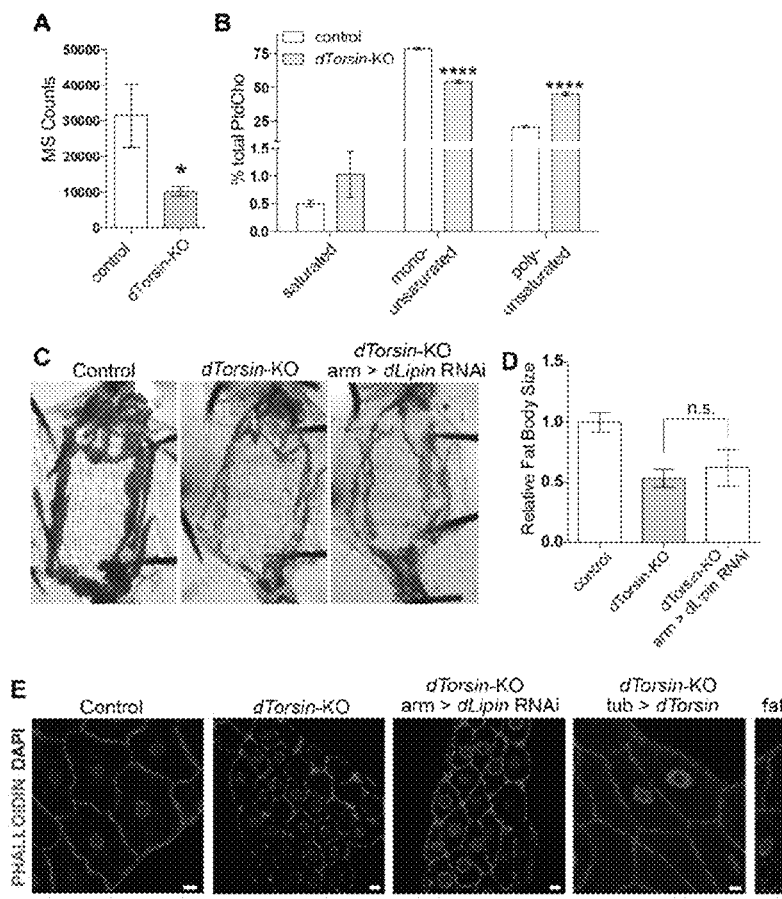

FIG. 12. dTorsin regulates fat body lipid homeostasis

A) Total number of lipid molecules detected by mass spectrometry of control and dTorsin-KO fat body samples. Tissue was dissected in PBS, and individual fat bodies pooled in 150 mM ammonium bicarbonate. Bars show the mean±sem of measurements from three sets of ten fat bodies (n=30) (t-Test; *p<0.05). B) dTorsin loss alters the saturation profile of PtdCho lipids detected by mass spectrometry. Bars show the mean±sem of measurements from 3 sets of 10 fat bodies (n=30) (Two-Way ANOVA; ****p<0.0001). C & D) dTorsin-KO fat body remains small in animals expressing dLipin RNAi. C) Brightfield images and (D) graph showing the mean±sem of the relative fat body size of control, dTorsin-KO and the dTorsin-KO with dLipin RNAi driven by arm-GAL4. (One-way ANOVA followed by Tukey's test; n.s: not significant). E) dLipin RNAi increases the size of dTorsin-KO fat cells. Confocal images of fat body from control, dTorsin-KO, dTorsin-KO with arm-GAL4 expressed dLipin RNAi, and dTorsin-KO with ubiquitous (tub-GAL4) or fat body (r4-GAL4) dTorsin cDNA expression. Scale bars show 10 μm.

Figure 13:
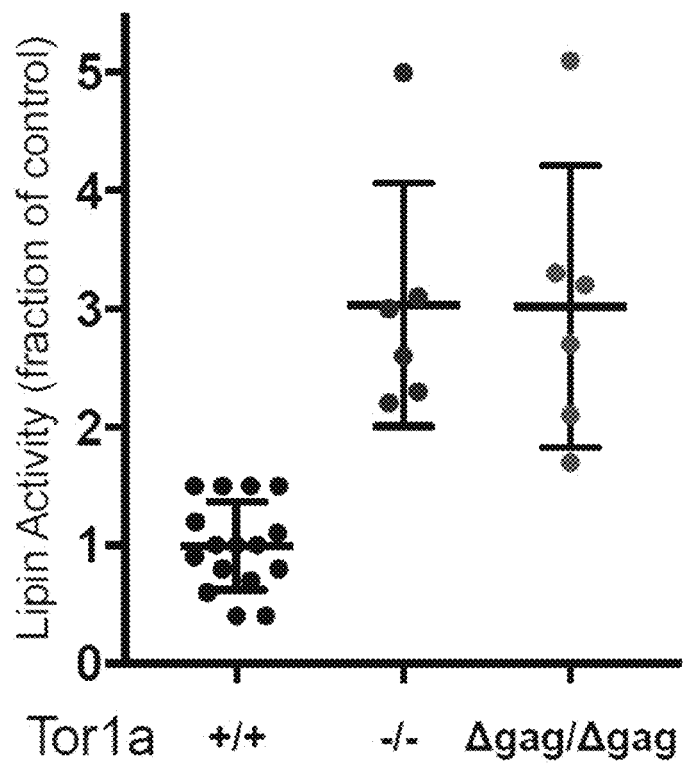

FIG. 13. Elevated PAP activity in Torsin1a mutant embryonic mouse brains.

PAP activity or PtdA conversion to DAG is biochemically measured in 4 control (wild-type and Tor1a$^{+/-}$) and 4 Tor1a$^{-/-}$ and 4 Tor1a$^{\Delta gag/\Delta gag}$ knock-out embryonic (E18) mouse brains. We detect significantly elevated PAP activity (One-Tailed T-Test), which is completely in line with the model developed in *Drosophila*.

Figure 14:
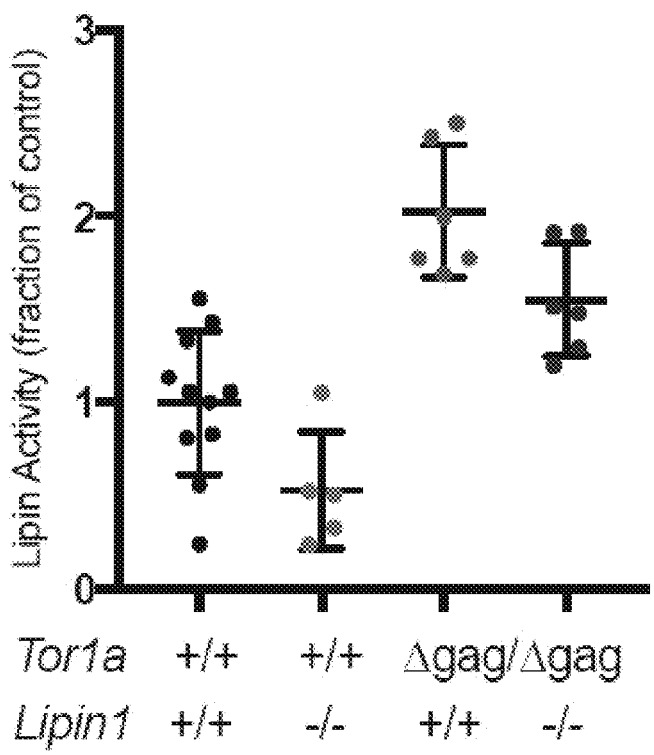

FIG. 14. Lipin1 knock-out reduces LIPIN activity in wild-type and Tor1a mutants.

Compared to wild-type mice (Tor1a$^{+/+}$ Lipin1$^{-/-}$), LIPIN activity is significantly reduced in Lipin1$^{-/-}$ mutant mice and as well as in Tor1a$^{\Delta gag/\Delta gag}$ mutant mice.

Figure 15:
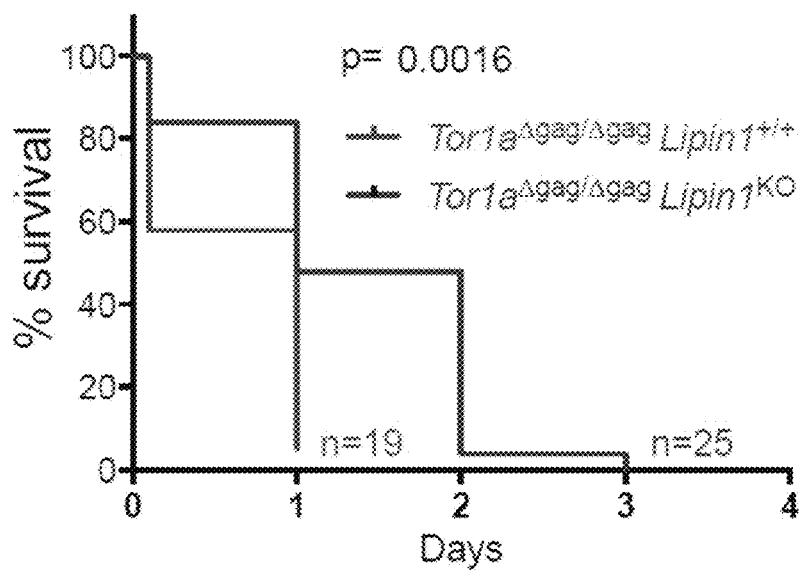

FIG. 15. Lipin1 knock-out increases survival of Tor1a mutant mice.

The life-span of Tor1a$^{\Delta gag/\Delta gag}$ Lipin1$^{-/-}$ (n=25) mice was significantly increased compared to Tor1a$^{\Delta gag/\Delta gag}$ mice with a functional Lipin1 (n=19) (p=0.0016).

Figure 16:
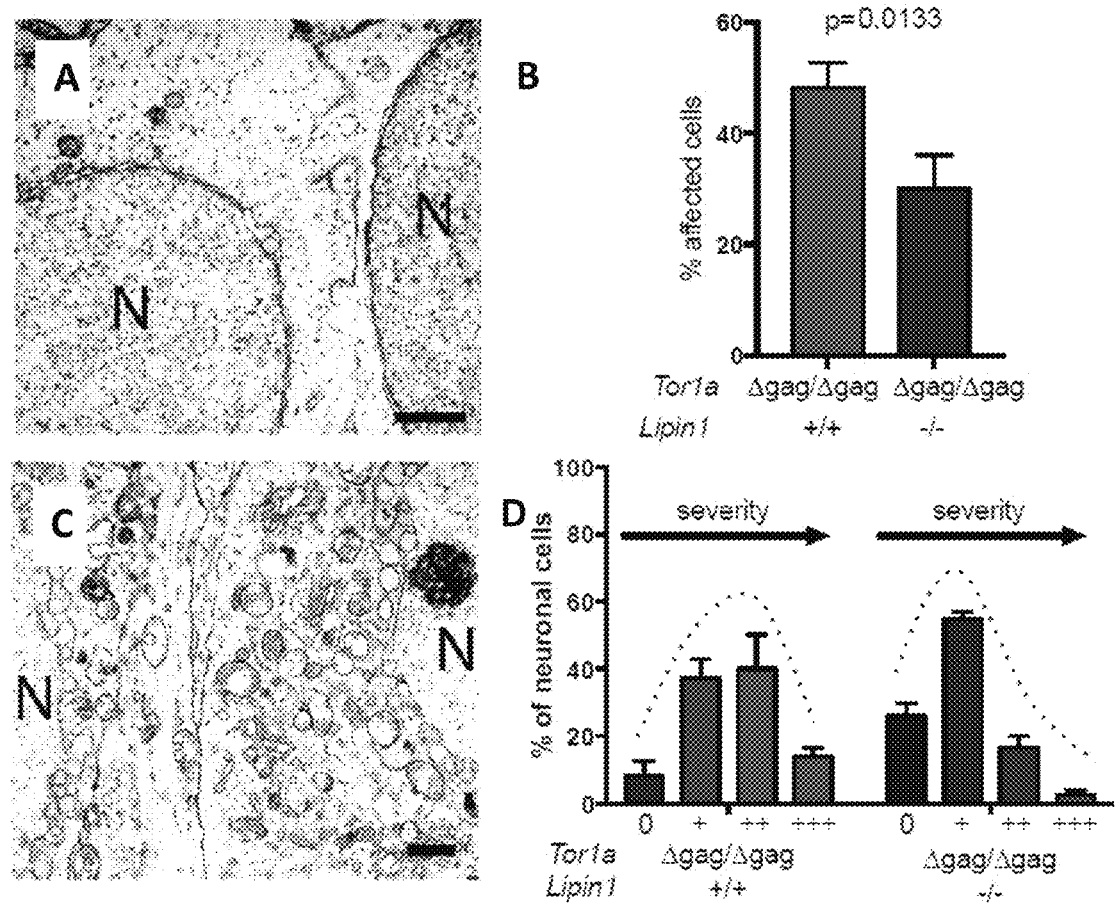

FIG. 16. Nuclear membrane defects in Tor1a mutant mice brain neurons are decreased when Lipin expression is reduced.

A-B. In the mildly affected CNS zone 1 of Tor1a$^{\Delta gag/\Delta gag}$ mice brains, Lipin1 knock-out significantly reduces the number of cells with affected nuclear membranes (p=0.0133). C-D. In the moderately affected CNS zone 2 the severity of affected neurons in Tor1a$^{\Delta gag/\Delta gag}$ mutant mice brains is reduced (0 (p=0.018); +(p=0.018); ++(p=0.019); +++(p=0.001)).

Figure 17:
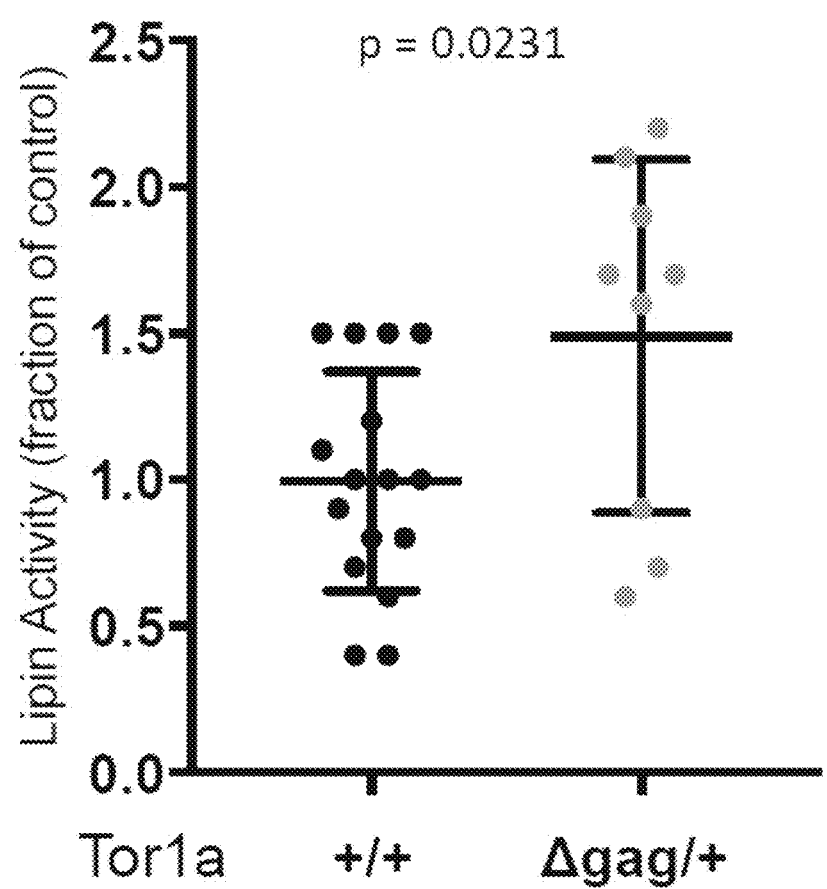

FIG. 17. LIPIN activity is increased in the disease accurate Tor1a mice model.

In the brains of genetically accurate Tor1a$^{\Delta gag/+}$ DYT1 mice LIPIN activity was significantly elevated (p=0.021). Note that the PAP activity of Tor1a$^{\Delta gag/+}$ animals has a wider than normal variance, which might explain the partial penetrance of this genotype in driving dystonia in humans.

DETAILED DESCRIPTION

Definitions

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 4th ed., Cold Spring Harbor Press, Plainsview, N.Y. (2012); and Ausubel et al., current Protocols in Molecular Biology (Supplement 100), John Wiley & Sons, New York (2012), for definitions and terms of the art. The definitions provided herein should not be construed to have a scope less than understood by a person of ordinary skill in the art.

In the application, genes and proteins are named according to the international agreements. Human gene symbols generally are italicised, with all letters in uppercase (e.g. TOR1A). Protein designations are the same as the gene symbol, but are not italicised, with all letters in uppercase (e.g. LIPIN) (world wide web at genenames.org/about/overview). In mice and rats, gene symbols generally are italicised, with only the first letter in uppercase and the remaining letters in lowercase (e.g. Tor1a). Protein designations are the same as the gene symbol, but are not italicised and all are upper case (e.g. LIPIN) (world wide web at informatics.jax.org/mgihome/nomen/gene.shtml). Fly gene names and symbols begin with an uppercase letter and are italicized (e.g. dTorsin). Symbols for proteins begin also with an upper-case letter but are not italicized (e.g. dLipin) (flybase.org).

Since several years it is known that a loss-of-function mutation in the TORSIN1A gene is causative to the DYT1 dystonia neurological disease. In this application it is shown that fly dTorsin reduces triglycerides and elevates membrane lipids in adipose tissue. The key lipid metabolizing enzyme, Lipin, is mislocalized in dTorsin-KO cells, and dTorsin increases the Lipin substrate, phosphatidate, while reducing the product, diacylglycerol. Applicants also disclose that inhibition of functional expression of dLipin rescues the developmental defects of dTorsin loss. Finally, Applicants also associate human TORSIN1A activity with increased membrane lipid levels, demonstrate hyperactivity of LIPIN in a genetically accurate murine disease model and rescued a severe murine dystonia disease model by knocking-out Lipin1. All the findings described in this application clearly identify TORSINS as essential regulators of cellular lipid metabolism and furthermore show the role of disturbed lipid biology in DYT1 dystonia.

Thus in a first aspect, the application provides an inhibitor of functional expression of LIPIN for use in treatment of neurological diseases, wherein said inhibitor is selected from a gapmer, a shRNA, a siRNA, a CRISPR-Cas, a CRISPR-C2c2, a TALEN, a Zinc-finger nuclease, an antisense oligomer, a miRNA, a morpholino, a locked nucleic acid, a peptide nucleic acid, ribozyme or a meganuclease. In one embodiment, said inhibitor is provided for use in treatment of a neurological disease selected from dystonia, primary dystonia, early-onset dystonia, DYT1 primary dystonia. In other particular embodiments, the invention provides an inhibitor of functional expression of LIPIN1 for use in treatment of neurological diseases, wherein said inhibitor is selected from a gapmer, a shRNA, a siRNA, a CRISPR-Cas, a CRISPR-C2c2, a TALEN, a Zinc-finger nuclease, an antisense oligomer, a miRNA, a morpholino, a locked nucleic acid, a peptide nucleic acid, ribozyme or a meganuclease. In even other particular embodiments, said inhibitor is provided for use in treatment of a neurological disease selected from dystonia, primary dystonia, early-onset dystonia, DYT1 primary dystonia. This is equivalent as saying that methods of treating neurological diseases in a subject in need thereof are provided, comprising administering an inhibitor of functional expression of LIPIN or LIPIN1 to said subject. In particular embodiments, said neurological disease is selected from dystonia, primary dystonia, early-onset dystonia, DYT1 primary dystonia. Throughout current application, the nature of the inhibitor is not vital to the invention, as long as it inhibits the functional expression of the LIPIN or LIPIN1 gene. According to specific embodiments, the inhibitor is selected from the inhibitory RNA technology (such as a gapmer, a shRNA, a siRNA, an antisense oligomer, a miRNA, a morpholino, a locked nucleic acid, peptide nucleic acid), a CRISPR-Cas, a CRISPR-C2c2, a TALEN, a meganuclease or a Zinc-finger nuclease.

With "functional expression" of LIPIN or LIPIN, in the present invention it is meant the transcription and/or translation of functional gene product. For protein coding genes like LIPIN, "functional expression" can be deregulated on at least three levels. First, at the DNA level, e.g. by removing or disrupting the LIPIN gene, or by preventing transcription to take place (in both instances preventing synthesis of the relevant gene product, i.e. LIPIN or LIPIN). The lack of transcription can e.g. be caused by epigenetic changes (e.g. DNA methylation) or by loss-of-function mutations. A "loss-of-function" or "LOF" mutation as used herein is a mutation that prevents, reduces or abolishes the function of a gene product as opposed to a gain-of-function mutation that confers enhanced or new activity on a protein. LOF can be caused by a wide range of mutation types, including, but not limited to, a deletion of the entire gene or part of the gene, splice site mutations, frame-shift mutations caused by small insertions and deletions, nonsense mutations, missense mutations replacing an essential amino acid and mutations preventing correct cellular localization of the product. Also included within this definition are mutations in promoters or regulatory regions of the LIPIN gene if these interfere with gene function. A null mutation is an LOF mutation that completely abolishes the function of the gene product. A null mutation in one allele will typically reduce expression levels by 50%, but may have severe effects on the function of the gene product. Note that functional expression can also be deregulated because of a gain-of-function mutation: by conferring a new activity on the protein, the normal function of the protein is deregulated, and less functionally active protein is expressed. Vice versa, functional expression can be increased e.g. through gene duplication or by lack of DNA methylation.

Second, at the RNA level, e.g. by lack of efficient translation taking place—e.g. because of destabilization of the mRNA (e.g. by UTR variants) so that it is degraded before translation occurs from the transcript. Or by lack of efficient transcription, e.g. because a mutation introduces a new splicing variant.

Third, the functional expression of LIPIN can also be inhibited at the protein level by inhibiting the function of the LIPIN protein. Non-limiting examples are intrabodies, alpha-bodies, antibodies, nanobodies, phosphatases, kinases.

In the present invention it is essential that the functional expression of LIPIN or LIPIN1 is inhibited in order to have a positive effect on the treatment of neurological diseases, more particularly dystonia, even more particularly primary dystonia, even more particularly early onset dystonia, most particularly DYT1 primary dystonia. The inhibition of the functional expression of LIPIN or LIPIN1 is preferably at least 20%, at least 30%, at least 40%, at least 50%, at least 60%, at least 70%, at least 80%, at least 90%, at least 95% or even 100%. 100% means that no detectable functional expression of LIPIN or LIPIN1 is detected. Accordingly, it is an object of the invention to provide inhibitors of functional expression of the LIPIN or LIPIN1 gene. In this application this has been fully reduced to practice by using the inhibitory RNA technology (see Example 3). Gene inactivation, i.e. inhibition of functional expression of the target gene, can be achieved through the creation of transgenic organisms expressing antisense RNA, or by administering antisense RNA to the subject (see Example 3 of the application). The nature of the inhibitor and whether the effect is achieved by incorporating antisense RNA into the subject's genome or by administering antisense RNA is not vital to the invention, as long as the inhibitor inhibits the functional expression of the LIPIN gene. An antisense construct can be delivered, for example, as an expression plasmid, which, when transcribed in the cell, produces RNA that is complementary to at least a unique portion of the cellular LIPIN RNA.

An inhibitor of functional expression of LIPIN or LIPIN1 can also be an antisense molecule or anti-gene agent that comprises an oligomer of at least about 10 nucleotides in length for which no transcription is needed in the treated subject. In embodiments such an inhibitor comprises at least 15, 18, 20, 25, 30, 35, 40, or 50 nucleotides. Antisense approaches involve the design of oligonucleotides (either DNA or RNA, or derivatives thereof) that are complementary to an RNA encoded by polynucleotide sequences of the LIPIN gene. Antisense RNA may be introduced into a cell to inhibit translation of a complementary mRNA by base pairing to it and physically obstructing the translation machinery. This effect is therefore stoichiometric. Absolute complementarity, although preferred, is not required. A sequence "complementary" to a portion of an RNA, as referred to herein, means a sequence having sufficient complementarity to be able to hybridize with the RNA, forming a stable duplex; in the case of double stranded antisense polynucleotide sequences, a single strand of the duplex DNA may thus be tested, or triplex formation may be assayed. The ability to hybridize will depend on both the degree of complementarity and the length of the antisense polynucleotide sequence. Generally, the longer the hybridizing polynucleotide sequence, the more base mismatches with an RNA it may contain and still form a stable duplex (or triplex, as the case may be). One skilled in the art can ascertain a tolerable degree of mismatch by use of standard procedures to determine the melting point of the hybridized complex. Antisense oligomers should be at least 10 nucleotides in length, and are preferably oligomers ranging from 15 to about 50 nucleotides in length. In certain embodiments, the oligomer is at least 15 nucleotides, at least 18 nucleotides, at least 20 nucleotides, at least 25 nucleotides, at least 30 nucleotides, at least 35 nucleotides, at least 40 nucleotides, or at least 50 nucleotides in length. A related method uses ribozymes instead of antisense RNA. Ribozymes are catalytic RNA molecules with enzyme-like cleavage properties that can be designed to target specific RNA sequences. Successful target gene inactivation, including temporally and tissue-specific gene inactivation, using ribozymes has been reported in mouse, zebrafish and fruitflies. RNA interference (RNAi) is a form of post-transcriptional gene silencing and used in this application as one of the many methods to inhibit or reduce the functional expression of lipin. The phenomenon of RNA interference was first observed and described in *Caenorhabditis elegans* where exogenous double-stranded RNA (dsRNA) was shown to specifically and potently disrupt the activity of genes containing homologous sequences through a mechanism that induces rapid degradation of the target RNA. Numerous reports have describe the same catalytic phenomenon in other organisms, including experiments demonstrating spatial and/or temporal control of gene inactivation, including plants, protozoa, invertebrates, vertebrates and mammals. RNAi mediated degradation of the target mRNA can be detected by measuring levels of the target mRNA or protein in the cells of a subject, using standard techniques for isolating and quantifying mRNA or protein as described in this application. The mediators of sequence-specific messenger RNA degradation are small interfering RNAs (siRNAs) generated by ribonuclease III cleavage from longer dsRNAs. Generally, the length of siRNAs is between 20-25 nucleotides (Elbashir et al. (2001) Nature 411, 494 498). The siRNA typically comprise a sense RNA strand and a complementary antisense RNA strand annealed together by standard Watson Crick base pairing interactions (hereinafter "base paired"). The sense strand comprises a nucleic acid sequence that is identical to a target sequence (i.e. the LIPIN sequence in this application) contained within the target mRNA. The sense and antisense strands of the present siRNA can comprise two complementary, single stranded RNA molecules or can comprise a single molecule in which two complementary portions are base paired and are covalently linked by a single stranded "hairpin" area (often referred to as shRNA). The siRNAs that can be used to inhibit or reduce the functional expression of lipin can comprise partially purified RNA, substantially pure RNA, synthetic RNA, or recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siRNA or to one or more internal nucleotides of the siRNA, including modifications that make the siRNA resistant to nuclease digestion. The siRNAs can be targeted to any stretch of approximately 19 to 25 contiguous nucleotides in LIPIN sequence (the "target sequence"). Techniques for selecting target sequences for siRNA are well known in the art. Thus, the sense strand of the present siRNA comprises a nucleotide sequence identical to any contiguous stretch of about 19 to about 25 nucleotides in the target mRNA. siRNAs can be obtained using a number of techniques known to those of skill in the art. For example, the siRNAs can be chemically synthesized or recombinantly produced using methods known in the art. Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Alternatively, siRNA can also be expressed from recombinant circular or linear DNA plasmids using any suitable promoter. Suitable promoters for expressing siRNA targeted against lipin activity from a plasmid include, for example, the U6 or H1 RNA pol III promoter sequences and the cytomegalovirus promoter. Selection of other suitable promoters is within the skill in the art. The recombinant plasmids of the invention can also comprise inducible or regulatable promoters for expression of the siRNA in a particular tissue or in a particular intracellular environment. The siRNA expressed from recombinant plasmids can either be isolated from cultured cell expression systems by standard techniques, or can be expressed intracellularly, e.g. in brain tissue or in neurons. siRNAs can also be expressed intracellularly from recombinant viral vectors. The recombinant viral vectors comprise sequences encoding the siRNAs of the invention and any suitable promoter for expressing the siRNA sequences. The siRNA will be administered in an "effective amount" which is an amount sufficient to cause RNAi mediated degradation of the target mRNA, or an amount sufficient to inhibit the cellular TAG lipid storage level. One skilled in the art can readily determine an effective amount of the siRNA of the invention to be administered to a given subject, by taking into account factors such as involuntary muscle contraction; the extent of the disease penetration; the age, health and sex of the subject; the route of administration; and whether the administration is regional or systemic. Generally, an effective amount of siRNAs targeting LIPIN expression comprises an intracellular concentration of from about 1 nanomolar (nM) to about 100 nM, preferably from about 2 nM to about 50 nM, more preferably from about 2.5 nM to about 10 nM. It is contemplated that greater or lesser amounts of siRNA can be administered.

Another method for the inhibition of gene expression is based on the use of shorter antisense oligomers consisting of DNA, or other synthetic structural types such as phosphorothiates, 2'-O-alkylribonucleotide chimeras, locked nucleic acid (LNA), peptide nucleic acid (PNA), or morpholinos. With the exception of RNA oligomers, PNAs and morpholinos, all other antisense oligomers act in eukaryotic cells through the mechanism of RNase H-mediated target cleavage. PNAs and morpholinos bind complementary DNA and RNA targets with high affinity and specificity, and thus act through a simple steric blockade of the RNA translational machinery, and appear to be completely resistant to nuclease attack.

Recently it has been shown that morpholino antisense oligonucleotides in zebrafish and frogs overcome the limitations of RNase H-competent antisense oligonucleotides, which include numerous non-specific effects due to the non-target-specific cleavage of other mRNA molecules caused by the low stringency requirements of RNase H. Morpholino oligomers therefore represent an important new class of antisense molecule. Oligomers of the invention may be synthesized by standard methods known in the art. As examples, phosphorothioate oligomers may be synthesized by the method of Stein et al. (1988) Nucleic Acids Res. 16, 3209 3021), methylphosphonate oligomers can be prepared by use of controlled pore glass polymer supports (Sarin et al. (1988) Proc. Natl. Acad. Sci. USA. 85, 7448-7451). Morpholino oligomers may be synthesized by the method of Summerton and Weller U.S. Pat. Nos. 5,217,866 and 5,185,444.

Another particularly form of antisense RNA strategy are gapmers. A gapmer is a chimeric antisense oligonucleotide that contains a central block of deoxynucleotide monomers sufficiently long to induce RNase H cleavage. The central block of a gapmer is flanked by blocks of 2'-O modified ribonucleotides or other artificially modified ribonucleotide monomers such as bridged nucleic acids (BNAs) that protect the internal block from nuclease degradation. Gapmers have been used to obtain RNase-H mediated cleavage of target RNAs, while reducing the number of phosphorothioate linkages. Phosphorothioates possess increased resistance to nucleases compared to unmodified DNA. However, they have several disadvantages. These include low binding capacity to complementary nucleic acids and non-specific binding to proteins that cause toxic side-effects limiting their applications. The occurrence of toxic side-effects together with non-specific binding causing off-target effects has stimulated the design of new artificial nucleic acids for the development of modified oligonucleotides that provide efficient and specific antisense activity in vivo without exhibiting toxic side-effects. By recruiting RNase H, gapmers selectively cleave the targeted oligonucleotide strand. The cleavage of this strand initiates an antisense effect. This approach has proven to be a powerful method in the inhibition of gene functions and is emerging as a popular approach for antisense therapeutics. Gapmers are offered commercially, e.g. LNA longRNA GapmeRs by Exiqon, or MOE gapmers by Isis pharmaceuticals. MOE gapmers or "2'MOE gapmers" are an antisense phosphorothioate oligonucleotide of 15-30 nucleotides wherein all of the backbone linkages are modified by adding a sulfur at the non-bridging oxygen (phosphorothioate) and a stretch of at least 10 consecutive nucleotides remain unmodified (deoxy sugars) and the remaining nucleotides contain an O'-methyl O'-ethyl substitution at the 2' position (MOE).

Next to the use of the inhibitory RNA technology to reduce or inhibitor functional expression of the LIPIN gene on the level of gene product, inhibitors of functional expression of the LIPIN gene can also act at the DNA level. If inhibition is to be achieved at the DNA level, this may be done using gene therapy to knock-out or disrupt the target gene. As used herein, a "knock-out" can be a gene knockdown or the gene can be knocked out by a mutation such as, a point mutation, an insertion, a deletion, a frameshift, or a missense mutation by techniques known in the art, including, but not limited to, retroviral gene transfer. Another way in which genes can be knocked out is by the use of zinc finger nucleases. Zinc-finger nucleases (ZFNs) are artificial restriction enzymes generated by fusing a zinc finger DNA-binding domain to a DNA-cleavage domain. Zinc finger domains can be engineered to target desired DNA sequences, which enable zinc-finger nucleases to target unique sequence within a complex genome. By taking advantage of endogenous DNA repair machinery, these reagents can be used to precisely alter the genomes of higher organisms. Other technologies for genome customization that can be used to knock out genes are meganucleases and TAL effector nucleases (TALENs, Cellectis bioresearch). A TALEN® is composed of a TALE DNA binding domain for sequence-specific recognition fused to the catalytic domain of an endonuclease that introduces double strand breaks (DSB). The DNA binding domain of a TALEN® is capable of targeting with high precision a large recognition site (for instance 17 bp). Meganucleases are sequence-specific endonucleases, naturally occurring "DNA scissors", originating from a variety of single-celled organisms such as bacteria, yeast, algae and some plant organelles. Meganucleases have long recognition sites of between 12 and 30 base pairs. The recognition site of natural meganucleases can be modified in order to target native genomic DNA sequences (such as endogenous genes). Another recent genome editing technology is the CRISPR/Cas system, which can be used to achieve RNA-guided genome engineering. CRISPR interference is a genetic technique which allows for sequence-specific control of gene expression in prokaryotic and eukaryotic cells. It is based on the bacterial immune system-derived CRISPR (clustered regularly interspaced palindromic repeats) pathway. Recently, it was demonstrated that the CRISPR-Cas editing system can also be used to target RNA. It has been shown that the Class 2 type VI-A CRISPR-Cas effector C2c2 can be programmed to cleave single stranded RNA targets carrying complementary protospacers (Abudayyet et al 2016 Science 10.1126/science.aaf5573). C2c2 is a single-effector endoRNase mediating ssRNA cleavage once it has been guided by a single crRNA guide toward the target RNA. This system can thus also be used to target and thus to break down LIPIN or LIPIN1.

The term "neurological diseases" as used in this application are disorders that affect the brain and/or the central and autonomic nervous systems. Those neurological disorders that are subject of this invention are those such as dystonia, epilepsy, multiple sclerosis, Parkinson's disease, Huntington's disease and Alzheimer's disease.

In another aspect, a pharmaceutical composition is disclosed for use in treatment of neurological diseases, wherein said pharmaceutical composition comprises an inhibitor of functional expression of LIPIN or LIPIN1 and wherein said inhibitor is selected from a gapmer, a shRNA, a siRNA, a CRISPR-Cas, a CRISPR-C2c2, a TALEN, a Zinc-finger nuclease, an antisense oligomer, a miRNA, a morpholino, a locked nucleic acid, a peptide nucleic acid, ribozyme or a meganuclease. In more particular embodiments, said pharmaceutical composition is provided for use in treatment of a neurological disease selected from dystonia, primary dystonia, early-onset dystonia, DYT1 primary dystonia.

This invention thus also relates to pharmaceutical compositions containing functional inhibitors of LIPIN or LIPIN1 described herein before. These compositions can be utilized to achieve the desired pharmacological effect by administration to a patient suffering from neurological disease, particularly dystonia, even more particularly primary dystonia, even more particularly early-onset dystonia, most particularly DYT1 dystonia, in need thereof. A patient, for the purpose of this invention, is a mammal, including a human, in need of treatment for neurological disease, particularly dystonia, even more particularly primary dystonia, even more particularly early-onset dystonia, most particularly DYT1 dystonia. Therefore, the present invention includes pharmaceutical compositions that are comprised of a pharmaceutically acceptable carrier and a pharmaceutically effective amount of a functional inhibitor of LIPIN or LIPIN, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of a functional inhibitor of LIPIN is preferably that amount which produces a result or exerts an influence on the particular condition being treated. The compounds of the present application can be administered with pharmaceutically-acceptable carriers well known in the art using any effective conventional dosage unit forms, including immediate, slow and timed release preparations.

The pharmaceutical compositions of this application may also be in the form of oil-in-water emulsions. The emulsions may also contain sweetening and flavoring agents. Oily suspensions may be formulated by suspending the active ingredient in a vegetable oil such as, for example, *arachis* oil, olive oil, sesame oil or coconut oil, or in a mineral oil such as liquid paraffin. The pharmaceutical compositions may be in the form of sterile injectable aqueous suspensions. Such suspensions may be formulated according to known methods using suitable dispersing or wetting agents and suspending agents, all well-known by the person skilled in the art. The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables. The compositions of the application can also contain other conventional pharmaceutically acceptable compounding ingredients, generally referred to as carriers or diluents, as necessary or desired. The nature of additional ingredients and the need of adding those to the composition of the invention is within the knowledge of a skilled person in the relevant art. Conventional procedures for preparing such compositions in appropriate dosage forms can be utilized. Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)—Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51 (4), 166-171.

In yet another embodiment, even though the functional inhibition of LIPIN or LIPIN1 is sufficient to achieve a therapeutic effect, it is likely that stronger, synergistic effects can be obtained in combination with conventional treatment options for dystonia such as for example injection with Botulinum toxin or deep brain stimulation. The synergistic effect can be obtained through simultaneous, concurrent, separate or sequential use for treating dystonia.

The inhibitor of functional expression of LIPIN may be provided as protein (e.g. nuclease) or as an RNA molecule or may be administered as a nucleic acid molecule encoding said protein or said RNA molecule or as a vector comprising such nucleic acid molecule. If the inhibitor of the invention is administered as protein or RNA molecule, it is particularly envisaged that it is administered intracerebroventricularly, such as e.g. through injection or pump. Alternatively, said inhibitor can be coupled to a (single domain) antibody that targets a blood brain barrier (BBB) receptor. This complex can be injected intravenous after which the BBB receptor targeting antibody will shuttle the complex over the BBB.

In case the inhibitor of the application is provided as a nucleic acid or a vector, it is particularly envisaged that the inhibitor is administered through gene therapy.

In particular embodiments of the application, "LIPIN" as mentioned before and hereafter is human LIPIN and can be LIPIN1, LIPIN2 or LIPIN3. In more particular embodiments, LIPIN is LIPIN1 or a homologue with at least 90%, at least 91%, at least 92%, at least 93%, at least 94%, at least 95%, at least 96%, at least 97%, at least 98%, at least 99%, at least 99.5% homology to LIPIN1. In even more particular embodiments, LIPIN1 encodes one of the isoforms depicted in SEQ ID No: 1-4.

In another aspect, the application provides screening methods to produce or identify an inhibitor of functional expression of LIPIN, comprising:
  determining the storage lipid levels of Torsin or TORSIN knock-out cells in an in vitro cell culture setup;
  administering a test compound to said Torsin or TORSIN knock-out cells;
  wherein, a reduction in said storage lipid levels of at least 10%, at least 20%, at least 30%, at least 40%, at least 50%, at least 60%, at least 70%, at least 80%, at least 90% compared to a condition wherein no test compound was administered, identifies said test compound as an inhibitor of functional expression of LIPIN.

In more particular embodiments, the invention provides screening methods to produce or identify an inhibitor of functional expression of LIPIN, comprising determining the storage lipid levels of Torsin1a or TORSIN1A knock-out cells in an in vitro cell culture set up before and after administering a test compound to said Torsin1a or TORSIN1A knock-out cells; wherein, a reduction in said storage lipid levels of at least 10%, at least 20%, at least 30%, at least 40%, at least 50%, at least 60%, at least 70%, at least 80%, at least 90% compared to a condition wherein no test compound was administered, identifies said test compound as an inhibitor of functional expression of LIPIN.

In even more particular embodiments, the invention provides screening methods to produce or identify an inhibitor of functional expression of LIPIN, comprising determining the storage lipid levels of Torsin1a or TORSIN1A knock-out cells in an in vitro cell culture set up before and after administering a test compound to said Torsin1a or TORSIN1A knock-out cells; wherein, a reduction in said storage lipid levels of at least 10%, at least 20%, at least 30%, at least 40%, at least 50%, at least 60%, at least 70%, at least 80%, at least 90% compared to a condition wherein no test compound was administered, identifies said test compound as an inhibitor of functional expression of LIPIN1.

In another embodiment, the invention provides screening methods to produce or identify an inhibitor of functional expression of LIPIN, comprising:
  administering a test compound to Torsin or TORSIN knock-out cells in an in vitro cell culture setup;
  determining the storage lipid level of said Torsin or TORSIN knock-out cells;
  wherein, a reduction in said storage lipid level of at least 10%, at least 20%, at least 30%, at least 40%, at least 50%, at least 60%, at least 70%, at least 80%, at least 90% compared to a condition wherein no test compound was administered, identifies said test compound as an inhibitor of functional expression of LIPIN.

In more particular embodiments, the invention provides screening methods to produce or identify an inhibitor of functional expression of LIPIN, comprising administering a test compound to Torsin1a or TORSIN1A knock-out cells in an in vitro cell culture set up; determining the storage lipid level of said Torsin1a or TORSIN1A knock-out cells; wherein, a reduction in said storage lipid level of at least 10%, at least 20%, at least 30%, at least 40%, at least 50%, at least 60%, at least 70%, at least 80%, at least 90% compared to a condition wherein no test compound was administered, identifies said test compound as an inhibitor of functional expression of LIPIN1.

In another embodiment, the invention provides screening methods to produce or identify an inhibitor of functional expression of LIPIN, comprising:
  providing an in vitro cell culture of Torsin or TORSIN knock-out cells stained with a dye with specificity to storage lipids;
  administering a test compound to said Torsin or TORSIN knock-out cells;
  imaging the stained storage lipids of the cells in said cell culture; wherein a reduction of storage lipids of 10%, at least 20%, at least 30%, at least 40%, at least 50%, at least 60%, at least 70%, at least 80%, at least 90% compared to the same imaging of cells of a corresponding cell culture without said test compound, identifies said test compound as inhibitor of functional expression of L/P/N.

In a more particular embodiment, screening methods are provided to produce or identify an inhibitor of functional expression of LIPIN1, comprising providing an in vitro cell culture of Torsin1a or TORSIN1A knock-out cells stained with a dye with specificity to storage lipids; administering a test compound to said Torsin1a or TORSIN1A knock-out cells; imaging the stained storage lipids of the cells in said cell culture; wherein a reduction of storage lipids of 10%, at least 20%, at least 30%, at least 40%, at least 50%, at least 60%, at least 70%, at least 80%, at least 90% compared to the same imaging of cells of a corresponding cell culture without said test compound, identifies said test compound as inhibitor of functional expression of LIPIN1.

The term "storage lipids" as used herein refers to triglyceride molecules. Triglycerides are esters derived from glycerol and three fatty acids. Triglycerides (also known as triacylglycerols) are the main constituents of body fat in humans and animals. Methods to stain storage lipids and imaging them are well known in the art and discussed in current application.

In yet another embodiment, a screening method is provided to produce or identify an inhibitor of LIPIN activity or a compound for use in the treatment of dystonia, comprising:
  determining the storage lipid levels of Torsin or TORSIN knock-out cells in an in vitro cell culture set up;

administering a test compound to said Torsin or TORSIN knock-out cells;

wherein, a reduction in said storage lipid levels of at least 10%, at least 20%, at least 30%, at least 40%, at least 50%, at least 60%, at least 70%, at least 80%, at least 90% compared to a condition wherein no test compound was administered, identifies said test compound as an inhibitor of LIPIN activity or as compound for use in the treatment of dystonia.

In a more particular embodiment, a screening method is provided to produce or identify an inhibitor of LIPIN activity or a compound for use in the treatment of dystonia, comprising determining the storage lipid levels of Torsin1a or TORSIN1A knock-out cells in an in vitro cell culture set up before and after administering a test compound to said Torsin1a or TORSIN1A knock-out cells; wherein, a reduction in said storage lipid levels of at least 10%, at least 20%, at least 30%, at least 40%, at least 50%, at least 60%, at least 70%, at least 80%, at least 90% compared to a condition wherein no test compound was administered, identifies said test compound as an inhibitor of LIPIN activity or as compound for use in the treatment of dystonia.

In an even more particular embodiment, a screening method is provided to produce an inhibitor of LIPIN1 activity or a compound for use in the treatment of dystonia, comprising determining the storage lipid levels of Torsin1a or TORSIN1A knock-out cells in an in vitro cell culture set up before and after administering a test compound to said Torsin1a or TORSIN1A knock-out cells; wherein, a reduction in said storage lipid levels of at least 10%, at least 20%, at least 30%, at least 40%, at least 50%, at least 60%, at least 70%, at least 80%, at least 90% compared to a condition wherein no test compound was administered, identifies said test compound as an inhibitor of LIPIN1 activity or as compound for use in the treatment of dystonia.

"LIPIN1 activity" as used herein refers to the functional activity of the enzyme encoded by the LIPIN1 gene. An inhibitor of LIPIN1 activity can be an antibody, a nanobody, a phosphatase, a kinase, a small molecule, etc. Activation of LIPIN can be achieved by dephosphorylation of LIPIN. Said dephosphorylation results in nuclear localization of LIPIN.

In another embodiment, the invention provides screening methods to produce or identify an inhibitor of LIPIN activity or a compound for use in the treatment of dystonia, comprising:

administering a test compound to Torsin or TORSIN knock-out cells in an in vitro cell culture set up;

determining the storage lipid level of said Torsin or TORSIN knock-out cells;

wherein, a reduction in said storage lipid level of at least 10%, at least 20%, at least 30%, at least 40%, at least 50%, at least 60%, at least 70%, at least 80%, at least 90% compared to a condition wherein no test compound was administered, identifies said test compound as an inhibitor of LIPIN activity or as compound for use in the treatment of dystonia.

In a more particular embodiment, a screening method is provided to produce or identify an inhibitor LIPIN1 activity or a compound for use in the treatment of dystonia, comprising administering a test compound to Torsin1a or TORSIN1A knock-out cells in an in vitro cell culture set up; determining the storage lipid level of said Torsin1a or TORSIN1A knock-out cells; wherein, a reduction in said storage lipid level of at least 10%, at least 20%, at least 30%, at least 40%, at least 50%, at least 60%, at least 70%, at least 80%, at least 90% compared to a condition wherein no test compound was administered, identifies said test compound as an inhibitor of LIPIN1 activity or as compound for use in the treatment of dystonia.

In another embodiment, a screening method is provided to produce or identify an inhibitor of LIPIN activity or a compound for use in the treatment of dystonia, comprising:

providing an in vitro cell culture of Torsin or TORSIN knock-out cells stained with a dye with specificity to storage lipids;

administering a test compound to said Torsin or TORSIN knock-out cells;

imaging the stained storage lipids of the cells in said cell culture; wherein a reduction of lipid storage of at least 10%, at least 20%, at least 30%, at least 40%, at least 50%, at least 60%, at least 70%, at least 80%, at least 90% compared to the same imaging of cells of a corresponding cell culture without said test compound, identifies said test compound as inhibitor of LIPIN activity or as compound for use in the treatment of dystonia.

In a more particular embodiment, a screening method is provide to produce or identify an inhibitor of LIPIN activity or a compound for use in the treatment of dystonia, comprising providing an in vitro cell culture of Torsin1a or TORSIN1A knock-out cells stained with a dye with specificity to storage lipids; administering a test compound to said Torsin1a or TORSIN1A knock-out cells; imaging the stained storage lipids of the cells in said cell culture before and after the said administration of said test compound; wherein a reduction of lipid storage of at least 10%, at least 20%, at least 30%, at least 40%, at least 50%, at least 60%, at least 70%, at least 80%, at least 90% compared to the same imaging of cells of a corresponding cell culture without said test compound, identifies said test compound as inhibitor of LIPIN activity or as compound for use in the treatment of dystonia.

In an even more particular embodiment, a screening method is provide to produce or identify an inhibitor of LIPIN1 activity or a compound for use in the treatment of dystonia, comprising providing an in vitro cell culture of Torsin1a or TORSIN1A knock-out cells stained with a dye with specificity to storage lipids; administering a test compound to said Torsin1a or TORSIN1A knock-out cells; imaging the stained storage lipids of the cells in said cell culture before and after the said administration of said test compound; wherein a reduction of lipid storage of at least 10%, at least 20%, at least 30%, at least 40%, at least 50%, at least 60%, at least 70%, at least 80%, at least 90% compared to the same imaging of cells of a corresponding cell culture without said test compound, identifies said test compound as inhibitor of LIPIN1 activity or as compound for use in the treatment of dystonia.

In yet another embodiment, screening methods are provided to produce or identify an inhibitor of functional expression of LIPIN or an inhibitor of LIPIN activity or a compound for use in the treatment of dystonia, comprising:

determining the storage lipid levels and/or cell size of Torsin or TORSIN knock-out cells in an in vitro cell culture set up;

administering a test compound to said Torsin or TORSIN knock-out cells;

wherein, a reduction in said storage lipid levels of at least 10%, at least 20%, at least 30%, at least 40%, at least 50%, at least 60%, at least 70%, at least 80%, at least 90% and/or an increase in cell size of at least 10%, at least 20%, at least 30%, at least 40%, at least 50%, at least 60%, at least 70%, at least 80%, at least 90% compared to a condition wherein no test compound was administered, identifies said test compound as an inhibitor of functional expression of LIPIN or an inhibitor of LIPIN activity or a compound for use in the treatment of dystonia.

In a more particular embodiment, screening methods are provided to produce or identify an inhibitor of functional expression of LIPIN or an inhibitor of LIPIN activity or a compound for use in the treatment of dystonia, comprising determining the storage lipid levels and/or cell size of Torsin1a or TORSIN1A knock-out cells in an in vitro cell culture set up before and after administering a test compound to said Torsin1a or TORSIN1A knock-out cells; wherein, a reduction in said storage lipid levels of at least 10%, at least 20%, at least 30%, at least 40%, at least 50%, at least 60%, at least 70%, at least 80%, at least 90% and/or an increase in cell size of at least 10%, at least 20%, at least 30%, at least 40%, at least 50%, at least 60%, at least 70%, at least 80%, at least 90% compared to a condition wherein no test compound was administered, identifies said test compound as an inhibitor of functional expression of LIPIN or an inhibitor of LIPIN activity or a compound for use in the treatment of dystonia.

In another embodiment, a screening method is provided to produce or identify an inhibitor of functional expression of LIPIN or an inhibitor of LIPIN activity or a compound for use in the treatment of dystonia, comprising:
  administering a test compound to Torsin or TORSIN knock-out cells in an in vitro cell culture set up;
  determining the storage lipid levels and/or cell size of said Torsin or TORSIN knock-out cells;
  wherein, a reduction in said storage lipid levels of at least 10%, at least 20%, at least 30%, at least 40%, at least 50%, at least 60%, at least 70%, at least 80%, at least 90% and/or an increase in cell size of at least 10%, at least 20%, at least 30%, at least 40%, at least 50%, at least 60%, at least 70%, at least 80%, at least 90% compared to a condition wherein no test compound was administered, identifies said test compound as an inhibitor of functional expression of LIPIN or an inhibitor of LIPIN activity or a compound for use in the treatment of dystonia.

In a more particular embodiment, a screening method is provided to produce or identify an inhibitor of functional expression of LIPIN or an inhibitor of LIPIN activity or a compound for use in the treatment of dystonia, comprising administering a test compound to Torsin1a or TORSIN1A knock-out cells in an in vitro cell culture set up; determining the storage lipid levels and/or cell size of said Torsin1a or TORSIN1A knock-out cells; wherein, a reduction in said storage lipid levels of at least 10%, at least 20%, at least 30%, at least 40%, at least 50%, at least 60%, at least 70%, at least 80%, at least 90% and/or an increase in cell size of at least 10%, at least 20%, at least 30%, at least 40%, at least 50%, at least 60%, at least 70%, at least 80%, at least 90% compared to a condition wherein no test compound was administered, identifies said test compound as an inhibitor of functional expression of LIPIN or an inhibitor of LIPIN activity or a compound for use in the treatment of dystonia.

In another embodiment, a screening method is provided to produce or identify an inhibitor of functional expression of LIPIN or an inhibitor of LIPIN activity or a compound for use in the treatment of dystonia, comprising:
  providing an in vitro cell culture of Torsin or TORSIN knock-out cells stained with a dye with specificity to storage lipids and/or a dye to with specificity to cell membranes;
  administering a test compound to said Torsin or TORSIN knock-out cells;
  imaging the stained storage lipids and/or stained cell membranes of the cells in said cell culture; wherein a reduction of lipid storage of at least 10%, at least 20%, at least 30%, at least 40%, at least 50%, at least 60%, at least 70%, at least 80%, at least 90% and/or an increase of cell size of at least 10%, at least 20%, at least 30%, at least 40%, at least 50%, at least 60%, at least 70%, at least 80%, at least 90% compared to the same imaging of cells of a corresponding cell culture without said test compound, identifies said test compound an inhibitor of functional expression of LIPIN or an inhibitor of LIPIN activity or as a compound for use in the treatment of dystonia.

In a more particular embodiment, a screening method is provided to produce or identify an inhibitor of functional expression of LIPIN or an inhibitor of LIPIN activity or a compound for use in the treatment of dystonia, comprising providing an in vitro cell culture of Torsin1a or TORSIN1A knock-out cells stained with a dye with specificity to storage lipids and/or a dye to with specificity to cell membranes; administering a test compound to said Torsin1a or TORSIN1A knock-out cells; imaging the stained storage lipids and/or stained cell membranes of the cells in said cell culture before and after administration of said test compound; wherein a reduction of lipid storage of at least 10%, at least 20%, at least 30%, at least 40%, at least 50%, at least 60%, at least 70%, at least 80%, at least 90% and/or an increase of cell size of at least 10%, at least 20%, at least 30%, at least 40%, at least 50%, at least 60%, at least 70%, at least 80%, at least 90% compared to the same imaging of cells of a corresponding cell culture without said test compound, identifies said test compound an inhibitor of functional expression of LIPIN or an inhibitor of LIPIN activity or as a compound for use in the treatment of dystonia.

In another aspect, a method is provided to produce a pharmaceutical composition comprising a compound identified by the screening methods disclosed in this application. More particularly, methods are provided to produce a pharmaceutical composition for use in treatment of neurological diseases, wherein said pharmaceutical composition comprises a compound identified by a screening method, wherein said screening method comprises the following steps:
  determining the storage lipid levels of Torsin1a or TORSIN1A knock-out cells in an in vitro cell culture set up before and after administering a test compound to said Torsin1a or TORSIN1A knock-out cells;
  wherein, a reduction in said storage lipid levels of at least 10%, at least 20%, at least 30%, at least 40%, at least 50%, at least 60%, at least 70%, at least 80%, at least 90% compared to a condition wherein no test compound was administered, identifies said compound.

Also, methods are provided to produce a pharmaceutical composition for use in treatment of neurological diseases, wherein said pharmaceutical composition comprises a compound identified by a screening method, wherein said screening method comprises the following steps
  determining the storage lipid levels and/or cell size of Torsin1a or TORSIN1A knock-out cells in an in vitro cell culture set up before and after administering a test compound to said Torsin1a or TORSIN1A knock-out cells;
  wherein, a reduction in said storage lipid levels of at least 10%, at least 20%, at least 30%, at least 40%, at least 50%, at least 60%, at least 70%, at least 80%, at least 90% and/or an increase in cell size of at least 10%, at least 20%, at least 30%, at least 40%, at least 50%, at least 60%, at least 70%, at least 80%, at least 90% compared to a condition wherein no test compound was administered, identifies said compound.

In particular embodiments, said neurological disease is selected from dystonia, primary dystonia, early-onset dystonia, DYT1 primary dystonia.

In another particular embodiment, the cells used in the screening methods described in this application are not human embryonic stem cells and/or are not cells derived from human embryos. In an even more particular embodiment, the cells used in the screening methods described in this application are not human. The term "compound" is used herein in the context of a "test compound" or a "drug candidate compound" described in connection with the methods of the present invention. As such, these compounds comprise organic or inorganic compounds, derived synthetically or from natural resources. The compounds include polynucleotides, lipids or hormone analogs that are characterized by low molecular weights. Other biopolymeric organic test compounds include small peptides or peptide-like molecules (peptidomimetics) comprising from about 2 to about 40 amino acids and larger polypeptides comprising from about 40 to about 500 amino acids, such as antibodies or antibody conjugates. For high-throughput purposes, compound libraries may be used. Examples include, but are not limited to, natural compound libraries, allosteric compound libraries, peptide libraries, antibody fragment libraries, synthetic compound libraries, etc. In particular embodiments, a compound will "reduce" or "decrease" the lipid storage level of Torsin or TORSIN knock-out cells. Lipid storage can be easily visualized by lipid dye (e.g. BODIPY 493/503) as in this application, but alternative methods are well-known for the skilled one. In other particular embodiments, a compound will "enhance" or "stimulate" or "increase" the cell size of the Torsin or TORSIN knock-out cells. One of the possible underlying activities is the stimulation or enhancement of membrane lipid synthesis. Assays and methods for visualization and/or measuring the cell size of in vitro cells are known in the art and provided in this application.

In another aspect, the application provides a screening method to identify an inhibitor of functional expression of LIPIN or an inhibitor of LIPIN activity or a compound for use in the treatment of dystonia, said method comprising:
expressing a human hyperactivated LIPIN in a cell;
administering a test compound to said cell;
identifying said test compound as an inhibitor of functional expression of LIPIN or an inhibitor of LIPIN activity or a compound for use in the treatment of dystonia, if the growth of said cell in the presence of said test compound is at least 10%, at least 20%, at least 30%, at least 40%, at least 50%, at least 60%, at least 70%, at least 80%, at least 90%, at least 100%, at least 2-fold, at least 3-fold, at least 5-fold, at least 10-fold higher than the growth of said cell in the absence of said test compound.

In one embodiment, said cell is a eukaryotic or prokaryotic cell. In a particular embodiment, said cell is a yeast cell, an insect cell, a non-human mammalian cell or a human cell not derived from a human embryo. In a more particular embodiment, said cell is a yeast cell. In an even more particular embodiment, said yeast cell is a *Saccharomyces* yeast.

In a more particular embodiment, the application provides a screening method to identify an inhibitor of functional expression of LIPIN1 or an inhibitor of LIPIN1 activity or a compound for use in the treatment of dystonia, said method comprising:
expressing a human hyperactivated LIPIN1 in cell;
administering a test compound to said cell;
identifying said test compound as an inhibitor of functional expression of LIPIN1 or an inhibitor of LIPIN1 activity or a compound for use in the treatment of dystonia, if the growth of said cell in the presence of said test compound is at least 10%, at least 20%, at least 30%, at least 40%, at least 50%, at least 60%, at least 70%, at least 80%, at least 90%, at least 100%, at least 2-fold, at least 3-fold, at least 5-fold, at least 10-fold higher than the growth of said cell in the absence of said test compound.

In one embodiment, said cell is a eukaryotic or prokaryotic cell. In a particular embodiment, said cell is a yeast cell, an insect cell, a non-human mammalian cell or a human cell not derived from a human embryo. In a more particular embodiment, said cell is a yeast cell. In an even more particular embodiment, said yeast cell is a *Saccharomyces* yeast.

In particular embodiments, said dystonia is selected from primary dystonia, early-onset dystonia, DYT1 primary dystonia.

In other particular embodiments, methods are provided to produce a pharmaceutical composition for use in treatment of neurological diseases, in particular a neurological disease selected form dystonia, primary dystonia, early-onset dystonia or DYT1 primary dystonia, wherein said pharmaceutical composition comprises a compound identified by a screening method described above.

"Hyperactivated" LIPIN or LIPIN as used herein refers to a LIPIN protein or LIPIN1 protein that overperforms in converting phosphatidate (PtdA) to diacylglycerol (DAG) thereby affecting the balance between phospholipid and TAG production in favor for TAG. Hyperactivation of LIPIN is associated with its nuclear localization and can be achieved by dephosphorylating LIPIN. A hyperactivated LIPIN or LIPIN1 is thus a constitutively active LIPIN or LIPIN1 and can be constructed by mutation of serine/threonine residues so that the LIPIN or LIPIN1 protein cannot be phosphorylated anymore (also referred to as a phospho-dead LIPIN or LIPIN). The disclosed screening method is based on the observation that LIPIN1 hyperactivity causes cytotoxicity and thus inhibits growth in cells, more particular in yeast cells. Yet, inhibitors of LIPIN functional expression or LIPIN1 activity will be those that allow or restore growth of cells notwithstanding said cells produce a human hyperactivated LIPIN1 protein.

Methods to evaluate growth of cells (e.g. yeast) or to compare growth of treated versus untreated cells are well-known in the art and include for example (without the purpose of being limiting) measurements of optical density at a wavelength of 600 nm, also known as OD600 measurements.

In yet another aspect, the application provides SEQ ID No 7 or a homologue thereof with a least 90%, at least 91%, at least 92%, at least 93%, at least 94%, at least 95%, at least 96%, at least 97%, at least 98%, at least 99%, at least 99.5% homology to SEQ ID No 7 for use in the treatment of neurological diseases. In a particular embodiment, said neurological disease is selected from dystonia, primary dystonia, early-onset dystonia, DYT1 primary dystonia.

In another aspect, the application provides a nucleic acid sequence encoding SEQ ID No 8 or a homologue of SEQ ID No 8 with at least 90%, at least 91%, at least 92%, at least 93%, at least 94%, at least 95%, at least 96%, at least 97%, at least 98%, at least 99%, at least 99.5% homology to SEQ ID No 8 for use in the treatment of neurological diseases. In more particular embodiments, said neurological disease is selected from dystonia, primary dystonia, early-onset dystonia, DYT1 primary dystonia.

SEQ ID No 7 represents the nucleic acid sequence of choline-phosphate cytidylyltransferase A (PCYT1A), while SEQ ID No 8 represents the amino acid sequence of the PCYT1A enzyme. PCYT1A is the human homologue of CCT from this application. The PCYT1A enzyme or the nucleic acid sequence encoding PCYT1A can be administered intracerebroventricularly or by way of gene therapy to stimulate membrane lipid synthesis (and consequently cell membrane synthesis) and counteract the hyperactivation of LIPIN or LIPIN1 activity due to the dystonia causative mutation in TORSIN1A. Gene therapy refers to therapy performed by the administration to a subject of an expressed or expressible nucleic acid. In this embodiment of the application, the nucleic acids produce PCYT1A (CCT), a functional fragment, a functional variant or homologue thereof mediates cell membrane synthesis. A large number of methods for gene therapy are available in the art and a plethora of delivery methods (e.g. viral delivery systems, microinjection of DNA plasmids, biolistics of naked nucleic acids, use of a liposome) are well known to those of skill in the art. Gene therapy vectors can be delivered in vivo by administration to an individual patient, typically by systemic administration (e.g., intravenous, intraperitoneal infusion or brain injection).

Throughout this application, sequence homology of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other is regarded as a position with non-identical residues. The alignment of the two sequences is performed by the Needleman and Wunsch algorithm (Needleman and Wunsch (1970) J Mol Biol. 48: 443-453). The computer-assisted sequence alignment above, can be conveniently performed using standard software program such as GAP which is part of the Wisconsin Package Version 10.1 (Genetics Computer Group, Madision, Wis., USA) using the default scoring matrix with a gap creation penalty of 50 and a gap extension penalty of 3. Sequences are indicated as "essentially similar" when such sequences have a sequence identity of at least about 75%, particularly at least about 80%, more particularly at least about 85%, quite particularly about 90%, especially about 95%, more especially about 100%, quite especially are identical.

It is to be understood that although particular embodiments, specific configurations as well as materials and/or molecules, have been discussed herein for cells and methods according to the present invention, various changes or modifications in form and detail may be made without departing from the scope and spirit of this invention. The following examples are provided to better illustrate particular embodiments, and they should not be considered limiting the application. The application is limited only by the claims.

EXAMPLES

Figure 1:
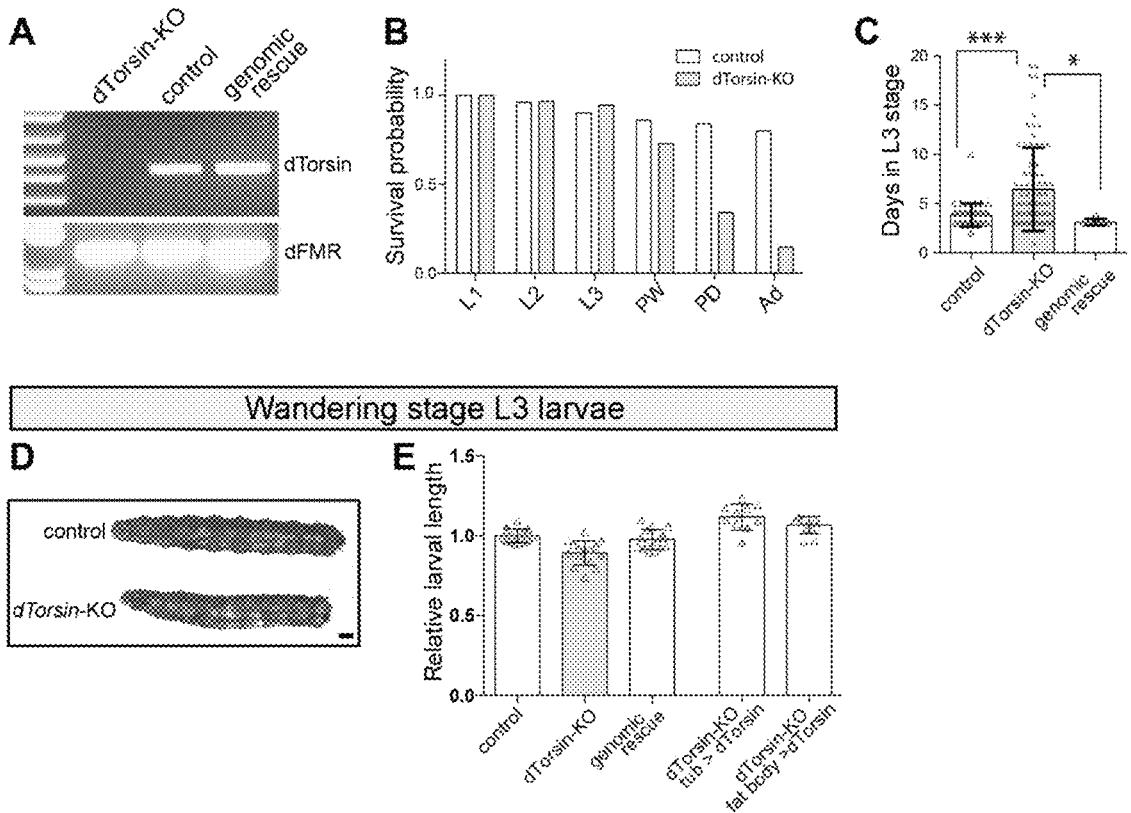
FIG. 1. dTorsin loss affects larval development. A) dTorsin expression is absent from the dTorsin-KO, and restored in dTorsin-KO animals transgenic for a genomic DNA fragment that contains the dTorsin locus (genomic rescue animals). Bands show the intensity of RT-PCR signal for dTorsin or the dFMR gene used as a control to show cDNA quality. Total RNA was extracted using the Ambion RNAqueous-Micro kit, followed by oligodT cDNA synthesis with GoScript (Promega). dTorsin primers were designed against the cDNA region, dFMR primers spanning an intron were used to control against the amplification of genomic DNA or differences in cDNA integrity. The PCR reaction was performed using HiFi DNA Polymerase (Invitrogen). B-C) dTorsin-KO animals die in pupation and spend more time as third instar larvae (L3). B) The majority of dTorsin-KO animals form pupa but fail to survive metamorphosis. Bars show the probability that control (n=43) and dTorsin-KO males (n=64) survive to each developmental stage. L1, L2, L3 refer to larval stages, PW to white pupal stage, PD to dark pupal stage and Ad to adult stage. (C) Bars show time (days; mean±standard deviation (SD)) spent in the L3 stage and points show individual larvae (One-Way ANOVA; *p<0.05; ***p<0.001). D-E) dTorsin-KO wandering stage L3 larvae have a relatively similar size to controls. D) Brightfield images of control and dTorsin-KO larvae. Scale bar shows 50 μm. E) Bars show the mean±SD of larval length relative to the control group, while points show individual larvae. Tub and fat body refer to the tub-GAL4 and r4-GAL4 drivers, respectively, and dTorsin refers to the UAS-dTorsin cDNA transgene.
Figure 2:
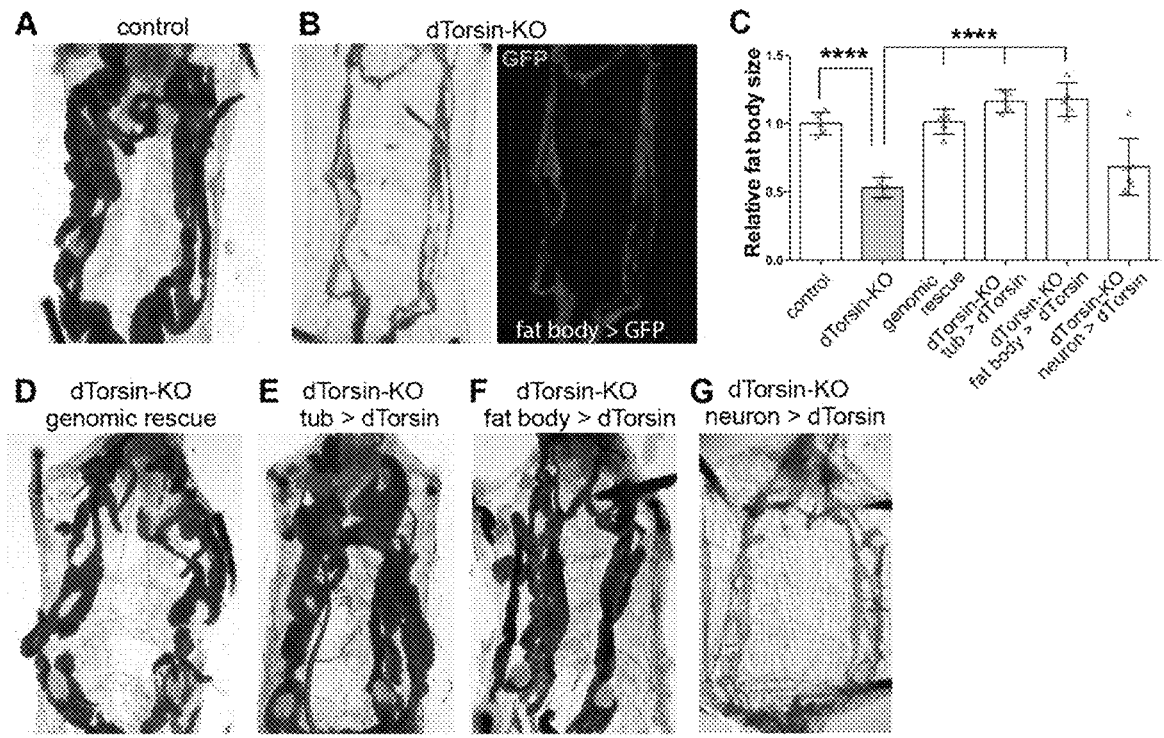
FIG. 2. dTorsin-KO mutants have a small fat body. A-C) dTorsin loss reduces L3 larval fat body size. Brightfield images of (A) the normal fat body that appears as a dark mass in a wandering stage control larvae, and (B) the small fat body of a dTorsin-KO larvae. Right panel of (B) shows fat body expression of Dcg-GFP in the dTorsin-KO. C) Bars show the mean±standard deviation (SD) of fat body size relative to control, while points show individual larvae. The r4-GAL4 line was used for fat body expression, and Nsyb-GAL4 for neuronal expression. (One-way ANOVA; ****p<0.0001). D-F) Brightfield images of the restored fat body in dTorsin-KO larvae re-expressing dTorsin from (D) a genomic DNA transgenic fragment that contains the dTorsin locus (genomic rescue animals), or via a UAS-dTorsin cDNA transgene combined with (E) a ubiquitous (tub), (F) fat body specific (r4), or (G) neuron specific (Nsyb)-GAL4.
Figure 3:
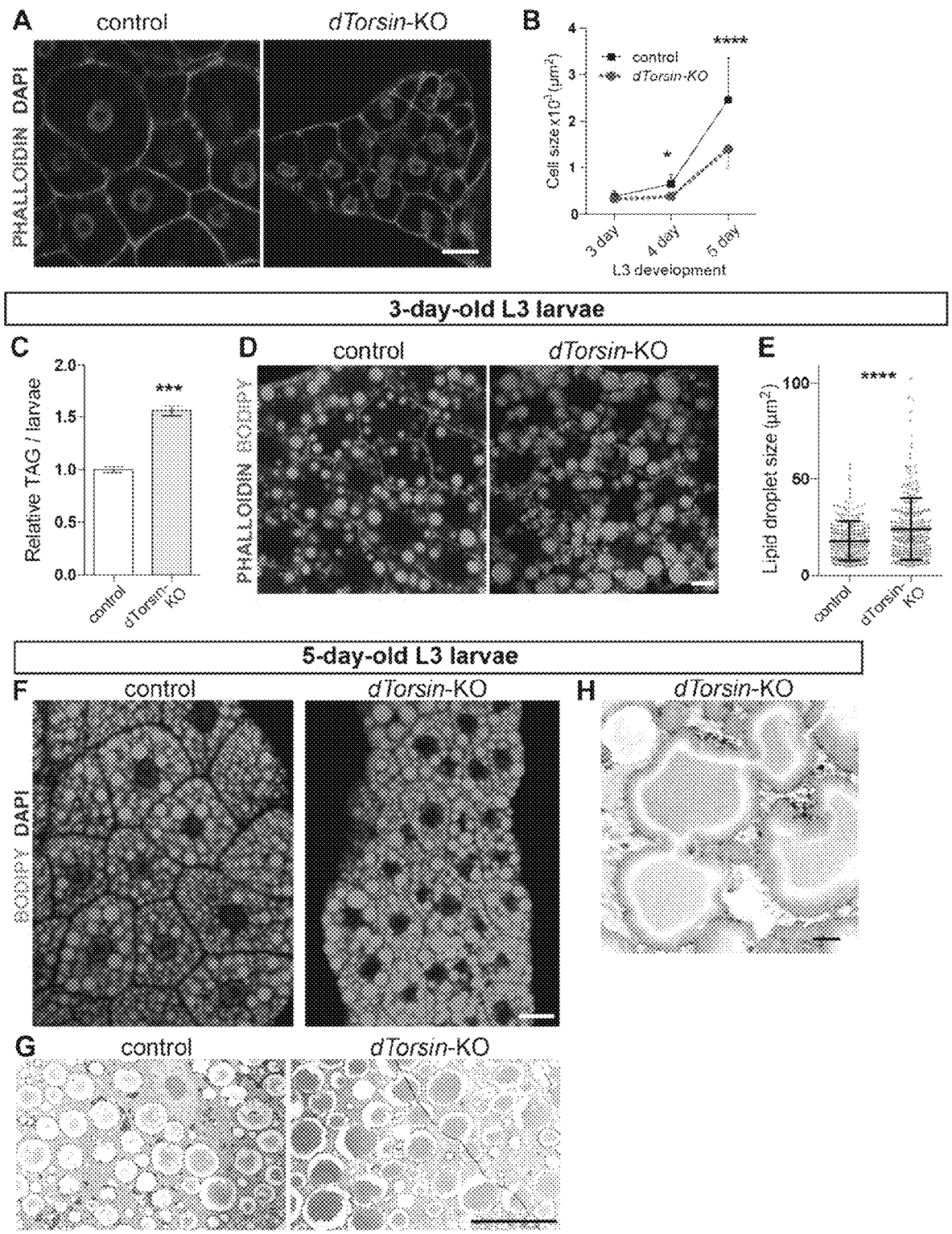
FIG. 3. dTorsin controls growth and lipid storage in fat body cells. A) Confocal images of five-day-old larval fat body cells labeled with phalloidin and DAPI. Scale bar shows 20 μm. B) dTorsin is required for fat body cell growth. Graph shows the mean±SD of fat body cell area of control and dTorsin-KO larvae at three-, four- and five-days after egg laying (Two-Way ANOVA; *$p<0.05$, **$p<0.0001$). C-E) dTorsin suppresses TAG levels in young larvae. C) dTorsin-KO three-day-old larvae contain significantly more TAG (Two tailed T-Test; *$p<0.001$) than controls. Bars show the mean±standard error of the mean (sem) of TAG extracted from three sets of ten L3 larvae (n=30). D) Confocal imaging of neutral lipid dye (BODIPY 493/503) stained lipid droplets in the fat body of three-day-old control and dTorsin-KO L3 larvae. Scale bar shows 10 μm. E) Bars show the mean±SD of lipid droplet size in three-day-old fat body cells of control and dTorsin-KO larvae. Points show the sizes of individual lipid droplets from n>5 cells of at least n=4 larvae (Mann-Whitney; ****$p<0.0001$). F-H) Late larval stage dTorsin-KO larvae have abnormal lipid droplets. F) Confocal images of BODIPY 493/503 staining. Scale bars show 20 μm. G) Transmission electron microscopy (TEM) of a control and dTorsin-KO fat body finds relatively normal lipid droplet packing. Scale bars show 20 μm. H) SEM shows merged lipid droplets in the dTorsin-KO fat body. Scale bar shows 2 μm.
Figure 4:
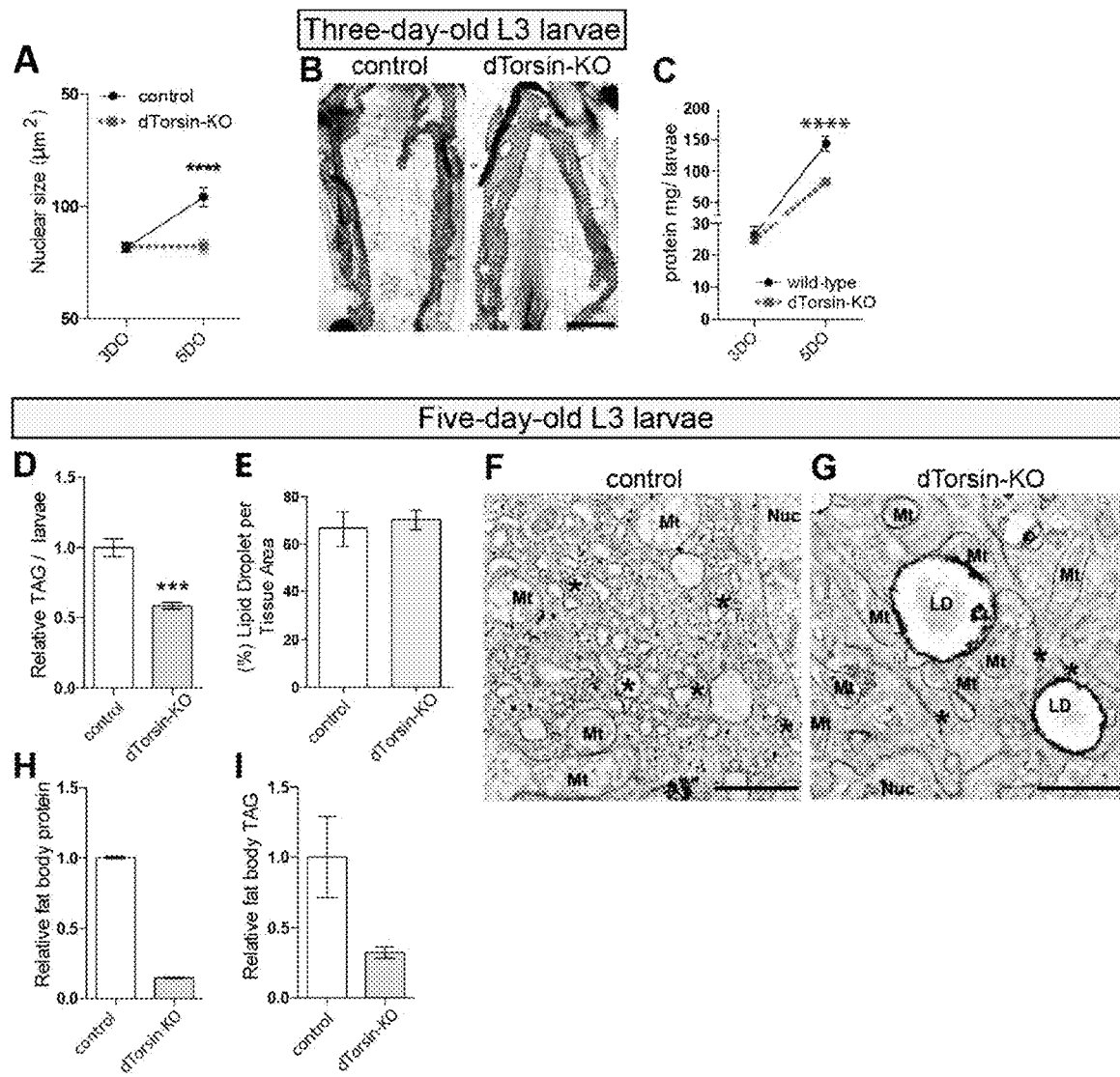
FIG. 4. dTorsin-KO affects adipocyte development and function. A) Nuclear size is normal in 3-day-old dTorsin-KO fat body cells, but fails to expand with development. Nuclei of between 33<n<55 cells from at least four larvae were measured using Image J and confocal images of DAPI stained tissue. Graph shows the mean±standard error of the mean (±sem) of nuclear size (Two-Way ANOVA; **$p<0.0001$). B) Brightfield images showing the relatively normal fat body, outlined in red, of 3-day-old dTorsin-KO larvae compared to a control. Scale bar shows 100 μm. C) Mean±sem of protein yield from 3- and 5-day-old dTorsin-KO larvae. Protein levels were measured using the BCA assay (Pierce) after homogenizing animals. Measurements were made from at least 3 sets of 8 or more larvae (Two-Way ANOVA; $p<0.0001$). D) Late stage dTorsin-KO larvae contain less TAG, consistent with small fat body size and pupal lethality (Two-tailed T-Test; *$p<0.001$). Bars show the mean±sem of TAG extracted from seven sets of ten L3 larvae (n=70). E) The density of lipid droplets is similar in 5-day-old control and dTorsin-KO fat body. Quantification of total tissue area and the area occupied by lipid droplets was performed with ImageJ using images collected from 3D-SEM through the larval fat body. F-G) TEM images showing cytosolic contents in 5-day-old control and dTorsin-KO fat body cells. Images are representative of ER morphology in >10 cells imaged from at least three late stage larvae. Note the abundance of ER tubules in the control compared with dTorsin-KO, which we highlight with * symbols. (Mt) mitochondrion; LD (lipid droplet); Nuc (nucleus). Bars show 1 μm. H) The small fat body of 5-day-old dTorsin-KO larvae contains ~15% of normal protein levels. Control (n=10) and dTorsin-KO fat bodies (n=25) were dissected in PBS, pooled, homogenized, and protein measured using the BCA assay (Pierce). Bars show the mean±sem of three replicate measurements. 1) The small fat body of 5-day-old dTorsin-KO larvae contains ~30% of normal TAG levels detected by mass spectrometry. Tissue was dissected in PBS, and 10 individual fat bodies pooled in 150 mM ammonium bicarbonate. Bars show the mean±sem of measurements from 3 sets of 10 fat bodies (n=30).

Example 1: dTorsin is Required for Fat Body Development dTorsin-KO flies survive through larval stages and most die during pupation. They also spend significantly more time in the third instar larval (L3) stage than normal animals (FIG. 1A-C; "dTorsin-KO" refers to dTorsin$^{KO78}$/y male animals (Wakabayashi-Ito et al., 2011)). We considered which larval tissues require dTorsin for survival to adulthood using the binary GAL4/UAS system where the GAL4 yeast transcriptional activator is expressed as a transgene and activates the UAS promoter to drive expression of downstream sequences. Ubiquitous expression of UAS-dTorsin driven by tubulin-(tub), daughterless-(da), and armadillo-(arm) GAL4 lines restored dTorsin-KO adult hatching with decreasing efficiency correlated to the known level of GAL4 expression (Table 1). We then tested tissue-restricted dTorsin expression. While dTorsin loss is known to impair brain and neuromuscular development (Jokhi et al., 2013; Wakabayashi-Ito et al., 2011), neuron- and muscle-specific dTorsin re-expression failed to prevent lethality (Table 1). In contrast, two drivers that express dTorsin in the larval fat body, Cg- and r4-GAL4 (Hennig et al., 2006; Lee and Park, 2004), increased the number of surviving dTorsin-KO adults (Table 1). The viability of dTorsin-KO larvae also required that the fat body expresses dTorsin throughout larval development, since survival was unaffected by a third fat body driver, Lsp2-GAL4, that only expresses in late stage larvae and adults (Table 1). The fly fat body is the equivalent of vertebrate liver and adipose tissue and is the main site of TAG synthesis and storage in larvae. We find that the fat body of dTorsin-KO animals is significantly smaller than in control animals (FIG. 2A-C). The reduction in size is highly penetrant, with qualitative scoring indicating that >96% of dTorsin-KO animals had a smaller than normal fat body (n=30). Furthermore, the ~50% decrease in fat body size (FIG. 2C) occurs despite dTorsin-KO larvae attaining a similar size as control larvae (FIGS. 1D & E). We also assessed whether dTorsin directly regulate the fat body, and indeed found that re-expressing dTorsin in the fat-body restores tissue size as efficiently as broad expression (FIG. 2C-F), while re-expressing dTorsin in neuronal cells is ineffective (FIGS. 2C & 2G). The fat body is comprised of post-mitotic cells that expand in size during larval development (Britton and Edgar, 1998; Pierce et al., 2004). Consistent with the smaller tissue size, individual late L3 stage larval dTorsin-KO fat body cells are smaller than control cells (FIG. 3A). Analysis over L3 development shows that dTorsin-KO cells fail to expand like control cells (FIG. 3B), and do not show normal increases in nuclear size (FIG. 4A). Since these data are consistent with the need for dTorsin early in fat body development (Table 1), we further examined fat tissue before growth defects appear (3-day-old; FIG. 3B & FIG. 4AC). We expected that fat body dysfunction would be mirrored by reduced TAG storage lipid levels. Surprisingly, however, there is ~50% more TAG in 3-day-old dTorsin-KO animals than controls, while protein levels are normal (FIG. 3C &FIG. 4C). Furthermore, neutral lipid staining reveals significantly larger lipid droplets in the fat cells of young dTorsin-KO larvae than controls (FIGS. 3D & E).

TABLE 1

Fat body expression of dTorsin suppresses dTorsin-KO pupal lethality.

| UAS- | Driver | Expression | Adult dTorsin-KO hatching |
|---|---|---|---|
| dTorsin | — | — | ∅ |
| | Tub-GAL4 | Ubiquitous | +++ |
| | Da-GAL4 | Ubiquitous | +++ |

TABLE 1-continued

Fat body expression of
dTorsin suppresses dTorsin-KO pupal lethality.

| UAS- | Driver | Expression | Adult dTorsin-KO hatching |
|---|---|---|---|
| | Arm-GAL4 | Ubiquitous | + |
| | Elav-GAL4 | Nervous system | Ø |
| | Nsyb-GAL4 | Nervous system | Ø |
| | TH-GAL4 | Dopaminergic neurons | Ø |
| | Repo-GAL4 | Glial cells | Ø |
| | MHC-GAL4 | Muscle | Ø |
| | r4-GAL4 | Fat body | +++ |
| | Cg-GAL4 | Fat Body | ++ |
| | Lsp2-GAL4 | Fat body (late expression) | Ø |
| | Fkh-GAL4 | Salivary glands | Ø |
| | Btl-GAL4 | Trachea | Ø |
| | Hml-GAL4 | Hemocytes | Ø |
| dTorsin-mGFP | Tub-GAL4 | Ubiquitous | +++ |

Ø indicates less than 20% of the expected number (Mendelian ratio) of dTorsin-KO males hatched as adults,
+ reflects that 20-40% of the expected number were present, ++ 40-60%, and +++ that more than 60% of dTorsin-KO males survived to the adult stage.

We also characterized the fat tissue of later stage 5-day-old dTorsin-KO larvae, particularly since the pupal lethality of dTorsin-KO animals suggests an energy deficit. Indeed, there is less TAG per dTorsin-KO animal at the late larval stage (FIG. 4D) when these animals also have a smaller fat body (FIG. 2A-C). The remaining fat tissue nevertheless displays substantial lipid droplet staining (FIG. 3F), consistent with the excess TAG we detect in younger animals. We also examined fat cell ultrastructure, which revealed relatively normal lipid droplet density (FIGS. 3G & 4E), although 3D scanning electron microscopy (3D-SEM) finds that the dTorsin-KO fat body contains many fused lipid droplets (FIG. 3H). We also fail to see the extensive tubular endoplasmic reticulum structures readily detected in control cells (FIGS. 4F & G). We also dissected 5-day-old dTorsin-KO fat bodies for biochemical analyses. This again suggests the tissue is severely abnormal given that it yields only ~15% of the normal amount of protein alongside ~30% of the normal amount of TAG (FIGS. 4H & I). Considered together these data show that dTorsin acts early in adipose tissue development to suppress TAG and promote cell growth, and that dTorsin loss results in a small, abnormal late-larval fat body. Interestingly, lipid droplet fusion is previously associated with lipid metabolic defects, more specifically when TAG synthesis exceeds membrane lipid production (Krahmer et al., 2011). In addition, abnormal lipid synthesis is known to affect fat cell size (Ugrankar et al., 2011). Thus, dTorsin-KO larvae display several phenotypes associated with dysregulation of the cellular lipid metabolism pathways that operate on the ER-system membranes where torsins reside.

Figure 5:
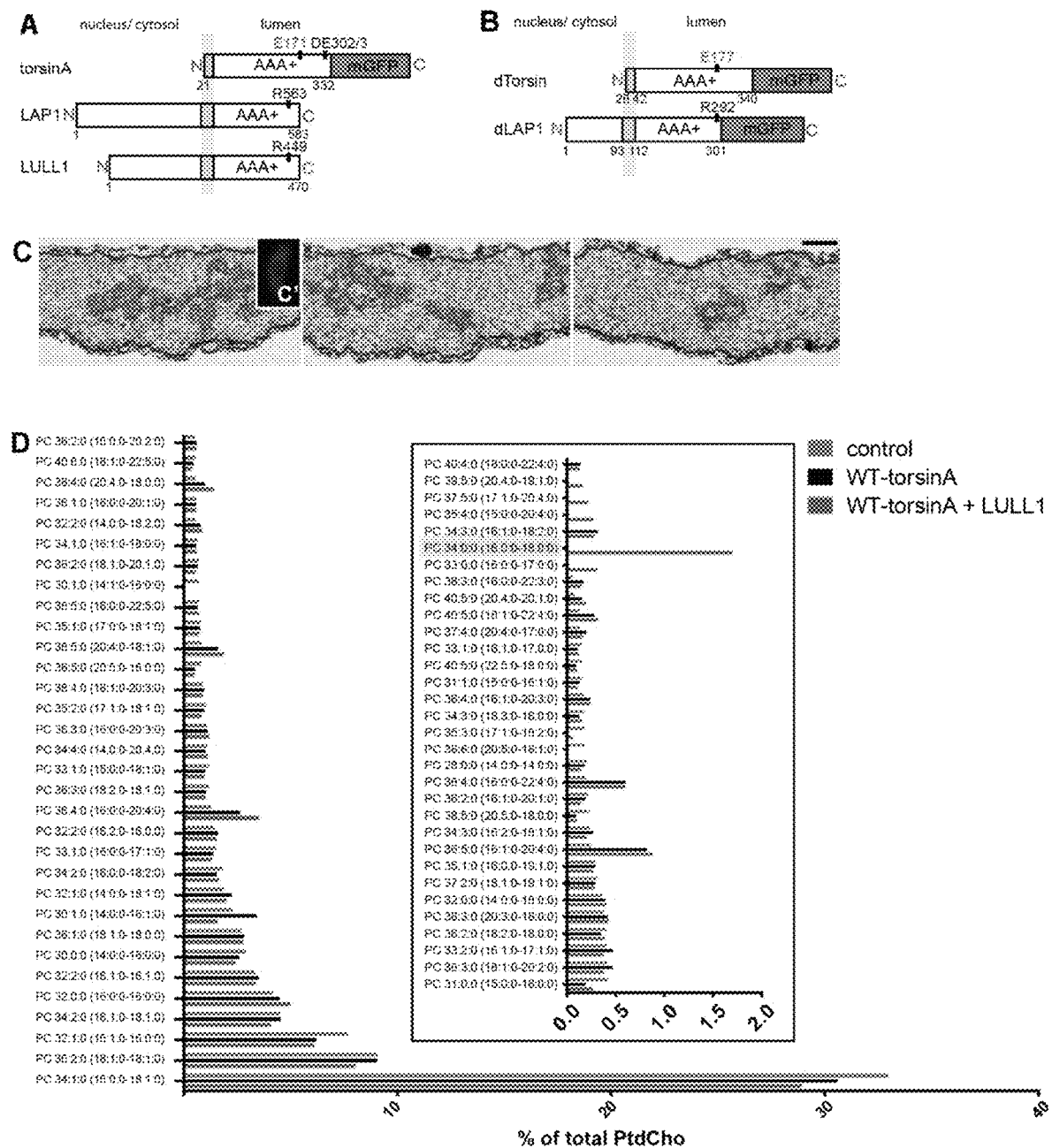
FIG. 5. TORSINA activity induces membrane proliferation from the INM.

Example 2: TORSIN1A Induces Nuclear Membrane Expansion and Increases Lipid Levels Torsins are often found in the NE and there is evidence associating the INM with lipid metabolism (Aitchison et al., 2015; Bahmanyar, 2015; Barbosa et al., 2015a; Ohsaki et al., 2016). In addition, human TORSIN1A concentration in the INM has been associated with altered nuclear structure, while the hypoactive DYT1 dystonia ΔE302/3 mutant fails to cause similar changes (Vander Heyden et al., 2009). We now turned to live-cell imaging to examine whether a relationship exists between INM-localized TORSIN1A, nuclear membrane restructuring, and lipid metabolism, by exploiting the previously described system where expression of the LULL1 AAA+ cofactor induces rapid redistribution of TORSIN1A from the bulk-ER to the INM (Goodchild et al., 2015). We imaged TORSIN1A-mGFP (FIG. 5A) in human U2OS cells stably transfected with a tetracycline-inducible LULL1 cDNA. After ~six hours of tetracycline treatment we see the first cells where TORSIN1A moves from the main-ER to the INM, and the majority of cells have triggered TORSIN1A relocalization after ~ten hours of inducing LULL1 transcription (Goodchild et al., 2015; Vander Heyden et al., 2009). Interestingly, while the TORSIN1A-mGFP signal is initially uniformly distributed around the NE (FIG. 6A, upper three panels) it rapidly coalesces into brighter puncta (FIG. 6A, white arrow) that extend to form tubular and sheet-like structures extending into the nucleus (arrowhead and *, FIG. 6A). The nuclear membranes appear normal in cells prior to and immediately following TORSIN1A relocalization, and we see the first signs of altered nuclear membrane structure on average 25 minutes after TORSIN1A starts to concentrate in the INM (FIG. 6B), suggesting that changes in NE structure are a direct response to TORSIN1A relocalization. An ultrastructural examination of TORSIN1A-modified nuclear membranes shows that cells co-expressing TORSIN1A and LULL1 had stacks and swirls of membrane within the nucleus (FIG. 6C) that were not present in control cells (FIG. 6D). These abnormal structures were comprised of parallel double membranes, reminiscent of the nuclear membranes, but apparently expanded and collapsed into the nuclear interior (FIG. 6C). We then used correlative light 3D-EM to specifically examine the relationship between ultrastructure and the nuclear membrane changes. We selected a cell where light microscopy detected complex nuclear membrane morphology (FIG. 6E') and find this nucleus contains multiple membrane stacks (FIG. 6E). In contrast, we do not see membrane in a neighboring cell nucleus where TORSIN1A-mGFP had not yet relocalized (FIG. 5C), again associating TORSIN1A in the INM with membrane changes. Since the dTorsin-KO phenotypes indicate defects in lipid metabolism we examined whether TORSIN1A affects cellular lipid levels. We used quantitative mass-spectrometry to compare control conditions against cells where eleven hours of LULL1 expression redistributes TORSIN1A to the INM and causes nuclear membrane overgrowth in most cells. Strikingly, cells with TORSIN1A-induced membrane expansion have almost double the lipid content of controls (FIG. 6F). This excess lipid is largely comprised of bulk membrane phospholipids, PtdCho and PtdEtn, although significantly more PtdIns is also present (FIG. 6G). We also identify higher levels of some rare PtdCho species, including saturated PtdCho that is elevated >50 fold to represent 1.7% of total PtdCho (FIG. 5D). These data again associate TORSIN activity with altered cellular lipid metabolism, in this case regulating nuclear membrane area and membrane lipid levels.

Example 3: dTorsin Suppression of Lipin Activity is Required in Fly Development Taken together, the opposing effects of TORSIN activity on TAG and bulk membrane lipid levels suggest that TORSINS control the balance between storage and membrane lipid synthesis (FIG. 7). We returned to the fly to explore the in vivo physiological role of Torsin regulated cellular lipid metabolism. We confirmed that dTorsin-mGFP is active (Table 1; FIG. 5B), and find that this concentrates in the fat cell NE (FIG. 8A). *Drosophila* has one Torsin AAA+ cofactor, CG14103 (Sosa et al., 2014), that also concentrates in the NE (FIG. 8B) suggesting it binds lamins like mammalian LAP1 (Martin et al., 1995). We examined the role of Torsins in lipid homeostasis further by co-overexpressing UAS-dTorsin-mGFP and—dLAP1-mGFP with tub-GAL4 (FIG. 9A). We find, as expected, that this significantly reduces fat body TAG and elevates the abundant fat body membrane lipid, PtdEtn (Carvalho et al., 2012) (FIG. 8C). Nuclear morphology appears normal in dTorsin and dLAP1 expressing fat cells (FIGS. 9B & C). However we see larger distended ER sheets in place of the small and predominantly tubular ER of control cells (FIGS. 8D & E); the reverse of the observation made in dTorsin-KO fat cells that appear to lack ER (FIGS. 4F & G). Two enzymes are associated with the balance between storage lipid and membrane lipid synthesis: 1) CCT that upregulates membrane lipids (Cornell and Ridgway, 2015), and 2) LIPIN that promotes TAG synthesis (Ugrankar et al., 2011) and negatively regulates membrane synthesis (Craddock et al., 2015) (FIGS. 7B and C). Cct is in the nucleus of normal fat body cells (FIG. 10A & FIG. 11A), consistent with the typical localization of this enzyme (Wang et al., 1993). Some cells also show a small amount of NE enriched Cct (FIG. 11B), the same site where mammalian CCTα induces membrane biogenesis (Lagace and Ridgway, 2005). Furthermore, RNAi knock-down of dLipin expression causes Cct to concentrate around the nuclear membrane (FIG. 10B) which, given that CCT is activated upon membrane binding (Cornell and Ridgway, 2015), suggests that Lipin regulates *Drosophila* Cct like in other systems. In contrast, the majority of dTorsin-KO fat cells lack nuclear Cct signal (FIG. 10C & FIG. 11C), suggesting that Cct is negatively affected by loss of dTorsin. We then examined the localization of Lipin that cycles between the cytosol and nucleus (Peterfy et al., 2010; Peterfy et al., 2001; Peterson et al., 2011). *Drosophila* Lipin is predominantly cytosolic in control fat body cells (FIG. 10D), but we instead see many cells with nuclear Lipin in the dTorsin-KO (FIG. 10E). This change in localization is paralleled by a decrease in total anti-Lipin immunoreactivity (FIG. 10F). Notably, both the nuclear localization of LIPIN and lower LIPIN levels have been previously associated with LIPIN activation through dephosphorylation (Hsieh et al., 2015; Peterfy et al., 2001; Peterson et al., 2011), suggesting that dTorsin loss promotes Lipin activation. We next assessed whether dTorsin affects the fat body lipidome in a manner consistent with CCct suppression and/or Lipin activation. We dissected fat tissue from 5-day old dTorsin-KO larvae to acquire sufficient material for mass spectrometry since this contains only ~30% of the normal amount of lipid (FIG. 12A). We then analyzed the relative abundance of bulk membrane lipids and Lipin-metabolized lipids. This identified large changes in the lipid classes directly affected by Lipin activity. We see that the dTorsin-KO fat body lipidome is ~4-fold under-represented in the Lipin substrate, PtdA, while DAG is ~6 fold overrepresented compared to their abundance in control samples (FIG. 10G). In contrast, bulk membrane lipids are normally represented (FIG. 10G), although a significant change in PtdCho saturation nevertheless points to defects in PtdCho metabolism (FIG. 12B). We also assessed whether Lipin-metabolized lipids are affected by dTorsin hyperactivity. We indeed detect that dTorsin and dLAP1 co-expression significantly elevate PtdA abundance relative to that in the control fat body lipidome (FIG. 10H). The tub-GAL4 expressed dTorsin/dLap1 fat cell lipidome is also significantly over represented in the PtdA derived lipids, PtdIns and PtdGly, compared to control samples (FIG. 7; FIG. 10H). We then specifically tested whether dLipin hyperactivity explains why dTorsin loss negatively affects *Drosophila* development. We approached this by genetically suppressing dLipin in the dTorsin-KO using weakly expressed dLipin RNAi, given that strong suppression of dLipin causes severe defects (Ugrankar et al., 2011). We confirmed that TAG levels are reduced in arm-GAL4 dLipin RNAi expressing animals consistent with Lipin inhibition (FIG. 10I). While this was insufficient to increase fat tissue size of 5-day-old dTorsin-KO larvae (FIGS. 12C & D), it nevertheless significantly increases the size of dTorsin-KO fat cells (FIG. 10J, FIG. 12E). We next examined whether dLipin RNAi rescues broader physiological defects in the dTorsin-KO. Late-stage L3 dTorsin-KO animals weigh significantly less than control larvae, and we find that dLipin RNAi significantly increases their weight (FIG. 10K). We then assessed dTorsin-KO adult hatching as the broadest measure of whether dTorsin-control of lipid metabolism through Lipin underlies the importance for *Drosophila* development. As previously shown (Wakabayashi-Ito et al., 2011), under twenty percent of dTorsin-KO animals hatch as adults (Table 1; FIG. 10L). We tested whether this number is affected by coexpressing dLipin RNAi and indeed detect a significant increase in survival to an average of 48% dTorsin-KO survival. In contrast, GFP or dLipin cDNA expressing have no effect (FIG. 10L). We then further confirmed the benefit of dLipin suppression using a partial loss-of function allele with a P-element inserted into the dLipin promoter (dLipin$_{KG00562}$). This allele also reuses the lethality of dTorsin-KO flies, with a dose dependent effect where heterozygosity for dLipin$_{KG00562}$ is non-significantly associated with 25% dTorsin-KO survival, while homozygosity significantly improves hatching to a 53% average (FIG. 10L).

Example 4. Inhibition of Functional Expression of Lipin in Torsin1a (Tor1a) Mutant Mice We validated our results in mammals using the previously generated Torsin1a knock-out and knock-in mouse models. Tor1a$^{-/-}$ mice contain a large deletion, while the Tor1a$^{\Delta gag}$ line contains the Δgag mutation in the endogenous mouse Tor1a gene (Goodchild et al 2005). Both Tor1a$^{+/-}$ and Tor1a$^{+/\Delta gag}$ heterozygous intercrosses generate expected genotypes with normal Mendelian frequency. However, while heterozygotes are indistinguishable from their littermate controls, Tor1a$^{-/-}$ and Tor1a$^{\Delta gag/\Delta gag}$ animals die within 48 hr of birth. Both sets of homozygous animals move, breath, and respond to stimuli, but they typically fail to feed or vocalize, and both show characteristic nuclear membrane defects in neurons (Goodchild et al 2005). First, we examined LIPIN activity in embryonic mouse brains. LIPIN is a magnesium-dependent phosphatidate (PtdA) phosphatase (PAP) that therefore converts PtdA to diacylglycerol (DAG). We added fluorescently labeled PtdA to brain lysates, incubated these in the presence and absence of EDTA, and then used thin-layer chromatography to detect the presence of fluorescently labeled DAG. We performed this direct biochemical measure of LIPIN activity in duplicate samples prepared from 4 control (wild-type and Tor1a$^{+/-}$) and 8 Tor1a mutant (Tor1a$^{-/-}$ and Tor1a$^{\Delta gag/\Delta gag}$) embryonic mouse brains. We detected a 3-fold increase of magnesium dependent DAG production in Tor1a mutant brains compared to control brains (FIG. 13). A one-tailed T-test verified that this increase is statistically significant. This proves that torsinA inhibits lipin in mammalian neurons, like was found with fly torsin in non-neuronal cells.

Second, we asked whether lipin hyperactivity underlies the neurological consequences of torsinA loss and whether the neurological defects of the dystonia-related Tor1a mutation could be rescued by inhibiting the functional expression of Lipin. The human and mouse genomes encode three LIPIN homologues: LIPIN 1, 2 and 3, that all have magnesium dependent PtdA phosphatase activity (Csaki et al 2014, Molecular Metabolism 3: 145-154). LIPIN 1 was selected since homozygous deletion is shown to significantly reduce brain magnesium-dependent PtdA-phosphatase activity (Harris, et al. JBC 282, p 277 (2006)). Mice harboring a Lipin1 null allele were crossed with heterozygous Tor1a$^{+/\Delta gag}$ mice. The F1 progeny was genotyped and the Tor1a$^{+/\Delta gag}$ lipin1$^{+/-}$ mice were selected. The selected genotypes were crossed, phenotyped and genotyped. The Lipin1 knock-out, although only partially reducing general PAP activity (FIG. 14) since there are 3 Lipin genes in mammals, significantly increased the survival of Tor1a$^{\Delta gag/\Delta gag}$ mutant mice after birth (FIG. 15). Moreover knocking-out Lipin1 in embryonic mice reduced both the number of cells that show nuclear membrane defects (FIG. 16 A-B) as well as the severity of the nuclear membrane defects (FIG. 16 C-D). These defects (also referred to as nuclear membrane blebbing) observed in the nuclear membrane of Tor1a$^{-/-}$ and Tor1a$^{\Delta gag/\Delta gag}$ mutants are well known in the art as the prime cell biological read-out of strong TORSIN1A loss (Cascalho et al., 2016; Goodchild et al., 2005; Tanabe et al., 2016). We are also designing gapmers against Lipin1 and are evaluating first in vitro the efficient downregulation of all LIPIN1 isoforms together. In a next step the most efficient gapmers are evaluated in vivo. Therefore we are administering the gapmers directly to fetuses of pregnant Tor1a$^{+/\Delta gag}$ mice in utero. After birth, the treated mice are evaluated (phenotypically and genotypically) postnatally.

Example 5. Lipin Hyperactivity Underlies Tor1a Mediated Dystonia

Next, it was examined whether the disease genotype of Tor1a$^{+/\Delta gag}$ is sufficient to raise LIPIN activity. As expected if LIPIN activity is indeed the correlate of dystonia, LIPIN activity was significantly elevated (FIG. 17; p=0.021) in the brains of the genetically accurate Tor1a$^{\Delta gag/+}$ DYT1 mice. This is the first time that a biochemical defect can be associated with the dystonia disease insult. Interestingly, the PAP activity of Tor1a$^{\Delta gag/+}$ animals has a wider than normal variance, suggesting variability in how animals are affected by Tor1a$^{\Delta gag/+}$ (FIG. 17). This is intriguing given the partial penetrance of this genotype in driving dystonia in humans.

CONCLUSION

To summarize, Applicant has identified a surprising link between dystonia and lipid metabolism defects and demonstrated that this is due to LIPIN hyperactivity. In fly adipose tissue, dTorsin loss leads to increased TAG and decreased phospholipid synthesis. These developmental defects can surprisingly be overcome by reducing the expression of Lipin. Similarly, in mice, the highly reduced lifespan of homozygous Tor1a mutants can significantly be expanded by reducing Lipin expression. Intriguingly, the characteristic nuclear membrane defects in brain neuronal cells of homozygous Tor1a mutant mice can be rescued by reducing Lipin expression. The finding that hyperactivation of LIPIN in humans is causal to DYT1 dystonia is further substantiated by the demonstration that LIPIN is hyperactivated in the genetically accurate Tor1a$^{\Delta gag/+}$ disease model. In current application, Applicant discloses means and methods for the treatment of dystonia and related neurological diseases.

Materials and Methods

Fly Lines and Analysis

The w-, dTorsinKO78/FM7i, Act-GFP line was kindly provided by Naoto Ito (Wakabayashi-Ito et al., 2011), and the w-line was used as the control for all experiments. The full genotype of other animals is described in Supplemental Experimental Procedures. The developmental survival of animals was followed after allowing mated females to lay eggs on food for 8 h. The next day, newly hatched larvae were picked and individually housed in vials maintained at 25° C. Each day the developmental stage and survival of larvae was assessed. dTorsin-KO hatching was assessed by crossing w-, dTorsinKO78/FM7i, Act-GFP; UAS-dTorsin/UASdTorsin females with males containing a GAL4 transgene. In other experiments the UASelement was exchanged for other transgenes or the dLipin KG00562 allele. The number and genotype of hatched flies was assessed daily, and dTorsin-KO hatching calculated as the fraction of observed dTorsin-KO/predicted fraction based on Mendelian inheritance of the dTorsin-KO allele.

| Line name | genotype | Source (stock number) | References |
| --- | --- | --- | --- |
| dTorsin-KO control | w-, dTorsinKO$^{78}$/FM7i, Act-GFP w- | Gift from Naoto Ito | (Wakabayashi-Ito et al., 2011) |
| UAS-dTorsin cDNA | w-; UAS-dTorsin cDNA | Gift from Naoto Ito | (Wakabayashi-Ito et al., 2011) |
| UAS-dTorsin genomic fragment | w-; UAS-dTorsin gDNA | Gift from Kevin Moffat | (Muraro and Moffat, 2006) |
| Genomic rescue | w$^{1118}$; +; Dp(1; 3)DC472, PBac{DC472}VK00033 | Bloomington Stock Center (32303) | (Venken et al., 2010) |
| Lpin RNAi | w$^{1118}$; UAS-RNAi Lipin | Vienna Drosophila Resource Center (v36006) | (Ugrankar et al., 2011) |
| Lpin$^{LOF}$ | yw; Lipin$^{KG00562}$/CyO | Bloomington Stock Center (13293) | (Pereira et al., 2011) |
| Tub-GAL4 | w; +; Tub-GAL4/TM6c, Tb | Gift from Bassem Hassan | (Lee and Luo, 1999) |
| Arm-GAL4 | w; Arm-GAL4 | | (Sanson et al., 1996) |
| Elav-GAL4 | w; Elav-GAL4 | | (Lin and Goodman, 1994) |
| Nsyb-GAL4 | yw; Nsyb-GAL4 | | (Pauli et al., 2008) |
| MHC-GAL4 | w; MHC-GAL4 | | (Schuster et al., 1996) |
| TH-GAL4 | w; +; TH-GAL4 | | (Schwaerzel et al., 2003) |
| Fkh-GAL4 | w; +; fkh-GAL4 | | (Henderson and Andrew, 2000) |
| Btl-GAL4 | w; Btl-GAL4 | | (Shiga et al., 1996) |
| Repo-GAL4 | w; +; repo-GAL4/TM3, Sb | | (Sepp et al., 2001) |

| Line name | genotype | Source (stock number) | References |
|---|---|---|---|
| Hml-GAL4 | w; hml-GAL4 | | (Goto et al., 2003) |
| Da-GAL4 | w; +; Da-GAL4 | Verstreken Lab | (Wodarz et al., 1995) |
| UAS-GAL4 | w; UAS-GAL4 | | |
| r4-GAL4 | yw; r4-GAL4 | Bloomington Stock Center (33832) | (Lee and Park, 2004) |
| Cg-GAL4 | $w^{1118}$; Cg-GAL4 | Bloomington Stock Center (7011) | (Hennig et al., 2006) |
| Lsp2-GAL4 | yw; Lsp2-GAL4 | Bloomington Stock Center (6357) | (Lazareva et al., 2007) |
| Dcg-GFP | w; +; Dcg-GFP | Gift from Jonathan Graff | (Suh et al., 2007) |
| UAS-dTorsin-mGFP | w-; UAS-dTorsin-mGFP/CyO | Described below | |
| UAS-CG14103 mGFP | w-; UAS-CG14103-mGFP/CyO | | |

Labeling, Imaging and Quantification

Larval length was measured by briefly placing larvae in boiling water and then aligning individuals on a glass slide. We collected images of larval fillets after removing all tissue except adipose and nervous system to measure the area occupied by the fat body. These brightfield images were collected with a Zeiss Discovery V12 Stereo microscope. Fluorescent labeling was performed on similar larval fillets fixed in 3.7% formaldehyde and washed in PBS-Tween. Lipid droplets and cell size were visualized using BODIPY 493/503 (1 mg/m), followed by incubation with phalloidin (1 mg/ml). Antibody labeling was performed as previously described (Soldano et al., 2013) using Alexa Fluor 488 secondary antibodies. Prior to imaging using a Nikon A1R Eclipse Ti microscope, the fat body was removed and mounted in Vectashield with DAPI. All image quantification was performed using FIJI. The generation and maintenance of U2OS cell lines is previously described (Vander Heyden et al., 2009). GFP was imaged using a 60× objective on an InCell Analyzer 2000 in cells maintained at 37° C. (GE Healthcare Life Sciences). The anti-dLipin antibody and rabbit anti-CCTα antibody are described in Ugrankar et al., 2011 and Aitchison et al., 2015 respectively. We developed a guinea-pig antibody against a synthetic peptide (DEDADADAEYERRSN (SEQ ID NO: 13)) encoding the carboxyterminal of Drosophila Cct1, and also used mouse anti-tubulin (Sigma). EM of fly and U2OS cells are described in supplemental procedures. TAG and protein were measured as previously described using the Triglyceride Reagent (Sigma; T2449) (Palanker et al., 2009) and BCA assay respectively. Fat bodies were dissected from larval fillet preparations into either 150 mM ammonium bicarbonate for lipidomics, or T-PER buffer (Thermo Scientific) for Western blotting, followed by fastfreezing with liquid nitrogen and homogenization by grinding with a pestle. After homogenization, samples were centrifuged for 5 min at 20 000×g at 4° C., and stored at −80° C. U2OS and fat body lipids were measured by Lipotype Shotgun Lipidomics service (Lipotype GmbH, Dresden, Germany) as previously described (Gerl et al., 2012; Sampaio et al., 2011). Data was analyzed with GraphPad and, unless otherwise stated, Dunnett's post-hoc analysis was used following ANOVA tests.

Construction of New Drosophila Lines

The CG14103 (NM_140892) and dTorsin (NM_131950) cDNA sequences were cloned from cDNA prepared from L3 larvae as described. CG14103 was amplified using primers ATGAGTAATCTGGCGAGACG (SEQ. ID NO: 9) and ACTCAAATGGAGCACCTGATC (SEQ ID NO: 10) containing a Spe1 restriction enzyme site. The product was cloned into pCR8 and then the sequence encoding mGFP (modified from pEGFP-C1 as previously described (Vander Heyden et al., 2009)) was amplified with primers containing Spe1 and Xba1 sites, and ligated into the 3' Spe1 site to generate a carboxyterminal fusion between CG14103 and mGFP. dTorsin was amplified with ATCTATACATTCCACCGCGG (SEQ. ID NO: 11) forward primer containing a Spe1 site and GTAAATGGCCATGGCCACC (SEQ ID NO: 12) reverse primer containing a HindIII site. This was then ligated into a pCR8 plasmid 5' of the MCS and mGFP sequence derived from pEGFP-C1. All coding sequences were verified by sequencing, and then transferred using LR clonase to a Gateway-compatible pUAST vector. These constructs were then sent to Best Gene for injection using the attP40 line and a PhiC31 integrase-mediated site specific transgenesis.

Electron Microscopy

TEM

U2OS cells were incubated for 30 min at room temperature (RT) with freshly prepared fixative (4% paraformaldehyde/3% glutaraldehyde in 100 mM sodium phosphate buffer, pH 7.4) and washed 5×3 min in 0.15M sodium cacodylate buffer (SCB). The samples were then incubated with 2% osmium tetroxide ($OsO_4$) and 1.5% ferrocyanide in 0.15 M SCB (pH 7.4) with 2 mM calcium chloride on ice for 1 hr. Samples were treated with a 0.1% aqueous thiocarbohydrazide solution for 20 min at RT. After, samples were incubated with 1% aqueous uranyl acetate at 4° C. The next day samples were en bloc stained with Walton's lead aspartate. After this the samples were dehydrated using ice-cold solutions of increasing ethanol concentration. After treatment with propylene oxide, samples were embedded in resin. The next day, samples were embedded in fresh resin and cured in the oven at 60° C. for 72 h. Drosophila larval fat bodies were fixed in 2.5% glutaraldehyde, 4% formaldehyde, 0.2% picric acid, 1% sucrose in 0.1M SCB (pH 7.4), and stored in same fixative at 4° C. until processing. Samples were then washed three times in 0.1M SCB, post-stained with 1% OsO4 and 1.5% potassium ferricyanide diluted in 0.1M SCB (pH 7.4) for 2 h. After washing, samples were stained with 0.5% uranyl acetate in 25% methanol overnight, then washed and stained with lead aspartate en bloc for 30 min. After washing, samples were dehydrated in a graded series of ethanol solutions, infiltrated and embedded in epon (Agar100). Samples were then cured in the oven at 60° C. for 48 hrs. Blocks were cut (70 nm) with a Dupont diamond knife on a Leica UCT ultra-microtome and collected on copper grids. Sections were observed and imaged with JEOL JEM1400 transmission electron microscope operated at 80 kV and equipped with an Olympus SIS Quemesa (11 Mpxl) camera.

3D EM 3D correlative light electron microscopy (CLEM) of U2OS cells was performed after first assessing the light microscopy phenotype with a Zeiss Upright 2 inverted microscope maintained at 37° C., then incubating for 30 min at RT with freshly prepared fixative (2% paraformaldehyde, 2.5% glutaraldehyde in 0.15M SCB, pH7.4) and washing 5×3 min in SCB. Samples were then incubated in 1% $OsO_4$, 1.5% potassium ferrocyanide in 0.15M SCB for 40 min at RT. This was immediately followed by a second incubation in OsO4 (1% $OsO_4$ in double distilled (dd)$H_2O$) for 40 min at RT). After washing in dd$H_2O$ for 5×3 min, samples were incubated overnight at 4° C. in 1% uranyl acetate. The next day, uranyl acetate was removed by washing in ddH2O for 5×3 min. After the samples were dehydrated using ice-cold solutions of increasing EtOH concentration. Subsequent infiltration with resin (Durcupan) was done by first incubating in 50% resin in ethanol for 2 hrs, followed by at least 3 changes of fresh 100% resin (including 1 overnight incubation). Next, samples were embedded in fresh resin and cured in the oven at 65° C. for 72 hrs. For Focused Ion Beam—Scanning Electron Microscopy (FIB-SEM) imaging, embedded cells were mounted on aluminum SEM stubs (diameter 12 mm) and samples were coated with ~8 nm of platinum (Quorum Q150T ES). FIB-SEM imaging was performed using a Zeiss Auriga Crossbeam system with Atlas3D software. The FIB was set to remove 5 nm sections by propelling Gallium ions at the surface. Imaging was done at 1.5 kV using an ESB (back-scattered electron) detector. *Drosophila* larvae were prepared for Serial Block Face Scanning Electron Microscopy (SBFSEM) by fixing in 2.5% glutaraldehyde, 4% formaldehyde, 0.2% picric acid, in 0.1M SCB (pH 7.4), and remained stored in fixative at 4° C. until processing. Samples were then post-fixed in a solution of 1% OsO4 containing 1.5% potassium ferrocyanide for 30 min at room temperature, stained with 0.2% tannic acid for 20 min, fixed with 1% $OsO_4$ for 30 min, stained with 1% thiocarbohydrazide for 20 min and incubated again with 1% $OsO_4$ for 30 min. Samples were subsequently contrasted with 0.5% uranyl acetate in 25% methanol overnight at 4° C. and with Walton's lead acetate for 30 min at 60° C. After ethanol dehydration, the samples were infiltrated and embedded in resin (with the modification of a harder epon replacement mixture; Agar100) as for conventional TEM. A small portion of a larvae was mounted on a pin, pre-trimmed in a microtome and placed in a scanning electron microscope (Zeiss VP Sigma) equipped with an internal microtome (Gatan, 3View). Serial sectioning was performed at 200-nm steps. Serial backscattered electron images (1.5 kV, 200 pA, immersion mode) of the block face, focusing on the region of interest, were recorded at 0.0664 m/pixel resolution. The images were segmented using the Microscopy Image Browser (University of Helsinki) software, and video constructed using Amira software.

Lipidomic Mass Spectometry

All liquid handling steps were performed using Hamilton Robotics STARlet robotic platform featuring the Anti Droplet Control for improved organic solvents handling. Samples were infused directly in QExactive mass spectrometer (Thermo Fisher Scientific) with TriVersa NanoMate ion source (Advion Biosciences) and analyzed in both positive and negative polarities, with MS resolution Rm/z=200=280000 and MSMS Rm/z=200=17500, in a single acquisition. MSMS was data independent triggered by an inclusion list encompassing corresponding MS mass ranges scanned in 1 Da increments. Acquired data was analyzed with in-house developed lipid identification software based on LipidXplorer (Herzog et al., 2012; Herzog et al., 2011). Data post-processing and normalization were performed using an in-house developed data management system. Control U2OS cells, U2OS cells stably expressing torsinAmGFP with and without 11 hrs of LULL1 expression were analyzed in triplicate from cultures prepared, induced and collected on different days. The fat bodies of 8-10 five day-old fly larvae were pooled for each analysis, and mass spectrometry performed on triplicate samples (N>24).

REFERENCES

Aitchison, A. J., Arsenault, D. J., and Ridgway, N. D. (2015). Nuclear-localized CTP:phosphocholine cytidylyltransferase alpha regulates phosphatidylcholine synthesis required for lipid droplet biogenesis. Mol Biol Cell 26, 2927-2938. Bahmanyar, 2015

Barbosa, A. D., Sembongi, H., Su, W. M., Abreu, S., Reggiori, F., Carman, G. M., and Siniossoglou, S. (2015a). Lipid partitioning at the nuclear envelope controls membrane biogenesis. Mol Biol Cell.Britton and Edgar, 1998

Carvalho, M., Sampaio, J. L., Palm, W., Brankatschk, M., Eaton, S., and Shevchenko, A. (2012). Effects of diet and development on the *Drosophila* lipidome. Mol Syst Biol 8, 600

Cascalho, A., Jacquemyn, J., and Goodchild, R. E. (2016). Membrane defects and genetic redundancy: are we at a turning point for DYT1 dystonia? Movement Disorders 32, 371-381

Cornell, R. B., and Ridgway, N. D. (2015). CTP:phosphocholine cytidylyltransferase: Function, regulation, and structure of an amphitropic enzyme required for membrane biogenesis. Progress in lipid research 59, 147-171.

Craddock, C. P., Adams, N., Bryant, F. M., Kurup, S., and Eastmond, P. J. (2015). PHOSPHATIDIC ACID PHOSPHOHYDROLASE Regulates Phosphatidylcholine Biosynthesis in *Arabidopsis* by Phosphatidic Acid-Mediated Activation of CTP:PHOSPHOCHOLINE CYTIDYLYL-TRANSFERASE Activity. The Plant cell 27, 1251-1264.

Gerl, M. J., Sampaio, J. L., Urban, S., Kalvodova, L., Verbavatz, J. M., Binnington, B., Lindemann, D., Lingwood, C. A., Shevchenko, A., Schroeder, C., et al. (2012). Quantitative analysis of the lipidomes of the influenza virus envelope and MDCK cell apical membrane. J Cell Biol 196, 213-221.

Goodchild, R. E., and Dauer, W. T. (2005). The AAA+ protein torsinA interacts with a conserved domain present in LAP1 and a novel ER protein. J Cell Biol 168, 855-862. Goodchild et al., 2005

Goodchild, R. E., Buchwalter, A. L., Naismith, T. V., Holbrook, K., Billion, K., Dauer, W. T., Liang, C. C., Dear, M. L., and Hanson, P. I. (2015). Access of torsinA to the inner nuclear membrane is activity dependent and regulated in the endoplasmic reticulum. J Cell Sci 128, 2854-2865.

Goodchild, R. E., Kim, C. E., and Dauer, W. T. (2005). Loss of the Dystonia-Associated Protein TorsinA Selectively Disrupts the Neuronal Nuclear Envelope. Neuron 48, 923-932.

Han, S., Bahmanyar, S., Zhang, P., Grishin, N., Oegema, K., Crooke, R., Graham, M., Reue, K., Dixon, J. E., and Goodman, J. M. (2012). Nuclear envelope phosphatase 1-regulatory subunit 1 (formerly TMEM188) is the metazoan Spo7p ortholog and functions in the lipin activation pathway. J Biol Chem 287, 3123-3137.

Hanson, P. I., and Whiteheart, S. W. (2005). AAA+ proteins: have engine, will work. Nat Rev Mol Cell Biol 6, 519-529.

Harris, T. E., Huffman, T. A., Chi, A., Shabanowitz, J., Hunt, D. F., Kumar, A., and Lawrence, J. C., Jr. (2007). Insulin controls subcellular localization and multisite phosphorylation of the phosphatidic acid phosphatase, lipin 1. J Biol Chem 282, 277-286.

Hennig, K. M., Colombani, J., and Neufeld, T. P. (2006). TOR coordinates bulk and targeted endocytosis in the Drosophila melanogaster fat body to regulate cell growth. J Cell Biol 173, 963-974.

Herzog, R., Schwudke, D., Schuhmann, K., Sampaio, J. L., Bornstein, S. R., Schroeder, M., and Shevchenko, A. (2011). A novel informatics concept for high-throughput shotgun lipidomics based on the molecular fragmentation query language. Genome biology 12, R8.

Herzog, R., Schuhmann, K., Schwudke, D., Sampaio, J. L., Bornstein, S. R., Schroeder, M., and Shevchenko, A. (2012). LipidXplorer: a software for consensual cross-platform lipidomics. PLoS One 7, e29851.

Hsieh, L. S., Su, W. M., Han, G. S., and Carman, G. M. (2015). Phosphorylation regulates the ubiquitin-independent degradation of yeast Pah1 phosphatidate phosphatase by the 20S proteasome. J Biol Chem 290, 11467-11478.

Jokhi, V., Ashley, J., Nunnari, J., Noma, A., Ito, N., Wakabayashi-Ito, N., Moore, M. J., and Budnik, V. (2013). Torsin Mediates Primary Envelopment of Large Ribonucleoprotein Granules at the Nuclear Envelope. Cell Rep 3, 988-995.

Jungwirth, M., Dear, M. L., Brown, P., Holbrook, K., and Goodchild, R. (2010). Relative tissue expression of homologous torsinB correlates with the neuronal specific importance of DYT1 dystonia-associated torsinA. Hum Mol Genet 19, 888-900.

Kim, C. E., Perez, A., Perkins, G., Ellisman, M. H., and Dauer, W. T. (2010). A molecular mechanism underlying the neural-specific defect in torsinA mutant mice. Proc Natl Acad Sci USA 107, 9861-9866.

Lagace, T. A., and Ridgway, N. D. (2005). The rate-limiting enzyme in phosphatidylcholine synthesis regulates proliferation of the nucleoplasmic reticulum. Mol Biol Cell 16, 1120-1130.

Lee, G., and Park, J. H. (2004). Hemolymph sugar homeostasis and starvation-induced hyperactivity affected by genetic manipulations of the adipokinetic hormone-encoding gene in Drosophila melanogaster. Genetics 167, 311-323.

Liang, C. C., Tanabe, L. M., Jou, S., Chi, F., and Dauer, W. T. (2014). TorsinA hypofunction causes abnormal twisting movements and sensorimotor circuit neurodegeneration. The Journal of clinical investigation 124, 3080-3092.

Ohsaki, Y., Kawai, T., Yoshikawa, Y., Cheng, J., Jokitalo, E., and Fujimoto, T. (2016). PML isoform II plays a critical role in nuclear lipid droplet formation. J Cell Biol 212, 29-38.

Palanker, L., Tennessen, J. M., Lam, G., and Thummel, C. S. (2009). Drosophila HNF4 regulates lipid mobilization and beta-oxidation. Cell metabolism 9, 228-239.

Peterfy, M., Phan, J., Xu, P., and Reue, K. (2001). Lipodystrophy in the fld mouse results from mutation of a new gene encoding a nuclear protein, lipin. Nat Genet 27, 121-124.

Peterfy, M., Harris, T. E., Fujita, N., and Reue, K. (2010). Insulin-stimulated interaction with 14-3-3 promotes cytoplasmic localization of lipin-1 in adipocytes. J Biol Chem 285, 3857-3864.

Peterson, T. R., Sengupta, S. S., Harris, T. E., Carmack, A. E., Kang, S. A., Balderas, E., Guertin, D. A., Madden, K. L., Carpenter, A. E., Finck, B. N., et al. (2011). mTOR complex 1 regulates lipin 1 localization to control the SREBP pathway. Cell 146, 408-420.

Pierce, S. B., Yost, C., Britton, J. S., Loo, L. W., Flynn, E. M., Edgar, B. A., and Eisenman, R. N. (2004). dMyc is required for larval growth and endoreplication in Drosophila. Development 131, 2317-2327.

Sampaio, J. L., Gerl, M. J., Klose, C., Ejsing, C. S., Beug, H., Simons, K., and Shevchenko, A. (2011). Membrane lipidome of an epithelial cell line. Proc Natl Acad Sci USA 108, 1903-1907.

Soldano, A., Okray, Z., Janovska, P., Tmejova, K., Reynaud, E., Claeys, A., Yan, J., Atak, Z. K., De Strooper, B., Dura, J. M., et al. (2013). The Drosophila homologue of the amyloid precursor protein is a conserved modulator of Wnt PCP signaling. PLoS biology 11, e1001562.

Sosa, B. A., Demircioglu, F. E., Chen, J. Z., Ingram, J., Ploegh, H. L., and Schwartz, T. U. (2014). How lamina-associated polypeptide 1 (LAP1) activates Torsin. eLife 3.

Tanabe, L. M., Kim, C. E., Alagem, N., and Dauer, W. T. (2009). Primary dystonia: molecules and mechanisms. Nat Rev Neurol 5, 598-609.

Tanabe, L. M., Liang, C.-C., and Dauer, W. T. (2016). Neuronal nuclear membrane budding occurs during a developmental window modulated by Torisin paralogs. Cell Reports 16, 3322-3333

Ugrankar, R., Liu, Y., Provaznik, J., Schmitt, S., and Lehmann, M. (2011). Lipin is a central regulator of adipose tissue development and function in Drosophila melanogaster. Mol Cell Biol 31, 1646-1656.

Vander Heyden, A. B., Naismith, T. V., Snapp, E. L., Hodzic, D., and Hanson, P. I. (2009). LULL1 Retargets TorsinA to the Nuclear Envelope Revealing an Activity that Is Impaired by the DYT1 Dystonia Mutation. Mol Biol Cell 20, 2661-2672.

Vander Heyden, A. B., Naismith, T. V., Snapp, E. L., and Hanson, P. I. (2011). Static retention of the lumenal monotopic membrane protein torsinA in the endoplasmic reticulum. Embo J 30, 3217-3231.

Wakabayashi-Ito, N., Doherty, O. M., Moriyama, H., Breakefield, X. O., Gusella, J. F., O'Donnell, J. M., and Ito, N. (2011). dtorsin, the Drosophila ortholog of the early-onset dystonia TOR1A (DYT1), plays a novel role in dopamine metabolism. PLoS One 6, e26183.

Wang, Y., Sweitzer, T. D., Weinhold, P. A., and Kent, C. (1993). Nuclear localization of soluble CTP:phosphocholine cytidylyltransferase. J Biol Chem 268, 5899-5904.

The invention claimed is:

1. A method for the treatment of a neurological disease in a subject, the method comprising:
    administering to the subject a nucleic acid sequence that is complementary to a nucleic acid sequence encoding Lipin1 thereby inhibiting the functional expression of LIPIN1 in the subject;
    wherein the neurological disease is dystonia caused by at least one mutation in the TORSIN1A gene.

2. The method according to claim 1, wherein the dystonia is primary dystonia, early-onset dystonia, or DYT1 primary dystonia.

3. A method of reducing the functional expression of LIPIN1 in a subject, the method comprising:
    administering to the subject a nucleic acid sequence that is complementary to a nucleic acid sequence encoding Lipin1 that can reduce expression of Lipin1;
    wherein the subject has at least one mutation in the TORSINA gene.

* * * * *

SEQUENCE LISTING

<160> NUMBER OF SEQ ID NOS: 13

<210> SEQ ID NO 1
<211> LENGTH: 890
<212> TYPE: PRT
<213> ORGANISM: Homo sapiens

<400> SEQUENCE: 1

```
Met Asn Tyr Val Gly Gln Leu Ala Gly Gln Val Phe Val Thr Val Lys
1               5                   10                  15

Glu Leu Tyr Lys Gly Leu Asn Pro Ala Thr Leu Ser Gly Cys Ile Asp
            20                  25                  30

Ile Ile Val Ile Arg Gln Pro Asn Gly Asn Leu Gln Cys Ser Pro Phe
        35                  40                  45

His Val Arg Phe Gly Lys Met Gly Val Leu Arg Ser Arg Glu Lys Val
    50                  55                  60

Val Asp Ile Glu Ile Asn Gly Glu Ser Val Asp Leu His Met Lys Leu
65                  70                  75                  80

Gly Asp Asn Gly Glu Ala Phe Phe Val Gln Glu Thr Asp Asn Asp Gln
                85                  90                  95

Glu Val Ile Pro Met His Leu Ala Thr Ser Pro Ile Leu Ser Glu Gly
            100                 105                 110

Ala Ser Arg Met Glu Cys Gln Leu Lys Arg Gly Ser Val Asp Arg Met
        115                 120                 125

Arg Gly Leu Asp Pro Ser Thr Pro Ala Gln Val Ile Ala Pro Ser Glu
    130                 135                 140

Thr Pro Ser Ser Ser Val Val Lys Lys Arg Arg Lys Arg Arg Arg
145                 150                 155                 160

Lys Ser Gln Leu Asp Ser Leu Lys Arg Asp Asp Asn Met Asn Thr Ser
                165                 170                 175

Glu Asp Glu Asp Met Phe Pro Ile Glu Met Ser Ser Asp Glu Ala Met
            180                 185                 190

Glu Leu Leu Glu Ser Ser Arg Thr Leu Pro Asn Asp Ile Pro Pro Phe
        195                 200                 205

Gln Asp Asp Ile Pro Glu Glu Asn Leu Ser Leu Ala Val Ile Tyr Pro
    210                 215                 220

Gln Ser Ala Ser Tyr Pro Asn Ser Asp Arg Glu Trp Ser Pro Thr Pro
225                 230                 235                 240

Ser Pro Ser Gly Ser Arg Pro Ser Thr Pro Lys Ser Asp Ser Glu Leu
                245                 250                 255

Val Ser Lys Ser Thr Glu Arg Thr Gly Gln Lys Asn Pro Glu Met Leu
            260                 265                 270

Trp Leu Trp Gly Glu Leu Pro Gln Ala Ala Lys Ser Ser Pro His
        275                 280                 285

Lys Met Lys Glu Ser Ser Pro Leu Ser Ser Arg Lys Ile Cys Asp Lys
    290                 295                 300

Ser His Phe Gln Ala Ile His Ser Glu Ser Ser Asp Thr Phe Ser Asp
305                 310                 315                 320

Gln Ser Pro Thr Leu Val Gly Gly Ala Leu Leu Asp Gln Asn Lys Pro
                325                 330                 335

Gln Thr Glu Met Gln Phe Val Asn Glu Glu Asp Leu Glu Thr Leu Gly
            340                 345                 350

Ala Ala Ala Pro Leu Leu Pro Met Ile Glu Glu Leu Lys Pro Pro Ser
        355                 360                 365
```

-continued

```
Ala Ser Val Val Gln Thr Ala Asn Lys Thr Asp Ser Pro Ser Arg Lys
    370                 375                 380

Arg Asp Lys Arg Ser Arg His Leu Gly Ala Asp Gly Val Tyr Leu Asp
385                 390                 395                 400

Asp Leu Thr Asp Met Asp Pro Glu Val Ala Ala Leu Tyr Phe Pro Lys
                405                 410                 415

Asn Gly Asp Pro Ser Gly Leu Ala Lys His Ala Ser Asp Asn Gly Ala
            420                 425                 430

Arg Ser Ala Asn Gln Ser Pro Gln Ser Val Gly Ser Ser Gly Val Asp
        435                 440                 445

Ser Gly Val Glu Ser Thr Ser Asp Gly Leu Arg Asp Leu Pro Ser Ile
    450                 455                 460

Ala Ile Ser Leu Cys Gly Gly Leu Ser Asp His Arg Glu Ile Thr Lys
465                 470                 475                 480

Asp Ala Phe Leu Glu Gln Ala Val Ser Tyr Gln Gln Phe Val Asp Asn
                485                 490                 495

Pro Ala Ile Ile Asp Asp Pro Asn Leu Val Val Lys Ile Gly Ser Lys
            500                 505                 510

Tyr Tyr Asn Trp Thr Thr Ala Ala Pro Leu Leu Leu Ala Met Gln Ala
        515                 520                 525

Phe Gln Lys Pro Leu Pro Lys Ala Thr Val Glu Ser Ile Met Arg Asp
    530                 535                 540

Lys Met Pro Lys Lys Gly Arg Trp Trp Phe Ser Trp Arg Gly Arg
545                 550                 555                 560

Asn Thr Thr Ile Lys Glu Glu Ser Lys Pro Glu Gln Cys Leu Ala Gly
                565                 570                 575

Lys Ala His Ser Thr Gly Glu Gln Pro Pro Gln Leu Ser Leu Ala Thr
            580                 585                 590

Arg Val Lys His Glu Ser Ser Ser Asp Glu Glu Arg Ala Ala Ala
        595                 600                 605

Lys Pro Ser Asn Ala Gly His Leu Pro Leu Leu Pro Asn Val Ser Tyr
    610                 615                 620

Lys Lys Thr Leu Arg Leu Thr Ser Glu Gln Leu Lys Ser Leu Lys Leu
625                 630                 635                 640

Lys Asn Gly Pro Asn Asp Val Val Phe Ser Val Thr Thr Gln Tyr Gln
                645                 650                 655

Gly Thr Cys Arg Cys Glu Gly Thr Ile Tyr Leu Trp Asn Trp Asp Asp
            660                 665                 670

Lys Val Ile Ile Ser Asp Ile Asp Gly Thr Ile Thr Arg Ser Asp Thr
        675                 680                 685

Leu Gly His Ile Leu Pro Thr Leu Gly Lys Asp Trp Thr His Gln Gly
    690                 695                 700

Ile Ala Lys Leu Tyr His Lys Val Ser Gln Asn Gly Tyr Lys Phe Leu
705                 710                 715                 720

Tyr Cys Ser Ala Arg Ala Ile Gly Met Ala Asp Met Thr Arg Gly Tyr
                725                 730                 735

Leu His Trp Val Asn Glu Arg Gly Thr Val Leu Pro Gln Gly Pro Leu
            740                 745                 750

Leu Leu Ser Pro Ser Ser Leu Phe Ser Ala Leu His Arg Glu Val Ile
        755                 760                 765

Glu Lys Lys Pro Glu Lys Phe Lys Val Gln Cys Leu Thr Asp Ile Lys
    770                 775                 780

Asn Leu Phe Phe Pro Asn Thr Glu Pro Phe Tyr Ala Ala Phe Gly Asn
```

```
                785                 790                 795                 800
Arg Pro Ala Asp Val Tyr Ser Tyr Lys Gln Val Gly Val Ser Leu Asn
                    805                 810                 815
Arg Ile Phe Thr Val Asn Pro Lys Gly Glu Leu Val Gln Glu His Ala
                820                 825                 830
Lys Thr Asn Ile Ser Ser Tyr Val Arg Leu Cys Glu Val Asp His
                    835                 840                 845
Val Phe Pro Leu Leu Lys Arg Ser His Ser Ser Asp Phe Pro Cys Ser
    850                 855                 860
Asp Thr Phe Ser Asn Phe Thr Phe Trp Arg Glu Pro Leu Pro Pro Phe
    865                 870                 875                 880
Glu Asn Gln Asp Ile His Ser Ala Ser Ala
    885                 890

<210> SEQ ID NO 2
<211> LENGTH: 896
<212> TYPE: PRT
<213> ORGANISM: Homo sapiens

<400> SEQUENCE: 2

Met Ser Arg Val Gln Thr Met Asn Tyr Val Gly Gln Leu Ala Gly Gln
1               5                   10                  15
Val Phe Val Thr Val Lys Glu Leu Tyr Lys Gly Leu Asn Pro Ala Thr
                20                  25                  30
Leu Ser Gly Cys Ile Asp Ile Ile Val Ile Arg Gln Pro Asn Gly Asn
            35                  40                  45
Leu Gln Cys Ser Pro Phe His Val Arg Phe Gly Lys Met Gly Val Leu
    50                  55                  60
Arg Ser Arg Glu Lys Val Val Asp Ile Glu Ile Asn Gly Glu Ser Val
65                  70                  75                  80
Asp Leu His Met Lys Leu Gly Asp Asn Gly Glu Ala Phe Phe Val Gln
                85                  90                  95
Glu Thr Asp Asn Asp Gln Glu Val Ile Pro Met His Leu Ala Thr Ser
                100                 105                 110
Pro Ile Leu Ser Glu Gly Ala Ser Arg Met Glu Cys Gln Leu Lys Arg
            115                 120                 125
Gly Ser Val Asp Arg Met Arg Gly Leu Asp Pro Ser Thr Pro Ala Gln
    130                 135                 140
Val Ile Ala Pro Ser Glu Thr Pro Ser Ser Ser Val Val Lys Lys
145                 150                 155                 160
Arg Arg Lys Arg Arg Lys Ser Gln Leu Asp Ser Leu Lys Arg Asp
                165                 170                 175
Asp Asn Met Asn Thr Ser Glu Asp Glu Asp Met Phe Pro Ile Glu Met
                180                 185                 190
Ser Ser Asp Glu Ala Met Glu Leu Leu Glu Ser Ser Arg Thr Leu Pro
            195                 200                 205
Asn Asp Ile Pro Pro Phe Gln Asp Asp Ile Pro Glu Glu Asn Leu Ser
    210                 215                 220
Leu Ala Val Ile Tyr Pro Gln Ser Ala Ser Tyr Pro Asn Ser Asp Arg
225                 230                 235                 240
Glu Trp Ser Pro Thr Pro Ser Pro Ser Gly Ser Arg Pro Ser Thr Pro
                245                 250                 255
Lys Ser Asp Ser Glu Leu Val Ser Lys Ser Thr Glu Arg Thr Gly Gln
                260                 265                 270
```

```
Lys Asn Pro Glu Met Leu Trp Leu Trp Gly Glu Leu Pro Gln Ala Ala
            275                 280                 285

Lys Ser Ser Ser Pro His Lys Met Lys Glu Ser Ser Pro Leu Ser Ser
    290                 295                 300

Arg Lys Ile Cys Asp Lys Ser His Phe Gln Ala Ile His Ser Glu Ser
305                 310                 315                 320

Ser Asp Thr Phe Ser Asp Gln Ser Pro Thr Leu Val Gly Gly Ala Leu
                325                 330                 335

Leu Asp Gln Asn Lys Pro Gln Thr Glu Met Gln Phe Val Asn Glu Glu
            340                 345                 350

Asp Leu Glu Thr Leu Gly Ala Ala Ala Pro Leu Leu Pro Met Ile Glu
        355                 360                 365

Glu Leu Lys Pro Pro Ser Ala Ser Val Val Gln Thr Ala Asn Lys Thr
    370                 375                 380

Asp Ser Pro Ser Arg Lys Arg Asp Lys Arg Ser Arg His Leu Gly Ala
385                 390                 395                 400

Asp Gly Val Tyr Leu Asp Asp Leu Thr Asp Met Asp Pro Glu Val Ala
                405                 410                 415

Ala Leu Tyr Phe Pro Lys Asn Gly Asp Pro Ser Gly Leu Ala Lys His
            420                 425                 430

Ala Ser Asp Asn Gly Ala Arg Ser Ala Asn Gln Ser Pro Gln Ser Val
        435                 440                 445

Gly Ser Ser Gly Val Asp Ser Gly Val Glu Ser Thr Ser Asp Gly Leu
    450                 455                 460

Arg Asp Leu Pro Ser Ile Ala Ile Ser Leu Cys Gly Gly Leu Ser Asp
465                 470                 475                 480

His Arg Glu Ile Thr Lys Asp Ala Phe Leu Glu Gln Ala Val Ser Tyr
                485                 490                 495

Gln Gln Phe Val Asp Asn Pro Ala Ile Ile Asp Asp Pro Asn Leu Val
            500                 505                 510

Val Lys Ile Gly Ser Lys Tyr Tyr Asn Trp Thr Thr Ala Ala Pro Leu
        515                 520                 525

Leu Leu Ala Met Gln Ala Phe Gln Lys Pro Leu Pro Lys Ala Thr Val
    530                 535                 540

Glu Ser Ile Met Arg Asp Lys Met Pro Lys Lys Gly Arg Trp Trp
545                 550                 555                 560

Phe Ser Trp Arg Gly Arg Asn Thr Thr Ile Lys Glu Ser Lys Pro
            565                 570                 575

Glu Gln Cys Leu Ala Gly Lys Ala His Ser Thr Gly Glu Gln Pro Pro
        580                 585                 590

Gln Leu Ser Leu Ala Thr Arg Val Lys His Glu Ser Ser Ser Asp
    595                 600                 605

Glu Glu Arg Ala Ala Ala Lys Pro Ser Asn Ala Gly His Leu Pro Leu
610                 615                 620

Leu Pro Asn Val Ser Tyr Lys Lys Thr Leu Arg Leu Thr Ser Glu Gln
                625                 630                 635                 640

Leu Lys Ser Leu Lys Leu Lys Asn Gly Pro Asn Asp Val Val Phe Ser
            645                 650                 655

Val Thr Thr Gln Tyr Gln Gly Thr Cys Arg Cys Glu Gly Thr Ile Tyr
        660                 665                 670

Leu Trp Asn Trp Asp Asp Lys Val Ile Ile Ser Asp Ile Asp Gly Thr
    675                 680                 685

Ile Thr Arg Ser Asp Thr Leu Gly His Ile Leu Pro Thr Leu Gly Lys
```

```
            690             695             700
Asp Trp Thr His Gln Gly Ile Ala Lys Leu Tyr His Lys Val Ser Gln
705             710             715             720

Asn Gly Tyr Lys Phe Leu Tyr Cys Ser Ala Arg Ala Ile Gly Met Ala
            725             730             735

Asp Met Thr Arg Gly Tyr Leu His Trp Val Asn Glu Arg Gly Thr Val
            740             745             750

Leu Pro Gln Gly Pro Leu Leu Leu Ser Pro Ser Ser Leu Phe Ser Ala
            755             760             765

Leu His Arg Glu Val Ile Glu Lys Lys Pro Glu Lys Phe Lys Val Gln
            770             775             780

Cys Leu Thr Asp Ile Lys Asn Leu Phe Phe Pro Asn Thr Glu Pro Phe
785             790             795             800

Tyr Ala Ala Phe Gly Asn Arg Pro Ala Asp Val Tyr Ser Tyr Lys Gln
            805             810             815

Val Gly Val Ser Leu Asn Arg Ile Phe Thr Val Asn Pro Lys Gly Glu
            820             825             830

Leu Val Gln Glu His Ala Lys Thr Asn Ile Ser Ser Tyr Val Arg Leu
            835             840             845

Cys Glu Val Val Asp His Val Phe Pro Leu Leu Lys Arg Ser His Ser
    850             855             860

Ser Asp Phe Pro Cys Ser Asp Thr Phe Ser Asn Phe Thr Phe Trp Arg
865             870             875             880

Glu Pro Leu Pro Pro Phe Glu Asn Gln Asp Ile His Ser Ala Ser Ala
            885             890             895

<210> SEQ ID NO 3
<211> LENGTH: 975
<212> TYPE: PRT
<213> ORGANISM: Homo sapiens

<400> SEQUENCE: 3

Met Gly Glu Gln Asp Gly Ile Arg Ser Ser Trp Glu Thr Ser Gln
1               5               10              15

Gly Lys Ser Ser Pro Asp Ser Ala Trp Ser Trp Ile Pro Ile Met Arg
            20              25              30

Asp Pro Gly Trp Ile Arg Asn Val Trp Ser Ser Asn Ile Asn Val Gln
            35              40              45

Thr Met Asn Tyr Val Gly Gln Leu Ala Gly Gln Val Phe Val Thr Val
    50              55              60

Lys Glu Leu Tyr Lys Gly Leu Asn Pro Ala Thr Leu Ser Gly Cys Ile
65              70              75              80

Asp Ile Ile Val Ile Arg Gln Pro Asn Gly Asn Leu Gln Cys Ser Pro
            85              90              95

Phe His Val Arg Phe Gly Lys Met Gly Val Leu Arg Ser Arg Glu Lys
            100             105             110

Val Val Asp Ile Glu Ile Asn Gly Glu Ser Val Asp Leu His Met Lys
            115             120             125

Leu Gly Asp Asn Gly Glu Ala Phe Phe Val Gln Glu Thr Asp Asn Asp
    130             135             140

Gln Glu Val Ile Pro Met His Leu Ala Thr Ser Pro Ile Leu Ser Glu
145             150             155             160

Gly Ala Ser Arg Met Glu Cys Gln Leu Lys Arg Gly Ser Val Asp Arg
            165             170             175
```

```
Met Arg Gly Leu Asp Pro Ser Thr Pro Ala Gln Val Ile Ala Pro Ser
            180                 185                 190

Glu Thr Pro Ser Ser Ser Val Val Lys Lys Arg Arg Lys Arg Arg
            195                 200                 205

Arg Lys Ser Gln Leu Asp Ser Leu Lys Arg Asp Asp Asn Met Asn Thr
            210                 215                 220

Ser Glu Asp Glu Asp Met Phe Pro Ile Glu Met Ser Ser Asp Glu Ala
225                 230                 235                 240

Met Glu Leu Leu Glu Ser Ser Arg Thr Leu Pro Asn Asp Ile Pro Pro
            245                 250                 255

Phe Gln Asp Asp Ile Pro Glu Glu Asn Leu Ser Leu Ala Val Ile Tyr
            260                 265                 270

Pro Gln Ser Ala Ser Tyr Pro Asn Ser Asp Arg Glu Trp Ser Pro Thr
            275                 280                 285

Pro Ser Ser Leu Val Asp Cys Lys Arg Thr Ala Pro His Leu Ala Val
            290                 295                 300

Ala Ala Glu Gly Gly Leu Ser Ser Cys Pro Pro Gln Ser Ser Leu
305                 310                 315                 320

Phe His Pro Ser Glu Ser Pro Ser Gly Ser Arg Pro Ser Thr Pro Lys
            325                 330                 335

Ser Asp Ser Glu Leu Val Ser Lys Ser Thr Glu Arg Thr Gly Gln Lys
            340                 345                 350

Asn Pro Glu Met Leu Trp Leu Trp Gly Glu Leu Pro Gln Ala Ala Lys
            355                 360                 365

Ser Ser Ser Pro His Lys Met Lys Glu Ser Ser Pro Leu Ser Ser Arg
370                 375                 380

Lys Ile Cys Asp Lys Ser His Phe Gln Ala Ile His Ser Glu Ser Ser
385                 390                 395                 400

Asp Thr Phe Ser Asp Gln Ser Pro Thr Leu Val Gly Gly Ala Leu Leu
            405                 410                 415

Asp Gln Asn Lys Pro Gln Thr Glu Met Gln Phe Val Asn Glu Glu Asp
            420                 425                 430

Leu Glu Thr Leu Gly Ala Ala Ala Pro Leu Leu Pro Met Ile Glu Glu
            435                 440                 445

Leu Lys Pro Pro Ser Ala Ser Val Val Gln Thr Ala Asn Lys Thr Asp
450                 455                 460

Ser Pro Ser Arg Lys Arg Asp Lys Arg Ser Arg His Leu Gly Ala Asp
465                 470                 475                 480

Gly Val Tyr Leu Asp Asp Leu Thr Asp Met Asp Pro Glu Val Ala Ala
            485                 490                 495

Leu Tyr Phe Pro Lys Asn Gly Asp Pro Ser Gly Leu Ala Lys His Ala
            500                 505                 510

Ser Asp Asn Gly Ala Arg Ser Ala Asn Gln Ser Pro Gln Ser Val Gly
            515                 520                 525

Ser Ser Gly Val Asp Ser Gly Val Glu Ser Thr Ser Asp Gly Leu Arg
            530                 535                 540

Asp Leu Pro Ser Ile Ala Ile Ser Leu Cys Gly Gly Leu Ser Asp His
545                 550                 555                 560

Arg Glu Ile Thr Lys Asp Ala Phe Leu Glu Gln Ala Val Ser Tyr Gln
            565                 570                 575

Gln Phe Val Asp Asn Pro Ala Ile Ile Asp Asp Pro Asn Leu Val Val
            580                 585                 590

Lys Ile Gly Ser Lys Tyr Tyr Asn Trp Thr Thr Ala Ala Pro Leu Leu
```

```
                        595                 600                 605
Leu Ala Met Gln Ala Phe Gln Lys Pro Leu Pro Lys Ala Thr Val Glu
    610                 615                 620

Ser Ile Met Arg Asp Lys Met Pro Lys Lys Gly Gly Arg Trp Trp Phe
625                 630                 635                 640

Ser Trp Arg Gly Arg Asn Thr Thr Ile Lys Glu Glu Ser Lys Pro Glu
                645                 650                 655

Gln Cys Leu Ala Gly Lys Ala His Ser Thr Gly Glu Gln Pro Pro Gln
                660                 665                 670

Leu Ser Leu Ala Thr Arg Val Lys His Glu Ser Ser Ser Asp Glu
                675                 680                 685

Glu Arg Ala Ala Lys Pro Ser Asn Ala Gly His Leu Pro Leu Leu
    690                 695                 700

Pro Asn Val Ser Tyr Lys Lys Thr Leu Arg Leu Thr Ser Glu Gln Leu
705                 710                 715                 720

Lys Ser Leu Lys Leu Lys Asn Gly Pro Asn Asp Val Val Phe Ser Val
                725                 730                 735

Thr Thr Gln Tyr Gln Gly Thr Cys Arg Cys Glu Gly Thr Ile Tyr Leu
                740                 745                 750

Trp Asn Trp Asp Asp Lys Val Ile Ser Asp Ile Asp Gly Thr Ile
                755                 760                 765

Thr Arg Ser Asp Thr Leu Gly His Ile Leu Pro Thr Leu Gly Lys Asp
770                 775                 780

Trp Thr His Gln Gly Ile Ala Lys Leu Tyr His Lys Val Ser Gln Asn
785                 790                 795                 800

Gly Tyr Lys Phe Leu Tyr Cys Ser Ala Arg Ala Ile Gly Met Ala Asp
                805                 810                 815

Met Thr Arg Gly Tyr Leu His Trp Val Asn Glu Arg Gly Thr Val Leu
                820                 825                 830

Pro Gln Gly Pro Leu Leu Leu Ser Pro Ser Ser Leu Phe Ser Ala Leu
                835                 840                 845

His Arg Glu Val Ile Glu Lys Lys Pro Glu Lys Phe Lys Val Gln Cys
850                 855                 860

Leu Thr Asp Ile Lys Asn Leu Phe Phe Pro Asn Thr Glu Pro Phe Tyr
865                 870                 875                 880

Ala Ala Phe Gly Asn Arg Pro Ala Asp Val Tyr Ser Tyr Lys Gln Val
                885                 890                 895

Gly Val Ser Leu Asn Arg Ile Phe Thr Val Asn Pro Lys Gly Glu Leu
                900                 905                 910

Val Gln Glu His Ala Lys Thr Asn Ile Ser Ser Tyr Val Arg Leu Cys
                915                 920                 925

Glu Val Val Asp His Val Phe Pro Leu Leu Lys Arg Ser His Ser Ser
                930                 935                 940

Asp Phe Pro Cys Ser Asp Thr Phe Ser Asn Phe Thr Phe Trp Arg Glu
945                 950                 955                 960

Pro Leu Pro Pro Phe Glu Asn Gln Asp Ile His Ser Ala Ser Ala
                965                 970                 975

<210> SEQ ID NO 4
<211> LENGTH: 459
<212> TYPE: PRT
<213> ORGANISM: Homo sapiens

<400> SEQUENCE: 4
```

```
Met Ser Arg Val Gln Thr Met Asn Tyr Val Gly Gln Leu Ala Gly Gln
1               5                   10                  15

Val Phe Val Thr Val Lys Glu Leu Tyr Lys Gly Leu Asn Pro Ala Thr
            20                  25                  30

Leu Ser Gly Cys Ile Asp Ile Ile Val Ile Arg Gln Pro Asn Gly Asn
            35                  40                  45

Leu Gln Cys Ser Pro Phe His Val Arg Phe Gly Lys Met Gly Val Leu
50                  55                  60

Arg Ser Arg Glu Lys Val Val Asp Ile Glu Ile Asn Gly Glu Ser Val
65                  70                  75                  80

Asp Leu His Met Lys Leu Gly Asp Asn Gly Glu Ala Phe Phe Val Gln
                85                  90                  95

Glu Thr Asp Asn Asp Gln Glu Val Ile Pro Met His Leu Ala Thr Ser
            100                 105                 110

Pro Ile Leu Ser Glu Gly Ala Ser Arg Met Glu Cys Gln Leu Lys Arg
            115                 120                 125

Gly Ser Val Asp Arg Met Arg Gly Leu Asp Pro Ser Thr Pro Ala Gln
            130                 135                 140

Val Ile Ala Pro Ser Glu Thr Pro Ser Ser Ser Val Val Lys Lys
145                 150                 155                 160

Arg Arg Lys Arg Arg Arg Lys Ser Gln Leu Asp Ser Leu Lys Arg Asp
                165                 170                 175

Asp Asn Met Asn Thr Ser Glu Asp Glu Asp Met Phe Pro Ile Glu Met
            180                 185                 190

Ser Ser Asp Glu Ala Met Glu Leu Leu Glu Ser Ser Arg Thr Leu Pro
    195                 200                 205

Asn Asp Ile Pro Pro Phe Gln Asp Asp Ile Pro Glu Glu Asn Leu Ser
210                 215                 220

Leu Ala Val Ile Tyr Pro Gln Ser Ala Ser Tyr Pro Asn Ser Asp Arg
225                 230                 235                 240

Glu Trp Ser Pro Thr Pro Ser Ser Leu Val Asp Cys Lys Arg Thr Ala
                245                 250                 255

Pro His Leu Ala Val Ala Ala Glu Gly Gly Leu Ser Ser Ser Cys Pro
            260                 265                 270

Pro Gln Ser Ser Leu Phe His Pro Ser Glu Ser Pro Ser Gly Ser Arg
            275                 280                 285

Pro Ser Thr Pro Lys Ser Asp Ser Glu Leu Val Ser Lys Ser Thr Glu
            290                 295                 300

Arg Thr Gly Gln Lys Asn Pro Glu Met Leu Trp Leu Trp Gly Glu Leu
305                 310                 315                 320

Pro Gln Ala Ala Lys Ser Ser Ser Pro His Lys Met Lys Glu Ser Ser
                325                 330                 335

Pro Leu Ser Ser Arg Lys Ile Cys Asp Lys Ser His Phe Gln Ala Ile
            340                 345                 350

His Ser Glu Ser Ser Asp Thr Phe Ser Asp Gln Ser Pro Thr Leu Val
            355                 360                 365

Gly Gly Ala Leu Leu Asp Gln Asn Lys Pro Gln Thr Glu Met Gln Phe
370                 375                 380

Val Asn Glu Glu Asp Leu Glu Thr Leu Gly Ala Ala Pro Leu Leu
385                 390                 395                 400

Pro Met Ile Glu Glu Leu Lys Pro Pro Ser Ala Ser Val Val Gln Thr
            405                 410                 415

Ala Asn Lys Thr Asp Ser Pro Ser Arg Lys Arg Asp Lys Arg Ser Arg
```

```
            420             425             430
His Leu Gly Ala Asp Gly Val Tyr Leu Asp Asp Leu Thr Asp Met Asp
        435                 440                 445

Pro Glu Val Ala Ala Leu Tyr Phe Pro Lys Lys
    450                 455
```

<210> SEQ ID NO 5
<211> LENGTH: 2117
<212> TYPE: DNA
<213> ORGANISM: Homo sapiens

<400> SEQUENCE: 5

```
gaaccggaag cgtgggtctg gcggctgcac cggttcgcgg tcggcgcgag aacaagcagg      60
gtggcgcggg tccgggcatg aagctgggcc gggccgtgct gggcctgctg ctgctggcgc     120
cgtccgtggt gcaggcggtg gagcccatca gcctgggact ggccctggcc ggcgtcctca     180
ccggctacat ctacccgcgt ctctactgcc tcttcgccga gtgctgcggg cagaagcgga     240
gccttagccg ggaggcactg cagaaggatc tggacgacaa cctctttgga cagcatcttg     300
caaagaaaat catcttaaat gccgtgtttg gtttcataaa caacccaaag cccaagaaac     360
ctctcacgct ctccctgcac gggtggacag gcaccggcaa aaatttcgtc agcaagatca     420
tcgcagagaa tatttacgag ggtggtctga acagtgacta tgtccacctg tttgtggcca     480
cattgcactt tccacatgct tcaaacatca ccttgtacaa ggatcagtta cagttgtgga     540
ttcgaggcaa cgtgagtgcc tgtgcgaggt ccatcttcat atttgatgaa atggataaga     600
tgcatgcagg cctcatagat gccatcaagc ctttcctcga ctattatgac ctggtggatg     660
gggtctccta ccagaaagcc atgttcatat ttctcagcaa tgctggagca gaaaggatca     720
cagatgtggc tttggatttc tggaggagtg aaagcagag gaagacatc aagctcaaag     780
acattgaaca cgcgttgtct gtgtcggttt caataacaa gaacagtggc ttctggcaca     840
gcagcttaat tgaccggaac ctcattgatt attttgttcc cttcctcccc ctggaataca     900
aacacctaaa aatgtgtatc cgagtggaaa tgcagtcccg aggctatgaa attgatgaag     960
acattgtaag cagagtggct gaggagatga cattttcctcc caagaggag agagttttct    1020
cagataaagg ctgcaaaacg cgtgttcacca agttagatta ttactacgat gattgacagt    1080
catgattggc agccggagtc actgcctgga gttggaaaag aaacaacact cagtccttcc    1140
acacttccac ccccagctcc tttccctgga agaggaatcc agtgaatgtt cctgtttgat    1200
gtgacaggaa ttctccctgg cattgttttcc accccctggt gcctgcaggc cacccaggga    1260
ccacgggcga ggacgtgaag cctcccgaac acgcacagaa ggaaggagcc agctcccagc    1320
ccactcatcg cagggctcat gatttttttac aaattatgtt ttaattccaa gtgtttctgt    1380
ttcaaggaag gatgaataag tttttattgaa aatgtggtaa ctttattaa aatgattttt    1440
aacattatga gagactgctc agattctaag ttgttggcct tgtgtgtgtg ttttttttta    1500
agttctcatc attattacat agactgtgat gtatctttac tggaaatgag cccaagcaca    1560
catgcatggc attttgttcca caggagggca tccctgggga tgtggctgga gcatgagcca    1620
gctctgtccc aggatggtcc cagcggatgc tgccaggggc agtgaagtgt ttaggtgaag    1680
gacaagtagg taagaggacg ccttcaggca ccacagataa gcctgaaaca gcctctccaa    1740
gggttttcac cttagcaaca atgggagctg tgggagtgat tttggccaca ctgtcaacat    1800
tgttagaac cagtcttttg aaagaaaagt atttccaact tgtcacttgc cagtcactcc    1860
gttttgcaaa aggtggccct tcactgtcca ttccaaatag cccacacgtg ctctctgctg    1920
```

```
gattctaaat tatgtgaatt ttgccatatt aaatcttcct catttatact attatttgtt   1980
acgttcaatc agaatccccg aaacctccta taaagcttag ctgccccttc tgaggatgct   2040
gagaacggtg tctttcttta taaatgcaaa tggctaccgt tttacaataa aattttgcat   2100
gtgccaaaaa aaaaaaa                                                  2117

<210> SEQ ID NO 6
<211> LENGTH: 332
<212> TYPE: PRT
<213> ORGANISM: Homo sapiens

<400> SEQUENCE: 6

Met Lys Leu Gly Arg Ala Val Leu Gly Leu Leu Leu Leu Ala Pro Ser
1               5                   10                  15

Val Val Gln Ala Val Glu Pro Ile Ser Leu Gly Leu Ala Leu Ala Gly
            20                  25                  30

Val Leu Thr Gly Tyr Ile Tyr Pro Arg Leu Tyr Cys Leu Phe Ala Glu
        35                  40                  45

Cys Cys Gly Gln Lys Arg Ser Leu Ser Arg Glu Ala Leu Gln Lys Asp
    50                  55                  60

Leu Asp Asp Asn Leu Phe Gly Gln His Leu Ala Lys Lys Ile Ile Leu
65                  70                  75                  80

Asn Ala Val Phe Gly Phe Ile Asn Asn Pro Lys Pro Lys Lys Pro Leu
                85                  90                  95

Thr Leu Ser Leu His Gly Trp Thr Gly Thr Gly Lys Asn Phe Val Ser
            100                 105                 110

Lys Ile Ile Ala Glu Asn Ile Tyr Glu Gly Gly Leu Asn Ser Asp Tyr
        115                 120                 125

Val His Leu Phe Val Ala Thr Leu His Phe Pro His Ala Ser Asn Ile
    130                 135                 140

Thr Leu Tyr Lys Asp Gln Leu Gln Leu Trp Ile Arg Gly Asn Val Ser
145                 150                 155                 160

Ala Cys Ala Arg Ser Ile Phe Ile Phe Asp Glu Met Asp Lys Met His
                165                 170                 175

Ala Gly Leu Ile Asp Ala Ile Lys Pro Phe Leu Asp Tyr Tyr Asp Leu
            180                 185                 190

Val Asp Gly Val Ser Tyr Gln Lys Ala Met Phe Ile Phe Leu Ser Asn
        195                 200                 205

Ala Gly Ala Glu Arg Ile Thr Asp Val Ala Leu Asp Phe Trp Arg Ser
    210                 215                 220

Gly Lys Gln Arg Glu Asp Ile Lys Leu Lys Asp Ile Glu His Ala Leu
225                 230                 235                 240

Ser Val Ser Val Phe Asn Asn Lys Asn Ser Gly Phe Trp His Ser Ser
                245                 250                 255

Leu Ile Asp Arg Asn Leu Ile Asp Tyr Phe Val Pro Phe Leu Pro Leu
            260                 265                 270

Glu Tyr Lys His Leu Lys Met Cys Ile Arg Val Glu Met Gln Ser Arg
        275                 280                 285

Gly Tyr Glu Ile Asp Glu Asp Ile Val Ser Arg Val Ala Glu Glu Met
    290                 295                 300

Thr Phe Phe Pro Lys Glu Glu Arg Val Phe Ser Asp Lys Gly Cys Lys
305                 310                 315                 320

Thr Val Phe Thr Lys Leu Asp Tyr Tyr Tyr Asp Asp
                325                 330
```

<210> SEQ ID NO 7
<211> LENGTH: 2259
<212> TYPE: DNA
<213> ORGANISM: Homo sapiens

<400> SEQUENCE: 7

| | | | | | |
|---|---|---|---|---|---|
| aggcggaact | tccggctggc | tcttccatca | gctgccttcc | ccgggcgtct | ccccgcaacc | 60 |
| tcctcaactt | ccctagtcag | tgacgcggcg | ccggccagaa | atccgaccgg | accgggctcg | 120 |
| ggggagcgtg | agttgcagca | tgtgccgaag | cgccacctca | gaagataaaa | agaaatgagt | 180 |
| ctcatatttg | gcattctttt | agttaaaaga | gatggatgc | acagtgttca | gccaaggtca | 240 |
| atgcaaggaa | gaggagaaaa | gaggcgcccg | gacccaacgg | ggcaacagaa | gaagatgggg | 300 |
| ttccttccaa | agtgcagcgc | tgtgcagtgg | gcttacggca | accagctcct | ttttctgatg | 360 |
| aaattgaagt | tgactttagt | aagccctatg | tcagggtaac | tatggaagaa | gccagcagag | 420 |
| gaactccttg | tgagcgacct | gtgagagttt | atgccgatgg | aatatttgac | ttatttcact | 480 |
| ctggtcacgc | ccgagctctg | atgcaagcga | agaaccttt | ccctaatacg | tacctcattg | 540 |
| tgggagtttg | cagtgatgag | ctcacacaca | acttcaaagg | cttcacggtg | atgaacgaga | 600 |
| atgagcgcta | tgacgcagtc | cagcactgcc | gctacgtgga | tgaggtggtg | aggaatgcgc | 660 |
| cctggacgct | gacacccgag | ttcctggccg | aacaccggat | tgattttgta | gcccatgatg | 720 |
| atattcctta | ttcatctgct | ggcagtgatg | atgtttataa | gcacatcaag | gaggcaggca | 780 |
| tgtttgctcc | aacacagagg | acagaaggta | tctccacatc | agacatcatc | acccgaattg | 840 |
| tgcgggatta | tgatgtgtat | gcgaggcgga | acctgcagag | gggctacaca | gcaaaggagc | 900 |
| tcaatgtcag | ctttatcaac | gagaagaaat | accacttgca | ggagagggtt | gacaaagtaa | 960 |
| agaagaaagt | gaaagatgtg | gaggaaaagt | caaaagaatt | tgttcagaag | gtggaggaaa | 1020 |
| aaagcattga | cctcattcag | aagtggggag | agaagtcccg | agaattcatt | ggaagttttc | 1080 |
| tggaaatgtt | tggtccggaa | ggagcactga | acatatgct | gaaagagggg | aagggccgga | 1140 |
| tgctgcaggc | catcagcccg | aagcagagcc | ccagcagcag | ccctactcgc | gagcgctccc | 1200 |
| cctccccctc | tttccgatgg | cccttctccg | gcaagacttc | cccaccttgc | tccccagcaa | 1260 |
| atctctccag | gcacaaggct | gcagcctatg | atatcagtga | ggatgaagaa | gactaatgtt | 1320 |
| tcctccctcc | tttcctgtcc | tcccttctg | tcccattacc | ttcagaagct | ctctgttgaa | 1380 |
| ttccaaattg | tgaccccaac | actaaaccta | aggacagcta | caaggaaag | acaactgggg | 1440 |
| aaagaagacc | taggactggg | ggaacccaaa | cagcctgtcc | tgcaagtgac | atcactcacc | 1500 |
| cacacgaagg | aggggactg | caccttagaa | gcctgctctg | catccattta | ccccccccca | 1560 |
| agggctttgt | ttcactgttt | atgttcacgt | gatctcaaca | gggaaattgt | cattttcatt | 1620 |
| aattttttaa | aaaattcgtc | tttcaaatgt | agaactaatt | ttttgcccct | gaggagtggg | 1680 |
| cagaagaagg | aggtagtgta | atacgcagag | gcctttttctt | cccggtatac | tatagcattt | 1740 |
| gccttccgtt | ctgaagctat | gtggcttgcc | aagtccttca | cgaaatgagc | cacgctgatg | 1800 |
| ggtaatttgt | ggagaaatat | cttaattttg | atttccttaa | ggaaaagcga | aaagcagagt | 1860 |
| tacagtcaca | aatcccctga | acgtactgct | gtcaccagtg | tcattgtggc | tgcgggaagg | 1920 |
| agatctgaac | ctaacttttc | ttactccctg | aggagtttct | tgttggaccc | aatggggtcc | 1980 |
| atgaagacac | tgatggggat | ggaagcagac | ccatggcatc | aactgcagtg | tttctgctgt | 2040 |
| gttcatcttc | tcagaaaact | ctgtgaccca | gttctttggg | agcttttgtc | agtctctttc | 2100 |

```
gtgccatcta ccttcgaagg aaggaacact tttagagtta caatgatgag gagaggagcg      2160
ggacaatact caatcctata ccaagtcgat tgagattagt ttcctactgg gagtaagtgc      2220
ctggccctgc tactcctatt tgaatgctat taatattac                             2259
```

<210> SEQ ID NO 8
<211> LENGTH: 367
<212> TYPE: PRT
<213> ORGANISM: Homo sapiens

<400> SEQUENCE: 8

```
Met Asp Ala Gln Cys Ser Ala Lys Val Asn Ala Arg Lys Arg Lys
1               5                   10                  15

Glu Ala Pro Gly Pro Asn Gly Ala Thr Glu Glu Asp Gly Val Pro Ser
                20                  25                  30

Lys Val Gln Arg Cys Ala Val Gly Leu Arg Gln Pro Ala Pro Phe Ser
            35                  40                  45

Asp Glu Ile Glu Val Asp Phe Ser Lys Pro Tyr Val Arg Val Thr Met
50                  55                  60

Glu Glu Ala Ser Arg Gly Thr Pro Cys Glu Arg Pro Val Arg Val Tyr
65                  70                  75                  80

Ala Asp Gly Ile Phe Asp Leu Phe His Ser Gly His Ala Arg Ala Leu
                85                  90                  95

Met Gln Ala Lys Asn Leu Phe Pro Asn Thr Tyr Leu Ile Val Gly Val
            100                 105                 110

Cys Ser Asp Glu Leu Thr His Asn Phe Lys Gly Phe Thr Val Met Asn
        115                 120                 125

Glu Asn Glu Arg Tyr Asp Ala Val Gln His Cys Arg Tyr Val Asp Glu
130                 135                 140

Val Val Arg Asn Ala Pro Trp Thr Leu Thr Pro Glu Phe Leu Ala Glu
145                 150                 155                 160

His Arg Ile Asp Phe Val Ala His Asp Ile Pro Tyr Ser Ser Ala
                165                 170                 175

Gly Ser Asp Asp Val Tyr Lys His Ile Lys Glu Ala Gly Met Phe Ala
            180                 185                 190

Pro Thr Gln Arg Thr Glu Gly Ile Ser Thr Ser Asp Ile Ile Thr Arg
        195                 200                 205

Ile Val Arg Asp Tyr Asp Val Tyr Ala Arg Arg Asn Leu Gln Arg Gly
210                 215                 220

Tyr Thr Ala Lys Glu Leu Asn Val Ser Phe Ile Asn Glu Lys Lys Tyr
225                 230                 235                 240

His Leu Gln Glu Arg Val Asp Lys Val Lys Lys Val Lys Asp Val
                245                 250                 255

Glu Glu Lys Ser Lys Glu Phe Val Gln Lys Val Glu Glu Lys Ser Ile
            260                 265                 270

Asp Leu Ile Gln Lys Trp Glu Glu Lys Ser Arg Glu Phe Ile Gly Ser
        275                 280                 285

Phe Leu Glu Met Phe Gly Pro Glu Gly Ala Leu Lys His Met Leu Lys
290                 295                 300

Glu Gly Lys Gly Arg Met Leu Gln Ala Ile Ser Pro Lys Ser Gln Ser Pro
305                 310                 315                 320

Ser Ser Ser Pro Thr Arg Glu Arg Ser Pro Ser Pro Ser Phe Arg Trp
                325                 330                 335

Pro Phe Ser Gly Lys Thr Ser Pro Pro Cys Ser Pro Ala Asn Leu Ser
            340                 345                 350
```

Arg His Lys Ala Ala Ala Tyr Asp Ile Ser Glu Asp Glu Glu Asp
        355                 360                 365

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
atgagtaatc tggcgagacg                                              20

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
actcaaatgg agcacctgat c                                            21

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
atctatacat tccaccgcgg                                              20

<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
gtaaatggcc atggccacc                                               19

<210> SEQ ID NO 13
<211> LENGTH: 15
<212> TYPE: PRT
<213> ORGANISM: Artificial Sequence
<220> FEATURE:
<223> OTHER INFORMATION: Synthetic peptide

<400> SEQUENCE: 13

Asp Glu Asp Ala Asp Ala Asp Ala Glu Tyr Glu Arg Arg Ser Asn
1               5                   10                  15